United States Patent
Zobi et al.

(10) Patent No.: US 10,589,268 B2
(45) Date of Patent: Mar. 17, 2020

(54) METHOD AND DEVICE FOR PROCESSING TISSUES AND CELLS

(71) Applicant: THE REGENTS OF THE UNIVERSITY OF CALIFORNIA, Oakland, CA (US)

(72) Inventors: Ahmed Zobi, Ceritos, CA (US); Justin Stovner, Long Beach, CA (US); Hugo Salas, Bell, CA (US); David Duarte, Norwalk, CA (US); Jered Haun, Irvine, CA (US); Alan Widgerow, Irvine, CA (US); Derek Banyard, Orange, CA (US)

(73) Assignee: THE REGENTS OF THE UNIVERSITY OF CALIFORNIA, Oakland, CA (US)

(\*) Notice: Subject to any disclaimer, the term of this patent is extended or adjusted under 35 U.S.C. 154(b) by 0 days.

(21) Appl. No.: 16/101,254

(22) Filed: Aug. 10, 2018

(65) Prior Publication Data

US 2018/0361382 A1    Dec. 20, 2018

Related U.S. Application Data

(63) Continuation of application No. PCT/US2017/036429, filed on Jun. 7, 2017.
(Continued)

(51) Int. Cl.
*B01L 3/00* (2006.01)
*B01L 1/00* (2006.01)
(Continued)

(52) U.S. Cl.
CPC ..... *B01L 3/502715* (2013.01); *B01L 3/50273* (2013.01); *B01L 9/527* (2013.01);
(Continued)

(58) Field of Classification Search
CPC ............ B01L 3/5027; B01L 3/502753; B01L 3/502761; B01L 2200/04; B01L 2400/0409
See application file for complete search history.

(56) References Cited

U.S. PATENT DOCUMENTS

| | | | |
|---|---|---|---|
| 4,883,763 A * | 11/1989 | Holen | B01L 3/50273 436/45 |
| 6,527,432 B2 | 3/2003 | Kellogg et al. | |

(Continued)

FOREIGN PATENT DOCUMENTS

| | | |
|---|---|---|
| AT | 478942 T | 9/2010 |
| AT | 500319 T | 3/2011 |

(Continued)

OTHER PUBLICATIONS

English translation of JP 2009075067, Sasao et al, machine translated 2018.*
(Continued)

*Primary Examiner* — Nathan A Bowers
(74) *Attorney, Agent, or Firm* — Vista IP Law Group LLP

(57) ABSTRACT

Provided herein are devices and methods of processing a sample that include, in several embodiments, rotating one or more microfluidic chips that are mounted on a support plate using a motor driven rotational chuck. By spinning one or more of the microfluidic chips about a common center of rotation in a controlled manner, high flow rates (and high shear forces) are imparted to the sample in a controlled manner. Each microfluidic chip can be rotated 180° on the support plate so that the sample can be run back-and-forth through the microfluidic devices. Because the support plate can be driven at relatively high RPMs, high flow rates are generated within the microfluidic chips. This increases the shear forces on the sample and also decreases the processing (Continued)

time involved as the sample can quickly pass through the shear-inducing features of the microfluidic chip(s).

18 Claims, 27 Drawing Sheets

Related U.S. Application Data

(60) Provisional application No. 62/347,290, filed on Jun. 8, 2016.

(51) Int. Cl.
*B04B 9/10* (2006.01)
*B04B 5/04* (2006.01)
*G01N 35/04* (2006.01)
*B01L 9/00* (2006.01)
*G01N 35/00* (2006.01)

(52) U.S. Cl.
CPC ............. *B04B 5/0407* (2013.01); *B04B 9/10* (2013.01); *G01N 35/04* (2013.01); *B01L 3/502707* (2013.01); *B01L 3/502753* (2013.01); *B01L 2200/0621* (2013.01); *B01L 2300/0816* (2013.01); *B01L 2300/0819* (2013.01); *B01L 2300/0829* (2013.01); *B01L 2300/0861* (2013.01); *B01L 2300/0864* (2013.01); *B01L 2300/0883* (2013.01); *B01L 2300/161* (2013.01); *B01L 2400/0409* (2013.01); *G01N 2035/00158* (2013.01); *G01N 2035/00495* (2013.01); *G01N 2035/0449* (2013.01)

(56) References Cited

U.S. PATENT DOCUMENTS

| | | | |
|---|---|---|---|
| 7,074,239 B1 | 7/2006 | Cornwall et al. |
| 7,090,668 B1 | 8/2006 | U et al. |
| 7,104,994 B1 | 9/2006 | Amis et al. |
| 7,390,484 B2 | 6/2008 | Fraser et al. |
| 7,429,488 B2 | 9/2008 | Fraser et al. |
| 7,473,420 B2 | 1/2009 | Fraser et al. |
| 7,501,115 B2 | 3/2009 | Fraser et al. |
| 7,514,075 B2 | 4/2009 | Hedrick et al. |
| 7,553,647 B2 | 6/2009 | Yuan et al. |
| 7,585,670 B2 | 9/2009 | Hedrick et al. |
| 7,595,043 B2 | 9/2009 | Hedrick et al. |
| 7,651,684 B2 | 1/2010 | Hedrick et al. |
| 7,687,059 B2 | 3/2010 | Fraser et al. |
| 7,771,716 B2 | 8/2010 | Hedrick et al. |
| 7,819,138 B2 | 10/2010 | Lee et al. |
| 7,887,795 B2 | 2/2011 | Fraser et al. |
| 7,901,672 B2 | 3/2011 | Fraser et al. |
| 8,048,387 B2 | 11/2011 | Lee et al. |
| 8,101,138 B2 | 1/2012 | Lee et al. |
| 8,105,580 B2 | 1/2012 | Fraser et al. |
| 8,119,121 B2 | 2/2012 | Fraser et al. |
| 8,163,276 B2 | 4/2012 | Hedrick et al. |
| 8,191,715 B2 | 6/2012 | Cho et al. |
| 8,246,947 B2 | 8/2012 | Hedrick et al. |
| 8,337,834 B2 | 12/2012 | Fraser et al. |
| 8,404,229 B2 | 3/2013 | Fraser et al. |
| 8,691,216 B2 | 4/2014 | Fraser et al. |
| 8,771,678 B2 | 7/2014 | Hedrick et al. |
| 8,784,801 B2 | 7/2014 | Alfonso et al. |
| 8,883,499 B2 | 11/2014 | Hedrick et al. |
| 9,101,935 B2 | 8/2015 | Park et al. |
| 9,162,227 B2 | 10/2015 | Borch |
| 9,198,937 B2 | 12/2015 | Fraser et al. |
| 9,213,040 B2 | 12/2015 | Hwang et al. |
| 9,442,108 B2 | 9/2016 | Clime et al. |
| 9,442,109 B2 | 9/2016 | Oosterbroek et al. |
| 9,463,203 B2 | 10/2016 | Hedrick et al. |
| 9,480,718 B2 | 11/2016 | Fraser et al. |
| 9,486,484 B2 | 11/2016 | Alfonso et al. |
| 9,492,483 B2 | 11/2016 | Fraser et al. |
| 9,504,716 B2 | 11/2016 | Hedrick et al. |
| 9,504,718 B2 | 11/2016 | Fraser et al. |
| 9,511,094 B2 | 12/2016 | Fraser et al. |
| 9,511,096 B2 | 12/2016 | Fraser et al. |
| 9,557,316 B2 | 1/2017 | Kim et al. |
| 9,597,395 B2 | 3/2017 | Fraser et al. |
| D784,518 S | 4/2017 | Tremolada |
| 9,631,176 B2 | 4/2017 | Yoshimura et al. |
| 9,737,889 B2 | 8/2017 | Moon et al. |
| 9,737,890 B2 | 8/2017 | Lin et al. |
| 9,808,802 B2 | 11/2017 | Dothie et al. |
| 9,849,149 B2 | 12/2017 | Fraser et al. |
| 9,872,877 B2 | 1/2018 | Fraser et al. |
| 10,058,864 B2 | 8/2018 | Lee |
| 10,307,757 B2 | 6/2019 | Boehm et al. |
| 2002/0142470 A1* | 10/2002 | Clarke .............. B01L 3/502707 436/45 |
| 2004/0137607 A1* | 7/2004 | Tanaami ........... B01L 3/502715 435/287.2 |
| 2006/0083667 A1 | 4/2006 | Kohara et al. |
| 2006/0204556 A1 | 9/2006 | Daniels et al. |
| 2007/0025876 A1* | 2/2007 | Nishijima ......... B01L 3/502715 422/64 |
| 2007/0224591 A1 | 9/2007 | Gui et al. |
| 2008/0140451 A1 | 6/2008 | Hedrick et al. |
| 2009/0075801 A1 | 3/2009 | Hodko et al. |
| 2009/0304644 A1 | 12/2009 | Hedrick et al. |
| 2010/0015104 A1 | 1/2010 | Fraser et al. |
| 2010/0081189 A1* | 4/2010 | Zantl ................ B01L 3/502715 435/287.1 |
| 2010/0120148 A1 | 5/2010 | Tsuchida |
| 2010/0136689 A1 | 6/2010 | Tsuchida |
| 2010/0303774 A1 | 12/2010 | Hedrick et al. |
| 2010/0317094 A1 | 12/2010 | Ricco et al. |
| 2010/0330673 A1 | 12/2010 | Fraser et al. |
| 2011/0003388 A1 | 1/2011 | Fraser et al. |
| 2011/0045959 A1 | 2/2011 | Kurihara et al. |
| 2011/0085950 A1* | 4/2011 | Lee .................... B01L 3/50273 422/504 |
| 2011/0158968 A1 | 6/2011 | Fraser et al. |
| 2011/0230328 A1 | 9/2011 | Kinoshita et al. |
| 2011/0294203 A1 | 12/2011 | Tsuchida et al. |
| 2012/0058093 A1 | 3/2012 | Fraser et al. |
| 2012/0093783 A1 | 4/2012 | Pinkernell et al. |
| 2012/0121556 A1 | 5/2012 | Fraser et al. |
| 2012/0221253 A1 | 8/2012 | Hedrick et al. |
| 2012/0259289 A1 | 10/2012 | Byrnes et al. |
| 2012/0264200 A1 | 10/2012 | Hedrick et al. |
| 2012/0308518 A1 | 12/2012 | Fraser |
| 2012/0308536 A1 | 12/2012 | Hedrick et al. |
| 2012/0315257 A1 | 12/2012 | Fraser et al. |
| 2013/0060338 A1 | 3/2013 | Hedrick et al. |
| 2013/0108592 A1 | 5/2013 | Pinkernell et al. |
| 2013/0121974 A1 | 5/2013 | Fraser et al. |
| 2013/0288290 A1 | 10/2013 | Hedrick et al. |
| 2013/0344035 A1 | 12/2013 | Fraser et al. |
| 2014/0227234 A1 | 8/2014 | Fraser et al. |
| 2014/0227341 A1 | 8/2014 | Fraser et al. |
| 2014/0369970 A1 | 12/2014 | Alfonso et al. |
| 2014/0377866 A1 | 12/2014 | Haun et al. |
| 2015/0023931 A1 | 1/2015 | Hedrick et al. |
| 2015/0138567 A1* | 5/2015 | Huang ..................... B04B 7/08 356/614 |
| 2015/0152375 A1 | 6/2015 | Hedrick et al. |
| 2015/0196601 A1 | 7/2015 | Fraser et al. |
| 2015/0218505 A1 | 8/2015 | Hedrick et al. |
| 2015/0231244 A1 | 8/2015 | Chi et al. |
| 2016/0113967 A1 | 4/2016 | Hedrick et al. |
| 2016/0137970 A1 | 5/2016 | Hedrick et al. |
| 2016/0143952 A1 | 5/2016 | Fraser et al. |
| 2016/0177250 A1 | 6/2016 | Arm et al. |
| 2016/0310540 A1 | 10/2016 | Fraser et al. |
| 2017/0025930 A1* | 1/2017 | Roswech .............. B04B 5/0421 |
| 2017/0036208 A1 | 2/2017 | Veres et al. |
| 2017/0065638 A1 | 3/2017 | Fraser |
| 2017/0080422 A1 | 3/2017 | Maaskant et al. |

(56) References Cited

U.S. PATENT DOCUMENTS

| | | |
|---|---|---|
| 2017/0114325 A1 | 4/2017 | Alfonso et al. |
| 2017/0136066 A1 | 5/2017 | Fraser et al. |
| 2017/0136067 A1 | 5/2017 | Hedrick et al. |
| 2017/0136069 A1 | 5/2017 | Hedrick et al. |
| 2017/0173589 A1 | 6/2017 | Clime et al. |
| 2017/0205322 A1 | 7/2017 | Arm et al. |
| 2017/0281771 A1 | 10/2017 | Fraser et al. |
| 2017/0296697 A1 | 10/2017 | Fraser et al. |
| 2018/0136243 A1 | 5/2018 | Boehm |
| 2019/0024033 A1 | 1/2019 | Chander et al. |
| 2019/0091680 A1 | 3/2019 | Lee |
| 2019/0201900 A1 | 7/2019 | Shachar et al. |
| 2019/0224675 A1 | 7/2019 | Stahl et al. |

FOREIGN PATENT DOCUMENTS

| | | |
|---|---|---|
| AT | 501247 T | 3/2011 |
| AT | 524070 T | 9/2011 |
| AU | 2004318008 A1 | 10/2006 |
| AU | 2013216683 B2 | 9/2007 |
| AU | 2010242780 A1 | 12/2011 |
| AU | 2005332046 B2 | 5/2013 |
| AU | 2011254198 B2 | 3/2015 |
| AU | 2014323629 A1 | 5/2016 |
| AU | 2013216683B2 B | 6/2016 |
| CA | 2609361 A1 | 11/2006 |
| CA | 2327789 C | 9/2007 |
| CA | 2760574 A1 | 11/2010 |
| CA | 2799901 A1 | 11/2011 |
| CA | 2924883 A1 | 3/2015 |
| CA | 162188 S | 1/2016 |
| CA | 2963468 A1 | 4/2016 |
| CA | 2572113 C | 4/2017 |
| CA | 2609361 C | 11/2017 |
| CN | 101443023 A | 5/2009 |
| CN | 106434542 A | 1/2010 |
| CN | 201389496 Y | 1/2010 |
| CN | 102458302 A | 5/2012 |
| CN | 102002478 B | 1/2013 |
| CN | 102861105 A | 1/2013 |
| CN | 103038333 A | 4/2013 |
| CN | 104630139 A | 5/2015 |
| CN | 105934155 A | 9/2016 |
| CN | 106834121 A | 6/2017 |
| DK | 1778834 T3 | 11/2010 |
| DK | 1778833 T3 | 6/2011 |
| DK | 1885382 T3 | 6/2011 |
| DK | 1599575 T3 | 1/2012 |
| DK | 1778834 T5 | 1/2012 |
| DK | 1921133 T3 | 8/2015 |
| DK | 1638507 T3 | 6/2017 |
| DK | 1670315 T3 | 8/2017 |
| DK | 2571975 T3 | 10/2017 |
| DK | 3046417 T3 | 10/2017 |
| EP | 2145951 A1 | 1/2010 |
| EP | 2145952 A1 | 1/2010 |
| EP | 1778833 B1 | 3/2011 |
| EP | 1885382 B1 | 3/2011 |
| EP | 2332555 A3 | 6/2011 |
| EP | 2343360 A1 | 7/2011 |
| EP | 2305276 A3 | 9/2011 |
| EP | 2308963 A3 | 9/2011 |
| EP | 2371943 A1 | 10/2011 |
| EP | 1778834 B9 | 11/2011 |
| EP | 1599575 B9 | 3/2012 |
| EP | 2348103 A3 | 7/2012 |
| EP | 2571975 A2 | 3/2013 |
| EP | 1743021 B1 | 3/2014 |
| EP | 1778293 B1 | 4/2015 |
| EP | 1776126 B1 | 5/2015 |
| EP | 1921133 B1 | 5/2015 |
| EP | 2980206 A1 | 2/2016 |
| EP | 2617427 B1 | 8/2016 |
| EP | 3046417 A4 | 9/2016 |
| EP | 3106511 A1 | 12/2016 |
| EP | 2422622 B1 | 1/2017 |
| EP | 1638507 B1 | 3/2017 |
| EP | 1670315 B1 | 4/2017 |
| EP | 2571975 B1 | 7/2017 |
| EP | 3046417 B1 | 7/2017 |
| EP | 2574663 B1 | 8/2017 |
| EP | 2380970 B1 | 12/2017 |
| EP | 3106512 B1 | 3/2018 |
| EP | 3299451 A1 | 3/2018 |
| EP | 2465923 B1 | 4/2018 |
| ES | 2364957 T3 | 9/2011 |
| ES | 2364689 T3 | 2/2012 |
| ES | 2373551 T3 | 2/2012 |
| ES | 2545385 T3 | 9/2015 |
| ES | 2633604 T3 | 9/2017 |
| ES | 2641547 T3 | 11/2017 |
| ES | 2649387 T3 | 1/2018 |
| HK | 11078009 A1 | 6/2011 |
| HK | 1096424 A1 | 2/2013 |
| HK | 1165261 A1 | 8/2015 |
| HR | 20171471 T1 | 11/2017 |
| JP | 2008278821 A | 11/2008 |
| JP | 2008278822 A | 11/2008 |
| JP | 2009-75067 A | 4/2009 |
| JP | 2009189280 A | 8/2009 |
| JP | 2009189281 A | 8/2009 |
| JP | 2009189282 A | 8/2009 |
| JP | 2009269930 A | 11/2009 |
| JP | 2010032444 A | 2/2010 |
| JP | 2010043876 A | 2/2010 |
| JP | 2010075066 A | 4/2010 |
| JP | 2010075114 A | 4/2010 |
| JP | 2010095531 A | 4/2010 |
| JP | 2010127620 A | 6/2010 |
| JP | 2010127708 A | 6/2010 |
| JP | 2010148450 A | 7/2010 |
| JP | 2010148451 A | 7/2010 |
| JP | 2011010615 A | 1/2011 |
| JP | 2011010616 A | 1/2011 |
| JP | 2012051923 A | 3/2012 |
| JP | 2012075439 A | 4/2012 |
| JP | 2012149088 A | 8/2012 |
| JP | 2014031389 A | 2/2014 |
| JP | 05960689 B2 | 8/2016 |
| JP | 2016136956 A | 8/2016 |
| JP | 06208787 B2 | 10/2017 |
| JP | 2018030815 A | 3/2018 |
| KR | 2005109941 A | 11/2005 |
| KR | 2006025180 A | 3/2006 |
| KR | 2006030861 A | 4/2006 |
| KR | 2007002058 A | 1/2007 |
| KR | 2007017974 A | 2/2007 |
| KR | 2007038538 A | 4/2007 |
| KR | 2007089254 A | 8/2007 |
| KR | 779812 B1 | 11/2007 |
| KR | 2008017389 A | 2/2008 |
| KR | 811995 B1 | 3/2008 |
| KR | 2008103611 A | 11/2008 |
| KR | 930139 B1 | 12/2009 |
| KR | 2010029272 A | 3/2010 |
| KR | 1083454 B1 | 11/2011 |
| KR | 2012003961 A | 1/2012 |
| KR | 2012020143 A | 3/2012 |
| KR | 1127305 B1 | 4/2012 |
| KR | 2012038534 A | 4/2012 |
| KR | 1145508 B1 | 5/2012 |
| KR | 1150666 B1 | 7/2012 |
| KR | 1197909 B1 | 11/2012 |
| KR | 2013038412 A | 4/2013 |
| KR | 1278437 B1 | 6/2013 |
| KR | 1310578 B1 | 9/2013 |
| KR | 1400544 B1 | 5/2014 |
| KR | 2016055827 A | 5/2016 |
| KR | 2017115296 A | 10/2017 |
| KR | 2017115377 A | 10/2017 |
| MX | 2011011402 A | 2/2012 |
| MX | 2016003127 A | 10/2016 |
| WO | WO2009076548 A1 | 6/2000 |
| WO | WO2003024215 A1 | 3/2003 |

(56) References Cited

FOREIGN PATENT DOCUMENTS

| | | |
|---|---|---|
| WO | WO2003053346 A2 | 7/2003 |
| WO | WO2003053362 A2 | 7/2003 |
| WO | WO2005012480 A2 | 2/2005 |
| WO | WO2006014156 A1 | 2/2006 |
| WO | WO20060175980 A1 | 7/2006 |
| WO | WO2006069349 A9 | 9/2006 |
| WO | WO2006039129 A8 | 12/2006 |
| WO | WO2007061530 A1 | 5/2007 |
| WO | WO2007139551 A1 | 12/2007 |
| WO | WO2008060466 A3 | 8/2008 |
| WO | WO2008013863 A3 | 10/2008 |
| WO | WO2008140046 A1 | 11/2008 |
| WO | WO2006112941 B1 | 12/2008 |
| WO | WO2006127007 A3 | 4/2009 |
| WO | WO2009055610 A1 | 4/2009 |
| WO | WO2008140044 A8 | 8/2009 |
| WO | WO2009101910 A1 | 8/2009 |
| WO | WO2010021993 A1 | 2/2010 |
| WO | WO2010035709 A1 | 4/2010 |
| WO | WO2010073808 A1 | 7/2010 |
| WO | WO2010124235 A1 | 10/2010 |
| WO | WO2010127310 A1 | 11/2010 |
| WO | WO2011145075 A2 | 11/2011 |
| WO | WO 2013/075145 | 5/2013 |
| WO | WO2013144883 A2 | 10/2013 |
| WO | WO2013144883 A3 | 11/2013 |
| WO | WO2014016750 A1 | 1/2014 |
| WO | WO2014064642 A1 | 5/2014 |
| WO | WO 2014/130391 | 8/2014 |
| WO | WO2015042182 A1 | 3/2015 |
| WO | WO 2015/127126 | 8/2015 |
| WO | WO2015120388 A1 | 8/2015 |
| WO | WO2015140737 A1 | 9/2015 |
| WO | WO2016007434 A1 | 1/2016 |
| WO | WO2016054592 A1 | 4/2016 |
| WO | WO2017195156 A1 | 11/2017 |

OTHER PUBLICATIONS

PCT International Search Report for PCT/US2017/036429, Applicant: The Regents of the University of California, Form PCT/ISA/210 and 220, dated Sep. 8, 2017 (8pages).
PCT Written Opinion of the International Search Authority for PCT/US2017/036429, Applicant: The Regents of the University of California, Form PCT/ISA/237, dated Sep. 8, 2017 (12pages).
PCT International Preliminary Report on Patentability (Chapter I of the Patent Cooperation Treaty) for PCT/US2017/036429, Applicant: The Regents of the University of California, Form PCT/IB/326 and 373, dated Dec. 20, 2018 (14pages).
Notice of Preliminary Rejection (non-final) dated Mar. 21, 2019 for Korean Patent Application No. 10-2019-7000183, Applicant: The Regents of the University of California (19pages).
Response to Office Action dated Oct. 4, 2019 in Korean Application No. 10-2019-7000183, (19pages).
Notice of Allowance dated Oct. 22, 2019 in Korean Application No. 10-2019-7000183, (2pages).
The extended European Search Report dated Nov. 11, 2019 in European Patent Application No. 17810972.1101 (9pages).
Communication pursuant to Rules 70(2) and 70(a) EPC dated Nov. 26, 2019 in n European Patent Application No. 17810972.1101 (1page).

* cited by examiner

METHOD AND DEVICE FOR PROCESSING TISSUES AND CELLS

RELATED APPLICATION

This Application is a continuation of International Application No. PCT/US2017/036429, filed Jun. 7, 2017, which claims priority to U.S. Provisional Patent Application No. 62/347,290 filed on Jun. 8, 2016, each of which is hereby incorporated by reference in its entirety. Priority is claimed pursuant to 35 U.S.C. §§ 119, 120 and any other applicable statute.

TECHNICAL FIELD

The technical field generally relates to devices and methods for applying shear stress to live cells, and/or tissue, reagents, particles, and fluids. In particular, the technical field relates to utilizing rotational forces in conjunction with microfluidic-based devices for applying shear stress to live cells, and/or tissue, reagents, particles, and fluids.

BACKGROUND

A variety of techniques and procedures are used to process tissue. In some applications, chemicals or enzymes are added to tissue to break-up larger clumps or aggregates of tissue into smaller and smaller pieces. For example, digestive enzymes such as collagenase, trypsin, or dispase are used to digest tissue such as adipose tissue. Such enzymatic processing typically involves washing, followed by enzymatic degradation and centrifugation. This enzymatic approach may suffer from variability due to different activity levels of the digesting enzymes. Moreover, these methods require added costs for reagents including expensive enzymes that are derived from bacteria and take considerable time to complete, as well as additional processing and/or wash steps to minimize the effects of enzyme contamination.

Non-enzymatic approaches have also been developed to process tissue, including fat tissue. For example, ultrasonic cavitation has been proposed for the isolation of stromal vascular fraction from adipose tissue. See U.S. Pat. No. 8,440,440, which is incorporated in its entirety by reference herein. Still other methods involve the use of beads to homogenize adipose tissue such as that disclosed in International Patent Publication No. WO2014-036094, which is incorporated in its entirety by reference herein. U.S. Pat. No. 9,580,678 (which is incorporated in its entirety by reference herein) discloses a microfluidic tumor dissociation device that uses a plurality of serially arranged channels or stages with expansion and constriction regions that are used to break-up the tumor tissue. A syringe pump is used to pass tumor tissue back-and-forth through the microfluidic device.

Processing of tissues such as fat tissue has particular importance to the field of plastic and reconstructive surgery where fat tissue is transferred from one location to another to fill soft tissue defects (i.e., fat grafting). Cell-assisted lipotransfer (CAL) is a technique that involves the addition of the stromal vascular fraction (SVF) to fat grafts, and has resulted in significant improvements in fat graft retention. Typically, the SVF is harvested from adipose tissue by a short digestion step using the enzyme collagenase. More recently, a technique called 'nanofat grafting' was developed, whereby standard lipoaspirate is homogenized by manually passing it vigorously between two connected syringes, and then reinjecting the homogenized lipoaspirate in human patients for the correction of superficial rhytides and pigmentation. It was also found that the nanofat processing methods can serve as a means of mechanically dissociating SVF while also stressing the cells to generate multipotent or even pluripotent populations. For example, nanofat-derived SVF is known to have a greater proportion of mesenchymal stem cells (MSCs), adipose derived stem cells (ADSCs), endothelial progenitor cells (EPCs), and Muse cells. It was postulated that the amount of stress that is applied to cells directly correlates with stem-like properties.

MSCs, for example, may be used to treat diabetic ulcers. Current treatments of diabetic foot ulcers, such as allografts, are costly and may not be effective due to the potential rejection by the patient. If such ulcers are left untreated, patients have to undergo limb amputation which, in turn, leads to additional health complications. One innovative solution to treat these ulcers is through the use of MSCs for the direct treatment of these ulcers. However, current approaches of obtaining such cells are lengthy, complicated, and yield variable results in terms of cell yield, quantity and reproducibility. There is a need for quick and cost-effective methods for obtaining processed tissue.

SUMMARY

In view of the need for devices, systems and method for processing tissue in an efficient, effective and reproducible manner, various embodiments of such devices, methods and systems are provided herein, as well as uses for same in developing, producing, or otherwise preparing cells for treating or administering to a subject.

In several embodiments, there is provided a system for processing biological samples comprising a support plate comprising a central portion comprising a receiving element, a lateral portion comprising a plurality of interacting regions, each configured to reversibly interact with a plurality of carriages, a plurality of carriages, wherein each of the plurality of carriages is configured to be operatively coupled to the lateral portion of the support plate.

In several embodiments, the receiving element is configured to reversibly interact with a drive shaft of a motor, the motor configured to apply centrifugal movement to the support plate. In one embodiment, the central portion lies in a plane perpendicular to an axis of rotation of the drive shaft of the motor and the lateral portion extends radially from the central portion and at least partially lies within a plane parallel to the plane of the central portion.

In several embodiments, each of the plurality of carriages comprises a first end and a second end and a base portion extending between the first and second ends, and a receiving region configured to reversibly interact with a microfluidic chip that is fluidically coupled to at least one sample chamber configured to receive a sample for processing. In several embodiments, each of the plurality of carriages comprises a post, rod, shaft, or other extension that extends substantially orthogonally from the base portion and is configured to interact (e.g., to connect, attach, or otherwise cause to interact with) with one of the plurality of interacting regions of the lateral portion. In several embodiments, each of the plurality of carriages is positioned co-axially about one of a plurality of axes, wherein during operation each axis extends substantially parallel to the axis of rotation of the drive shaft of the motor, and wherein each of the plurality of carriages is at least intermittently rotatable about one of the plurality of axes. Depending on the embodiment, the carriages can rotate to various degrees. For example, in several embodiments, the carriages are induced to rotate through an arc of about 180 degrees.

In several embodiments, the system further comprises at least one microfluidic chip that serves to hold and process the sample according to the system. In several embodiments, each microfluidic chip comprises a central body portion positioned between a first end and a second end and at least one microfluidic channel extending between the first and second ends, the at least one channel comprising varied dimensions and configured to allow passage of the sample from the first end to the second end. In several embodiments, each of the first and second end are configured to fluidically interact with the sample chamber. For ease of use, each individual microfluidic chip is dimensioned to fit within a corresponding receiving region on a corresponding carriage. In several embodiments, each microfluidic chip is reversibly fluidically coupled to a sample chamber on each of the first and second ends.

Optionally, some embodiments comprise a sample chamber comprising a vent and a vent channel that is fluidly connected to the interior of the sample chamber. In several embodiments, each sample chamber is reversibly fluidically coupled to the microfluidic chip via an adapter.

In several embodiments, each carriage comprises a capture element on the first and second ends of the carriage, the capture elements configured to communicate with a release element on the lateral portion of the support plate, wherein the communication between the capture elements and release element allows the intermittent rotation of each of the plurality of carriages. In other words, the capture elements serve to hold the carriage in a desired position until such time as there is a signal (or force, or lack thereof) that allows the capture elements to disengage or otherwise cease interaction with the release element, which subsequently allows rotation of the carriage, to be followed be a reengagement of the capture element in order to stop the motion of the carriage (in several embodiments, this allows the rotation of the carriage through an arc of 180 degrees at a desired time in a tissue processing protocol). In several embodiments, the capture elements comprise magnets of a first polarity and the release element comprises a magnet of an opposite polarity.

In several embodiments, the lateral portion of the support plate comprises a disc, with the interacting regions spaced circumferentially around the disc. In some such embodiments, the lateral portion and the central portion are a unitary structure, though in other embodiments the support plate comprises multiple pieces that are connected or integrated prior to use.

In several embodiments, the lateral portion of the support plate comprises a plurality of arms, with each arm comprising a corresponding interacting region. In one embodiment, the arms and the central portion are a unitary structure. In additional embodiments, the arms and the central portion are separate structures joined together. In some embodiments, the arms are hinged relative to the central portion. In some such embodiments, the hinges allow the arms to move into the plane of the axis that is substantially parallel to the axis of rotation of the drive shaft of the motor during operation. In several embodiments, this allows for a gentle start up and stop process such that acute application or removal of centrifugal force does not disrupt the cells/tissue sample.

In several embodiments, the interacting regions of the lateral portion comprise a through hole that receives the post (or other structure) from the corresponding carriage. In several embodiments, the receiving region is positioned on an upper surface of the base portion of the carriage. In several embodiments, the post extends from a bottom surface of the base portion of the carriage. In such embodiments, the post (or other structure) extends from the bottom of the carriage and passes through the through hole (receiving region) of the lateral portion (e.g., arm) and is secured (though allowing rotation relative to the lateral portion), for example by a nut, pin, clamp or other such mechanism. In several embodiments, the intermittent rotation of each of the carriages is accomplished via the interaction of gears positioned on the lateral portion with fixed teeth that induce rotation of each carriage.

In several embodiments, the lateral portion comprises at least three arms, each of the three arms comprising an interacting region configured to interact with one of at least three carriages comprising a first and second end, each of the carriages configured to reversibly interact with one of at least three microfluidic chips, each chip comprising a first end, a second end, and a body therebetween, each end of the microfluidic chip being fluidically coupled to a sample chamber, and the body of the chip comprising a plurality of microfluidic pathways extending between the first and second ends, and wherein the carriages are configured to intermittently rotate between a first position where the first end is positioned at a first location at a first distance from the receiving element of the central portion and a second position wherein the first end is positioned at a second location at a second distance from the receiving element of the central portion, wherein the first distance is greater than the second distance.

Depending on the embodiment, the system can optionally include an enclosure, wherein the enclosure separates the system from an external environment.

Depending on the embodiment, the system optionally further comprises a motor operably connected to the drive shaft. In several embodiments, the motor is controlled by a controller unit that allows control of the rotational speed of the motor, the controller unit comprising an interface that allows a user to program (or select from preprogrammed) a protocol to process tissue.

Also provided herein are methods for processing a biological sample. For example, in several embodiments, there is provided a method for processing a biological sample, comprising loading a biological sample into a first sample chamber that is configured to be fluidically coupled to a microfluidic chip, the chip comprising a central body portion positioned between a first end and a second end, the first end configured to be fluidically coupled to the first sample chamber and the second end fluidically coupled with a second sample chamber, at least one microfluidic channel extending between the first and second ends, the at least one channel comprising varied dimensions and configured to allow passage of the sample from the first end to the second end, reversibly coupling the microfluidic chip with a receiving region of one of a plurality of carriages that is part of a centrifugal device, the centrifugal device comprising a support plate comprising a central portion and a lateral portion, the lateral portion extending radially from the central portion and lying within a plane parallel to the plane of the central portion, each of the carriages operatively coupled to the lateral portion of the support plate and comprising a first end, a second end, and a base portion extending between the first and second ends, the base portion comprising the receiving region, each of the carriages configured to be rotatable about an axis substantially perpendicular to the plane of the central portion, wherein the carriage starts in a first position in which the first end is positioned at a first distance from the central portion of the support plate and is rotatable to a second position where the second end is positioned such that the second end is positioned at the first distance from the central portion of the support plate, and applying a rotational force to the centrifugal device, thereby causing the sample to pass from the first sample chamber coupled to the first end of the microfluidic chip through the at least one microfluidic channel extending between the first and second ends and into the second sample chamber, allowing rotation of the carriage between the first and second positions; and applying additional rotational force to cause the sample to pass from the second sample chamber through the at least one microfluidic channel extending between the second and first ends and back into the first sample chamber. In several embodiments, the biological sample comprises adipose tissue, though other tissue types can be processed using the systems and methods disclosed herein. For example, adipose tissue, tumor tissue, cellular preparations, lipoaspirates, cultured cells, and the like can readily be processed.

Further provide, in several embodiments, is a system for processing samples comprising a motor coupled to a vertically oriented rotatable chuck, a support plate containing a plurality of rotatable carriages positioned radially about the support plate, wherein the support plate is mounted on or secured to the rotatable chuck; and at least one microfluidic chip disposed on one of the rotatable carriages, the at least one microfluidic chip defining a fluid path formed by one or more microfluidic channels disposed therein and extending between a first port of the microfluidic chip to a second port located at an opposing end of the microfluidic chip.

In several embodiments, such a system may further comprise a first sample holding chamber and a second sample holding chamber disposed in the rotatable carriage, the first sample holding chamber fluidically coupled to the at least one microfluidic chip via the first port and the second sample holding chamber fluidically coupled to the at least one microfluidic chip via the second port. In several embodiments, the first sample holding chamber and the second sample holding chamber are fluidically coupled to the at least one microfluidic chip via respective adapters interposed between the first port and the first sample holding chamber and the second port and the second sample holding chamber. In several embodiments, the at least one microfluidic chip comprises a first sample holding chamber and a second sample holding chamber disposed in the at least one microfluidic chip.

In several embodiments, the support plate comprises a plurality of arms and wherein each of the plurality of arms holds a rotatable carriage. In some such embodiments, the plurality of arms are secured to a separate central hub. In several embodiments, the support plate comprises a first magnetic element disposed therein or thereon and disposed adjacent to an end of the rotatable carriage, the rotatable carriage further comprising a second magnetic element disposed therein or thereon.

Alternatively, in several embodiments, the rotatable carriages are coupled to a gear set disposed in a gear assembly mounted to the support plate, wherein the gear set includes an exposed gear on a radially outward portion of the gear assembly. In several embodiments, the gear assembly or the support plate further comprises a stationary magnet disposed therein and the rotatable carriages contains a pair of magnetic elements disposed at opposing ends thereof.

In several embodiments, the plurality of rotatable carriages is rotatable in a plane that is substantially parallel to a rotational plane of the support plate. In several embodiments, the plurality of rotatable carriages is rotatable in a plane that is substantially orthogonal to a rotational plane of the support plate.

In several embodiments, the system further comprises an electromagnet disposed in the support plate beneath each of the plurality of rotatable carriages, wherein the rotatable carriages comprise a magnetic post element extending through an aperture formed in the support plate.

In several embodiments, the microfluidic chip has a fluid path that comprises a microfluidic channel formed by a pair of tapered regions that join in a narrowed constriction in a center region of the fluid path. In several embodiments, the tapered regions comprise continuous tapered regions. In one embodiment, the tapered regions comprise stepped tapered regions. In additional embodiments, the fluid path comprises a microfluidic channel having a plurality of expansion and constriction regions disclosed along a length of the channel. In several embodiments, the plurality of expansion and constriction regions are defined by curved walls in the microfluidic channel. In several embodiments, the plurality of expansion and constriction regions are defined by angled walls in the microfluidic channel. In several embodiments, the fluid path comprises a microfluidic channel having a plurality of fin shaped pockets disposed along the length of the microfluidic channel. In several embodiments, the fluid path comprises a plurality of branching channels of decreased dimensions that recombine with a plurality of branching channels of increased dimensions. In one embodiment, each branching channel comprises a bifurcation. In an additional embodiment, each bifurcation comprises a sharpened edge.

In several embodiments, at least one of the first sample holding chamber and a second sample holding chamber comprise a syringe barrel, for example a standard 2 mL, 5 mL, 10 mL, 20 mL, or 60 mL syringe barrel. In several embodiments, there is additionally included a filter interposed between the at least one microfluidic chip and one of the first sample holding chamber or the second sample holding chamber. In some embodiments, the filter is located upstream of or before the microfluidic chip and is configured to filter the sample to prevent clogging of the microfluidic chip. In some examples, the upstream filter can include a mesh that is configured to cut or micronize tissue or tissue fragments to allow the sample to pass through the microfluidic chip without clogging. The cutting or micronization of the sample is configured to produce macroscopic aggregates for the purpose of microfluidic shearing in the microfluidic chips. In some embodiments, the filter is located downstream of or after the microfluidic chip to only allow a certain sized sample to pass out of the device for collection.

In several embodiments, the system also includes a sample holding chamber disposed in the rotatable carriage and coupled to the first port of the microfluidic chip and a syringe coupled to the second port of the microfluidic chip, wherein the syringe is mounted generally perpendicular to a rotational plane of the microfluidic chip. In several embodiments, the system disclosed herein can optionally comprise a vertically moveable plate or ring coupled to a plunger of the syringe. In several embodiments, the vertically moveable plate or ring comprises an internally threaded bearing mounted on rotatable, threaded rod. Optionally, certain embodiments further comprise a second motor coupled to the threaded rod.

In some embodiments, the systems have at least one of the first sample holding chamber and the second sample holding chamber comprising an inlet having a one-way valve disposed therein.

In several embodiments, there is provided a method of using the systems disclosed herein, comprising rotating the support plate to move the sample into the one or more microfluidic channels of the at least one microfluidic chip via the first port and out the second port, rotating the rotatable carriage containing the at least one microfluidic chip through approximately 180°, rotating the support plate to move the sample into the one or more microfluidic channels via the second port and out the first port, rotating the rotatable carriage containing the at least one microfluidic chip through approximately 180°, and repeating these steps a plurality of times, until a sample is processed to a desired degree.

In several such methods, the sample moves between a first sample holding chamber fluidically coupled to the first port and a second sample holding chamber fluidically coupled to the second port. In several embodiments, at least one of the first sample holding chamber and the second sample holding chamber comprises a syringe barrel.

In several embodiments, the sample comprises tumor tissue. In several embodiments, the sample comprises fat tissue. In several embodiments, the sample comprises a fluid with one or more reagents. In several embodiments, the sample comprises particles (e.g., nanoparticles, magnetic particles, particles coated with a reagent or antibody, and the like). In several embodiments, the sample comprises a cell containing fluid.

In some embodiments, after processing tissue, the methods disclosed herein further comprise injecting the processed tissue (e.g., adipose tissue) into a subject.

Supplementing the above described systems, devices and methods, there is also provided herein a system for processing samples comprising a support plate including a plurality of arms, wherein the plurality of arms extends radially from the support plate, a motor, coupled to the support plate and configured to rotate the support plate; and a plurality of carriages, wherein each of the plurality of carriages is arranged on one of the plurality of arms on the support plate, wherein each of the plurality of carriages is positioned co-axially about one of a plurality of axes, wherein each axis extends perpendicularly from the arm that the carriage is arranged on, wherein each of the plurality of carriages is configured to receive a microfluidic chip and at least one sample chamber for receiving a sample for processing, wherein the at least one sample chamber includes an opening that is fluidly connected to the microfluidic chip, and wherein each of the plurality of carriages is rotatable about one of the plurality of axes.

In several embodiments, the system further comprising a controller configured to drive the motor, wherein the controller is configured to adjust the rotational speed or rotations per minute (RPM) of the motor. In several embodiments, the controller is adjustable or programmable with a pre-determined spin program or sequence of operations. In several embodiments, the controller is configured (or configurable) to ramp up the spin rate of the motor to an RPM rate such that the sample is configured to flow from a first end of the microfluidic chip to a second end of the microfluidic chip. In several embodiments, the controller is configured to accelerate or decelerate the RPMs of the motor such that each of the plurality of carriages is configured to rotate about one of the plurality of axes.

In several embodiments, each of the plurality of carriages is configured to rotate 180 degrees about one of the plurality of axes. Moreover, in several embodiments, each of the plurality of carriages is configured to receive a first sample chamber and a second sample chamber, wherein the first sample chamber is positioned on a first end of the microfluidic chamber, and wherein the second sample chamber is positioned on a second end of the microfluidic chamber.

Some embodiments, include the at least one sample chamber being attached to an end of the microfluidic chip using an adaptor. The adaptor can include any one of a Luer slip, slip tip connectors, a Luer lock, and a rotating collar. The adaptor can comprise metal or polymer materials, depending on the embodiment, and also on whether the microfluidic chip is disposable or reusable (e.g., can be sterilized).

In several embodiments, the support plate is placed inside an encasement, the encasement configured to protect a user from the system for processing samples. The encasement comprises any material such as a plastic material or a metal, the material being provided at a thickness sufficient to prevent penetration or rupture of the encasement by decreased vacuum pressure, cold temperatures, changes in heat, or debris created by the centrifugal rotation of the support plate. In several embodiments, the encasement is configured to be opened and closed in order to place a sample, remove a sample, or manually rotate one or more carriages, if needed. In several embodiments, the encasement is optically transparent and is configured to allow the operation of the system for processing samples to be monitored.

In embodiments, comprising a plurality of arms, in some such embodiments, each of the plurality of arms further comprises a first engagement structure, a second engagement structure located a distance from the first engagement structure, wherein the first engagement structure and the second engagement structure are each configured to engage with one of a first structure located on a first end of the carriage and a second structure located on a second end of the carriage. In several such embodiments, the first and second engagement structures are configured to release and engage the first structure and the second structure interchangeably such that the carriage is configured to move between a plurality of orientations about one of the plurality of axes.

In several embodiments, the first engagement structure and the second engagement structure are magnets and the first structure and second structure comprise magnetically responsive materials. In several embodiments, the first engagement structure and the second engagement structure comprise magnetically responsive materials and the first structure and second structure are magnets. In several embodiments, the first engagement structure is located distally from the second engagement structure along a length of each of the plurality of arms. In order to cause movement of the carriage(s), in several embodiments, an acceleration or deceleration force is configured to move the carriage between the plurality of orientations. In several embodiments, the carriage comprises a gear assembly, the gear assembly is configured to move the carriage between the plurality of orientations. In some embodiments, the carriage comprises a centripetal ratchet, the centripetal ratchet configured to move the carriage between the plurality of orientations.

To enable proper flow of a sample through the microfluidic chip(s), in several embodiments, the at least one sample chamber includes a vent and a vent channel that is fluidly connected to the interior of the sample channel, wherein the vent is configured to provide laminar flow through the sample chamber (e.g., by preventing vacuum). In several embodiments, the vent is located on an opposite end of the sample chamber as the opening. Depending on the embodiment, the sample chamber can be any desired shape, including rectangular, square, ellipsoid, columnar, oval, or other polygonal shape. In one embodiment, the sample chamber is rectangular. In some alternative embodiments, the sample chamber is a syringe. In some such embodiments, the syringe comprises a chamber having an adaptor end, the adaptor end having an opening configured to fluidly connect to the microfluidic chip, a plunger comprising a seal disposed in the chamber; and a depressor attached to a distal end of the plunger and configured to advance and withdraw the plunger. In some embodiments, the syringe includes a vent and a vent channel that is fluidly connected to the interior of the chamber, wherein the vent is configured to provide laminar flow through the syringe. Additionally, in several embodiments, the syringe can optionally include a secondary syringe plunger, the secondary syringe plunger disposed within the vent channel and is configured to selectively open and close the vent channel. In such embodiments, the secondary syringe is optionally coupled to the depressor such that movement of the depressor is configured to advance and withdraw both the plunger and secondary plunger. In several embodiments, the adaptor end of the syringe is configured to receive a needle. In several embodiments, the syringe is configured to be removable from the microfluidic chip and the sample is configured to be directly injected into an injection site.

In several embodiments, each of the plurality of chambers (e.g., chambers to retain a microfluidic chip) is retained in an opening of each of the plurality of arms, wherein each of the plurality of chambers extends through the opening of each of the plurality of arms. In several embodiments, each of the plurality of chambers is retained along a plane of each of the plurality of arms. In several embodiments, each of the plurality of chambers is retained in the opening of each of the plurality of arms with at least one pin that is configured to allow out-of-plane rotation for each of the plurality of chambers. In several embodiments, the out-of-plane rotation of each of the plurality of chambers is configured to move each of the plurality of chambers between a plurality of orientations. In several embodiments, each of the plurality of chambers moves between 180 degrees of rotation (whether in-plane or out of plane). In several embodiments, each of the plurality of chambers moves between orientations where each of the plurality of chambers lies along a plane of each of the plurality of arms.

In several embodiments, the systems disclosed herein further comprise at least one filter configured to prevent larger sized sample components from passing into and clogging the microfluidic chip. In several embodiments, the filter is attached to the sample chamber in order to filter the sample prior to having the sample pass into the microfluidic passageways of the microfluidic chip. In some embodiments, the filter is located upstream of or before the microfluidic chip and is configured to filter the sample to prevent clogging of the microfluidic chip. In some examples, the upstream filter can include a mesh that is configured to cut or micronize the tissue or tissue fragments to allow the sample to pass through the microfluidic chip without clogging. The cutting or micronization of the sample is configured to produce macroscopic aggregates for the purpose of microfluidic shearing in the microfluidic chips. In some embodiments, the filter is located downstream or after the microfluidic chip to only allow a certain sized sample to pass out of the device for collection.

Additional systems are also provided for herein. For example, there is provided a system for processing samples comprising a support plate, a motor, coupled to the support plate and configured to rotate the support plate; and at least one carriage arranged on the support plate, wherein the at least one carriage is configured to receive a microfluidic chip and at least one sample chamber for receiving a sample for processing, and wherein the at least one carriage is configured to rotate in a plane parallel to a plane of the support plate.

Further, there is provided a system for processing samples comprising a support plate, a motor, coupled to the support plate and configured to rotate the support plate, and at least one carriage arranged on the support plate, wherein the at least one carriage is configured to rotate in a plane parallel to a plane of the support plate, a microfluidic chip received within the at least one carriage, wherein the microfluidic chip includes a port and at least one microfluidic channel extending along a length of the microfluidic chip, and at least one sample chamber for receiving a sample for processing, the at least one sample chamber fluidly connected to the first port of the microfluidic chip and configured to allow the sample to flow from the at least one sample chamber and along the length of the microfluidic chip.

In several embodiments, the microfluidic chip has a length between about 10 mm and 100 mm. In several embodiments, the length of the at least one microfluidic channel is less than (or equal to) a length of the microfluidic chip. In several embodiments, the width and depth of the microfluidic channel is within the range of between 5 µm and 8 mm. It shall be appreciated that in several embodiments the microfluidic chip is removable.

The microfluidic channel can have a variety of configurations, depending on the embodiment, and the tissue to be processed. For example, in one embodiment, the microfluidic channel(s) has an hourglass configuration. In several embodiments, the at least one microfluidic channel comprises a first region comprising a stepwise taper that gradually decreases in width along a length of the at least one microfluidic channel, a constriction region, and a second region comprising a stepwise taper gradually increasing in width along a length of the at least one microfluidic channel. In additional embodiments, the at least one microfluidic channel has a series of regions of increasing width and regions of decreasing width. In several embodiments, the at least one microfluidic channel has a diamond pattern. In several embodiments, the at least one microfluidic channel includes a plurality of pockets, which are optionally fin-shaped. In several embodiments, the at least one microfluidic channel comprises a first region comprising a series of bifurcations and a second region wherein pairs of bifurcated channels are recombined. In additional embodiments, the at least one microfluidic channel comprises a plurality of wells, wherein the plurality of wells are configured to sort portions of the sample of a predetermined size.

Still additional methods are provided for herein, such as, for example, a method for processing samples comprising a sample in a sample chamber, inserting the sample chamber into at least one of a plurality of carriages, wherein the sample chamber is fluidly connected to a microfluidic chip comprising at least one microfluidic channel, wherein one of the plurality of carriages is attached to a support plate, the support plate configured to rotate about a first axis, and wherein the at least one of the plurality of carriages is configured to rotate about a second axis, the second axis parallel to the first axis, and rotating the support plate about the first axis, wherein the rotation is configured to drive the sample from the sample chamber through the at least one microfluidic channel in a first direction away from the sample chamber. In several embodiments, the method further comprises rotating the at least one of the plurality of carriages about the second axis into a second orientation. In several embodiments, the methods further comprise rotating the support plate about the first axis, wherein the rotation is configured to drive the sample through the at least one microfluidic channel in a second direction toward the sample chamber. Additionally, the methods optionally further comprise removing the sample chamber from the at least one of a plurality of carriages.

An additional system is provided, comprising a support plate including a plurality of arms, wherein the plurality of arms extends radially from the support plate, a motor, coupled to the support plate and configured to rotate the support plate, a plurality of carriages, wherein each of the plurality of carriages is arranged on one of the plurality of arms on the support plate, wherein each of the plurality of carriages is positioned co-axially about one of a plurality of axes, wherein each axis extends perpendicularly from the arm that the carriage is arranged on, wherein each of the plurality of carriages is configured to receive a microfluidic chip and at least one sample chamber for receiving a sample for processing, and wherein each of the plurality of carriages is rotatable about one of the plurality of axes, and, an encasement configured to receive the support plate, the encasement configured to protect a user form the system for processing samples, wherein the encasement includes an opening that is configured to provide access to the sample chamber. In several embodiments, the at least one sample chamber includes a vent and a vent channel that is fluidly connected to the interior of the sample channel, wherein the vent is configured to provide laminar flow through the sample chamber. In several embodiments, the at least one sample chamber includes an opening that is fluidly connected to the microfluidic chip. In several embodiments, the at least one sample chamber includes an inlet configured to allow the sample for processing to be inserted or removed from the at least one sample chamber. In one embodiment, the inlet is located opposite of the opening, though other positions may optionally be used. In several embodiments, the at least one sample chamber includes a one-way valve configured to ensure the sample stays inside the chamber during processing. In several embodiments, the interior of the sample chamber has a sloped, beveled, or otherwise shaped surface adjacent to the inlet, the surface configured to cause the sample to aggregate adjacent the inlet for easy removal of the sample after processing. In one embodiment, the vent is located on an opposite end of the sample chamber as the opening. In some embodiments, the inlet is configured to engage with a syringe, the syringe is configured to remove the sample and allow the sample to be injected directly into a target site.

In several embodiments, each of the plurality of chambers is retained in an opening of each of the plurality of arms, wherein each of the plurality of chambers extends through the opening of each of the plurality of arms. In such embodiments, each of the plurality of chambers is optionally retained along a plane of each of the plurality of arms. In several embodiments, each of the plurality of chambers is optionally retained in the opening of each of the plurality of arms with at least one pin that is configured to allow out-of-plane rotation for each of the plurality of chambers. In several such embodiments, the out-of-plane rotation of each of the plurality of chambers is configured to move each of the plurality of chambers between a plurality of orientations. In several embodiments, each of the plurality of chambers moves between 180 degrees of rotation (e.g., 0 to 45 degrees, 45-90 degrees, 90 to 135 degrees, 135 degrees to 180 degrees, etc.) In several embodiments, each of the plurality of chambers moves between orientations where each of the plurality of chambers lies along a plane of each of the plurality of arms. In several embodiments, the system further comprising a filter configured to prevent larger sized sample components from passing into and clogging the microfluidic chip. In one embodiment, the filter is attached to the sample chamber. In some embodiments, the filter is located upstream of or before the microfluidic chip and is configured to filter the sample to prevent clogging of the microfluidic chip. In some examples, the upstream filter can include a mesh that is configured to cut or micronize the tissue or tissue fragments to allow the sample to pass through the microfluidic chip without clogging. The cutting or micronization of the sample is configured to produce macroscopic aggregates for the purpose of microfluidic shearing in the microfluidic chips. In some embodiments, the filter is located downstream or after the microfluidic chip to only allow a certain sized sample to pass out of the device for collection.

In several embodiments, there is provided a system for processing samples comprising a support plate including a plurality of arms, wherein the plurality of arms extends radially from the support plate, a motor, coupled to the support plate and configured to rotate the support plate, a plurality of carriages, wherein each of the plurality of carriages is arranged on one of the plurality of arms on the support plate, wherein each of the plurality of carriages is positioned co-axially about one of a plurality of axes, wherein each axis extends perpendicularly from the arm that the carriage is arranged on, wherein each of the plurality of carriages is configured to receive a microfluidic chip and at least one sample chamber for receiving a sample for processing, and wherein each of the plurality of carriages is rotatable about one of the plurality of axes, an encasement comprising a body portion and a cover, wherein the body portion is configured to receive the processing system, and wherein the cover is disposed over the body portion and is configured to seal the processing system within the body portion and protects a user from the system for processing samples, a spin stand comprising a motor, an externally threaded rod attached to the motor, wherein rotation of the motor rotates the externally threaded rod, a plate comprising a plurality of engagement structures for retaining a syringe, wherein the plate is attached to a bearing having an internal thread, the internal thread configured to engage with the external thread of the rod, wherein rotation of the motor is configured to raise or lower the plate in a vertical direction, wherein the syringe comprises, a chamber having an opening configured to fluidly connect to the at least one sample chamber, and a plunger disposed within the chamber, wherein advancing and withdrawing the plunger evacuates and intakes the sample for processing, and wherein the plate retains a distal end of the plunger and movement of the plate in a vertical direction lower or raises the plunger within the chamber of the syringe to evacuate or intake the sample for processing.

In several embodiments, the rotary motor is attached to the cover of the encasement, while in other embodiments, the rotary motor is located external of the encasement. In several embodiments, the plate is circular, while in some embodiments, the plate comprises a ring attached to the bearing by a plurality of arms. In one embodiment, the plate comprises a central circular plate and a co-axial ring. In some embodiments, the engagement structures are hook shaped and are configured to allow insertion and removal of the distal end of a plunger. In several embodiments, the system comprises a plurality of spaced apart engagement structures to secure the syringe when it is attached to the at least one sample chamber on a first end of the microfluidic chamber or when it is attached to the at least one sample chamber on a second end of the microfluidic chamber. In several embodiments, each of the plurality of arms further comprises an engagement structure configured to engage with a corresponding structure located on each of the plurality of carriages to retain each of the plurality of carriages in a first orientation. In several embodiments, engagement structures are configured to release and engage the corresponding structure such that the carriage is configured to move between a plurality of orientations about one of the plurality of axes. In several embodiments, the engagement structures comprise magnets and the corresponding structure comprises a magnetically responsive material. Conversely, in several embodiments, the engagement structure comprises a magnetically responsive material and the corresponding structures are magnets. In certain embodiments, acceleration or deceleration forces are configured to move the carriage between the plurality of orientations. In several embodiments, the carriage comprises a gear assembly, the gear assembly is configured to move the carriage between the plurality of orientations. In several embodiments, the carriage comprises a centripetal ratchet, the centripetal ratchet configured to move the carriage between the plurality of orientations.

Methods are provided, such as a method for processing samples comprising providing a sample in at least one sample chamber, inserting the sample chamber into at least one of a plurality of carriages, wherein the sample chamber is fluidicly connected to a microfluidic chip comprising at least one microfluidic channel, wherein one of the plurality of carriages is attached to a support plate, the support plate configured to rotate about a first axis, and wherein the at least one of the plurality of carriages is configured to rotate about a second axis, the second axis parallel to the first axis, and securing a syringe to the sample chamber, wherein an opening of the syringe is fluidly connected to the sample chamber and a distal end of a plunger of the syringe is removably attached to a plate, wherein the plate is attached to a motor and is configured to be rotatable and movable in a vertical direction, and wherein movement of the plate in a vertical direction lowers or raises the plunger within a barrel of the syringe to evacuate or intake the sample for processing within the sample chamber, and rotating the support plate about the first axis, wherein the rotation is configured to drive the sample from the sample chamber through the at least one microfluidic channel in a first direction away from the sample chamber. In several embodiments, the method further comprises lowering the plate in a vertical direction such that the plunger is lowered within the barrel of the syringe to evacuate the sample for processing into the sample chamber. In such methods, there is optionally a step in which the plate is raised in a vertical direction such that the plunger is raised within the barrel of the syringe to remove the sample for processing from the sample chamber. In several embodiments, the method further comprises rotating the at least one of the plurality of carriages about the second axis into a second orientation.

In still additional embodiments, there is provided the use of a processed tissue sample for treatment of a medical condition. In several embodiments, the condition is diabetic ulcers. In several embodiments, the condition is one that is improved or benefits from activated cells, such as stem cells. In several embodiments, there is provided use of activated stem cells from adipose tissue that result from the processing methods and systems disclosed herein, for use in the manufacture of medicament for treating a disease or ailment.

DETAILED DESCRIPTION OF THE ILLUSTRATED EMBODIMENTS

Figure 1:
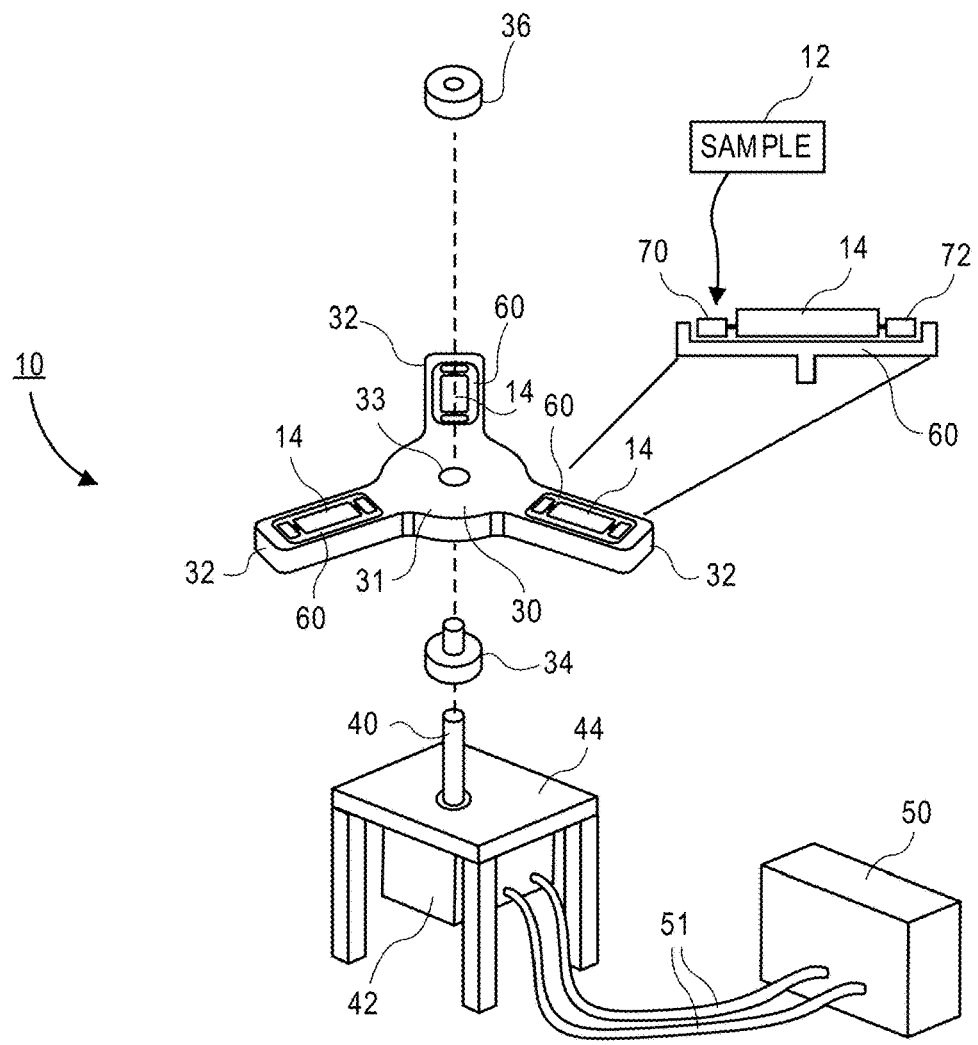
FIG. 1 illustrates an exploded view of one embodiment of a system for processing a sample using a plurality of rotatable microfluidic chips that are mounted on rotating support plate.

FIG. 1 illustrates a system 10 for processing a sample 12 according to one embodiment. The system 10 includes one or more microfluidic chips 14 that are used to process the sample 12 as described herein. The sample 12 may include, in one embodiment, a biological sample. For example, in one particular preferred embodiment, the sample 12 may include a tissue sample obtained from a mammalian organism such as fat or adipose tissue or tumor tissue. In another example, the sample 12 may contain cells that are then processed or run through the microfluidic chip 14. The sample 12 may, in another embodiment, include particles such as beads or the like. In yet another embodiment, the sample 12 may contain fluid one or more fluid reagents or reactants. In still a different embodiment, the sample 12 may contain water or a water-based sample.

Figure 2:
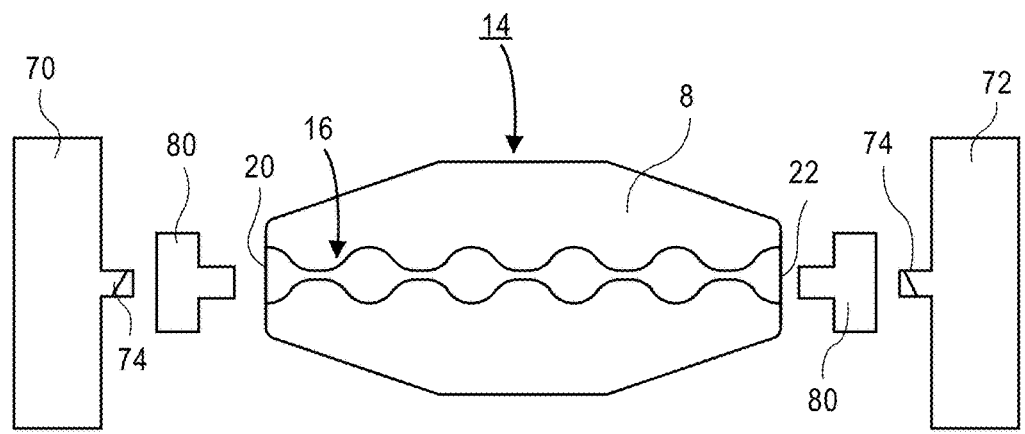
FIG. 2 illustrates one embodiment of a microfluidic chip along with an optional adapter and opposing, modular sample chambers.

In several embodiments, the microfluidic chip 14 includes one or more microfluidic channels 16 formed in a substrate 18 as seen, for example, in FIG. 2. The microfluidic chip 14 typically has a length (along longest side) between around 10 mm and 100 mm, for example about 10 to about 20 mm, about 20 to about 30 mm, about 30 to about 40 mm, about 40 to about 50 mm, about 50 to about 60 mm, about 60 to about 70 mm, about 70 to about 80 mm, about 80 to about 90 mm, about 90 to about 100 mm, and any lengths therebetween including endpoints. The one or more microfluidic channels 16 extend generally along the longitudinal (i.e., long) axis of the microfluidic chip 14 and traverses generally from one end of the microfluidic chip 14 to an opposing end of the microfluidic chip 14. In several embodiments, the length of microfluidic channel 16 is less than the total length of the microfluidic chip 14. The width and depth of the microfluidic channel 16 may fall within the range of about 5 μm to about 8 mm, depending on the embodiment. For example, the length (or width) can range from about 5 μm to about 10 μm, about 10 μm to about 20 μm, about 20 μm to about 50 μm, about 50 μm to about 100 μm, about 100 μm to about 200 μm, about 200 μm to about 500 μm, about 500 μm to about 750 μm, about 750 μm to about 1000 μm, about 1 mm to about 2 mm, about 2 mm to about 3 mm, about 3 mm to about 4 mm, about 4 mm to about 5 mm, about 5 mm to about 6 mm, about 6 mm to about 7 mm, about 7 mm to about 8 mm, and any dimensions therebetween, including endpoints. In additional embodiments, the ratio of length to width of the microfluidic channel ranges from about 1000:1, about 750:1, about 500:1, about 250:1, about 100:1, about 50:1, about 25:1, about 10:1, about 2:1, about 1:1, about 1:2, about 1:10, about 1:25, about 1:50, about 1:100, about 1:250, about 1:500, about 1:750, about 1:1000, and any ratio between those listed. In addition, in many microfluidic chip 14 designs, the width and depth vary due to the presence of constriction regions, expansion regions, and the like.

As seen in one non-limiting embodiment depicted in FIG. 2, a first port 20 is located at one end of the microfluidic chip 14 and serves as inlet (or outlet as explained herein) for the sample 12. A second port 22 is located at the other opposing end of the microfluidic chip 14. As explained herein, the one or more microfluidic channels 16 may be provided in any number of configurations.

The microfluidic chips 14 may be formed from any number of materials. For example, the microfluidic chip 14 may be formed using a polymer or plastic material (e.g., polycarbonate, poly(methyl methacrylate) (PMMA), polyoxymethylene, polylactic acid (PLA) or acrylonitrile-butadiene-styrene (ABS) material or the like). The microfluidic chips 14 may be formed using other materials such as metals (e.g., aluminum, steel, titanium, alloys, or the like). The microfluidic chips 14 may be made using one or more layers that are bonded together to form the fully enclosed microfluidic chip 14. The microfluidic chips 14 may thus be made as a laminate structure formed from one or more layers or substrates 18. For example, a first layer of the microfluidic chip 14 may be formed using polycarbonate or PMMA and may have the microfluidic channels 16 formed therein using CNC milling or laser etching (or chemical etching) with a second thin cover layer being bonded or otherwise adhered to the first layer to form the complete microfluidic chip 14. A double-sided pressure adhesive may be used to bond the two layers to one another. Bonding may also be accomplished using ultrasonic welding. Alternatively, the microfluidic chips 14 may be made from a monolithic substrate 18. The microfluidic chips 14 may be formed using any number of manufacturing processes including three dimensional (3D) printing, injection molding, CNC milling or laser etching.

Referring back to FIG. 1, the system 10 includes a support plate 30 that, in a preferred embodiment, has a plurality of arms or wings 32 that extend outwardly from a central region or hub 31 of the support plate 30. In alternative embodiments, the support plate is simply a disc with an inner portion and a lateral portion, the lateral portion in place of arms. In some embodiments, the arms or wings 32 are separate structures that are secured to the hub 31 using one or more fasteners (e.g., screws, bolts, or the like.). In other embodiments, the arms or wings 32 are integrated with the hub 31 as a unitary structure. The central region or hub 31 may be made from the same or different material used to form the arms or wings 32. For example, the central region or hub 31 may be formed from a metal or metallic material (e.g., aluminum, stainless steel, steel, etc.) or a polymer material such as plastic, poly(methyl methacrylate) (PMMA), polycarbonate, and the like. The arms or wings 32 may also be formed using a metal, metallic material, or polymer such as those materials usable with the central region or hub 31.

The support plate illustrated in FIG. 1 includes three (3) such arms or wings 32, although it should be appreciated that the support plate may include any number of arms 32 that is more than a single arm 32 (e.g., between one and ten arms). In a preferred embodiment of the invention, the support plate 30 is made so that the arms 32 extend radially from the central region of the support plate 30 and are symmetrically arranged about the support plate 30. For example, in the three (3) arm configuration, each arm 32 is oriented about 120° from each adjacent arm. In several embodiments, the arms can be hinged such that during operation the arms move in an arcuate pattern be positioned in a plane perpendicular or substantially perpendicular to the axis of rotation. The central region of the support plate 30 contains a hole or aperture 33 that is dimensioned to accommodate a rotating chuck 34 that passes through the hole or aperture 33. The support plate 30 is secured to the chuck 34 using a fastener 36. For example, the chuck 34 may be threaded and the fastener 36 is a screw, nut, clip, press fit, magnetic engagement, or the like that engages with the threads of the chuck 34 to lock support plate 30 securely to the chuck 34. Alternatively, the fastener 36 may include a pin, magnet, or the like. In addition, shaft of the chuck 34 may have geometric profile that matches or locks with the hole or aperture 33 of the support plate 30 to aid locking the two components together. Of course, any other type of fastener or lock can be used to secure the support plate 30 to the chuck 34. The chuck 34 is fixedly held to the drive shaft 40 of a motor 42 using a locking pin, screw, or the like (not shown). The motor 42 may include any number of types of motors in which the rotational speed of the drive shaft 40 can be adjusted. As one example, the motor 42 includes a brushless servo motor (e.g., Parker motor SM232BE, Parker Hannifin Corporation, Charlotte, N.C.), although it should be understood that a wide variety of motors 42 can be used. In another alternative embodiment, the support plate 30 and arms 32 may be incorporated into the chuck 34 itself. That is to say, the arms 32 that support the microfluidic chips 14 may extend from the chuck 34 as opposed to a separate support plate 30 that is placed on the chuck 34.

Figure 3:
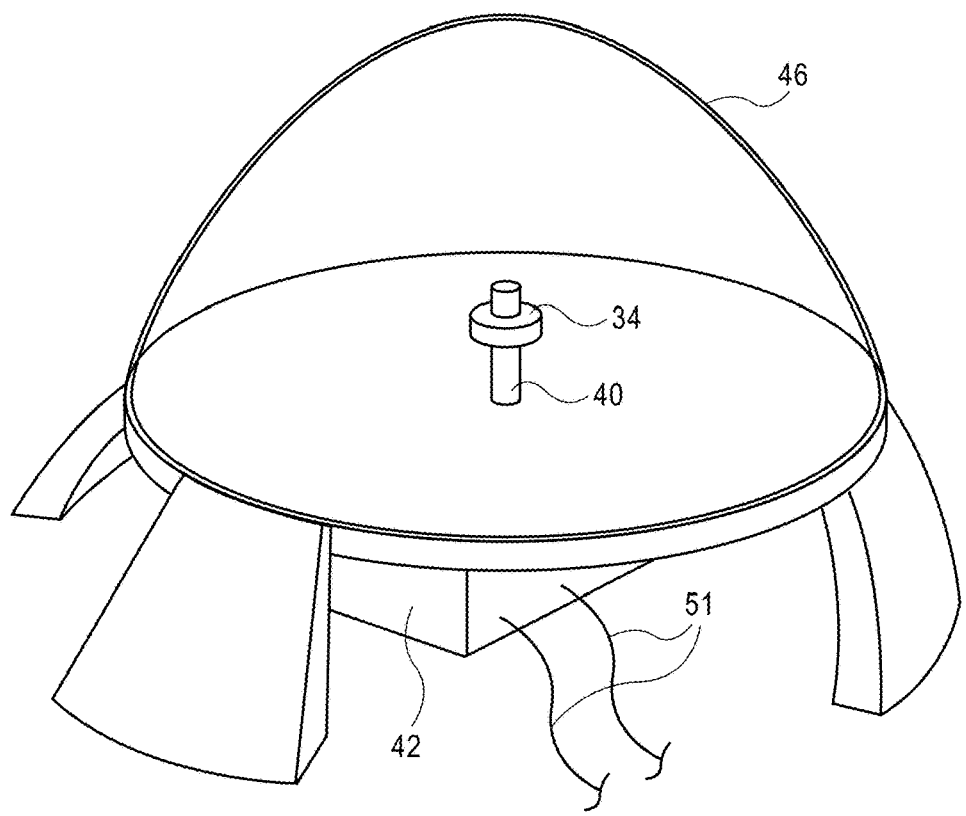
FIG. 3 illustrates one embodiment of an enclosure device that is optionally used with the systems and devices disclosed herein.

As seen in FIG. 1, the motor 42 is secured to a fixture 44 so that the drive shaft 40 and the chuck 34 mounted therein are in a substantially vertical orientation. In this orientation, the support plate 30 can be placed on top of the chuck 34 and locked thereto using the fastener 36. This arrangement places the support plate 30 in a substantially horizontal plane. When the motor 42 is actuated and rotates the drive shaft 40, the support plate 30 which is mounted thereon using the chuck 34 rotates about the axis of rotation of the drive shaft 40 in a substantially horizontal plane (rotation may be counterclockwise or clockwise (or both in an alternating pattern). With reference to FIG. 3, the mounted support plate 30 (and microfluidic chips 14 loaded thereon) may optionally be placed inside an encasement 46. The encasement 46 protects the operator from any dangers or failures that could occur while using the system 10. The encasement 46 can be made from any thick plastic material (example: polycarbonate, poly(methyl methacrylate; e.g., Plexiglass), etc.) or even metal (example: steel, aluminum, etc.). The encasement 46 may be opened and closed to provide access for mounting the support plate 30, etc. to the chuck 34. One or more portions may be made optically transparent so that the operations of the system 10 may be visually monitored. As an alternative to using a separate fixture 44 such as that shown in FIG. 1, the motor 42 may be mounted to the base or other structural support on the encasement 46 as seen in FIG. 3.

Figure 4:
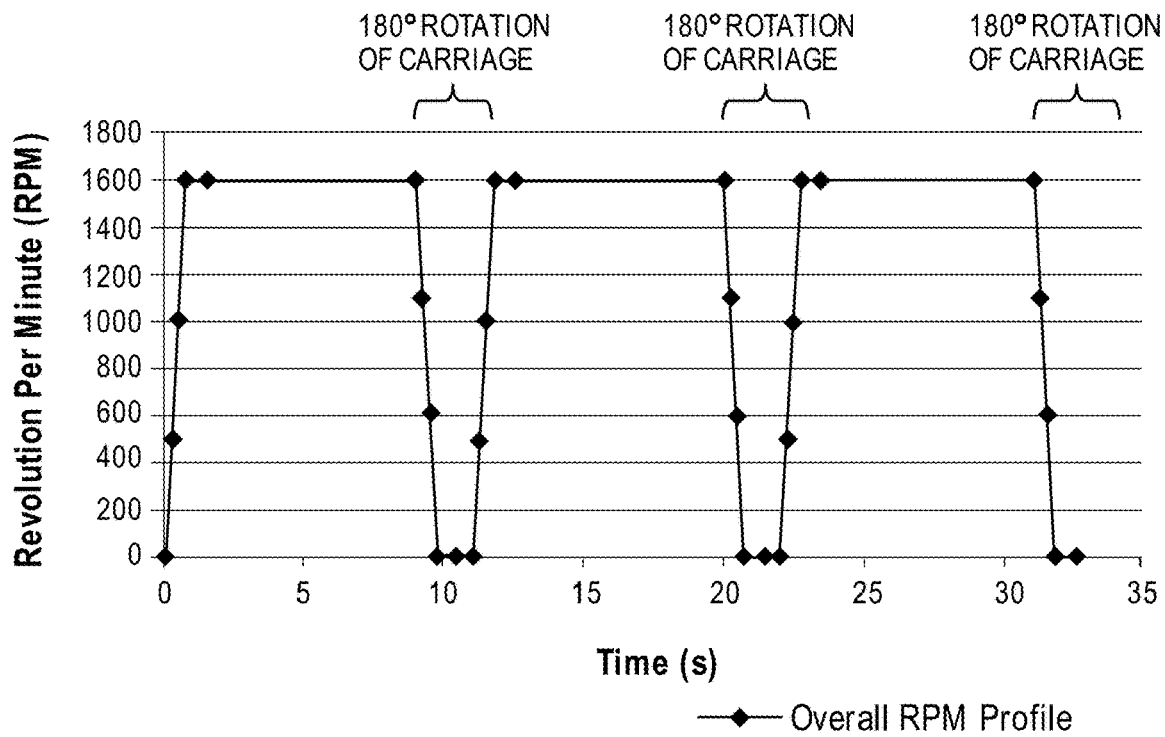
FIG. 4 illustrates an exemplary graph of the revolutions per minute (RPM) as a function of time for several cycles of rotating or spinning microfluidic chips for the systems and devices disclosed herein.

Referring back to FIG. 1, the motor 42 is connected to a controller 50 via one or more cables 51. As illustrated one cable 51 is used to drive the motor 42 while another cable 51 is used for feedback. The controller 50, which may be a stepper/servo controller 50, is used to drive the motor 42. The rotational speed or RPMs may be adjusted or programmed using the controller 50. In a preferred embodiment, the controller 50 may be programmed or loaded with a spin program that can spin the support plate 30 at a predetermined sequence of operations. For example, the controller 50 may ramp up the spin rate of the motor 42 to the desired RPM rate so that the sample 12 is passed through the one or more microfluidic channels 16 of the microfluidic chip(s) 14 and then, in one embodiment, decelerate the RPMs to rotate the microfluidic chips 14 through a half rotation or 180°. With the microfluidic chip(s) 14 now in flipped or reverse orientation, the controller 50 may then ramp up the RPMs again to the desired RPM rate to push or force the sample 12 again through the one or more microfluidic channels 16 of the microfluidic chip(s) 14 in the reverse direction. This process may be repeated for a plurality of cycles (e.g., ten to thirty 180° rotations of the microfluidic chip(s) 14; such as 10-15, 15-20, 20-25, 25-30 etc.). It shall be appreciated that greater or lesser numbers of cycles can be used, depending on, for example, the viscosity of the starting sample. FIG. 4 illustrates, for example, an exemplary rotational flow profile of the system 10 showing multiple cycles of 180° of the microfluidic chip(s) 14.

In one embodiment, the controller 50 can be programmed using software such as LabVIEW, Java, C, C++, Python or the like. The controller 50 may also be manually controlled. The actual rotational rate or RPM that is used may depend on the structure and configuration of the microfluidic chip 14. Typically, the RPM range is from 0 to about 10,000 RPM. Higher RPMs produce higher flow rates of the sample 12 through the microfluidic chip 14. Flow rates through the microfluidic chip 14 may vary but is generally within the range of about 0 mL/min to 700 mL/min. For example, flow rates can range from about 0.2 mL/min to about 1 mL/min, about 1 mL/min to about 2 mL/min, about 2 mL/min to about 10 mL/min, about 10 mL/min to about 50 mL/min, about 50 mL/min to about 100 mL/min, about 100 mL/min to about 250 mL/min, about 250 mL/min to about 500 mL/min, about 500 mL/min to about 700 mL/min and any rates therebetween (including endpoints). The upper limit of flow rates may be even greater depending on the rotational rate achieved using the motor 42.

FIG. 4 illustrates one illustrative flow profile that is used according to one embodiment. In this embodiment, the RPM rate is ramped up or accelerated (e.g., 2,000 RPMs/sec) to a maximum rotation rate of 1,600 RPMs over about a one second time period. An RPM rate of 1,600 is maintained for several seconds (e.g., about 8 seconds) and then rapidly decelerated (e.g., 2,000 RPMs/sec) which causes the microfluidic chip(s) 4 to rotate through 180°.

Figure 5:
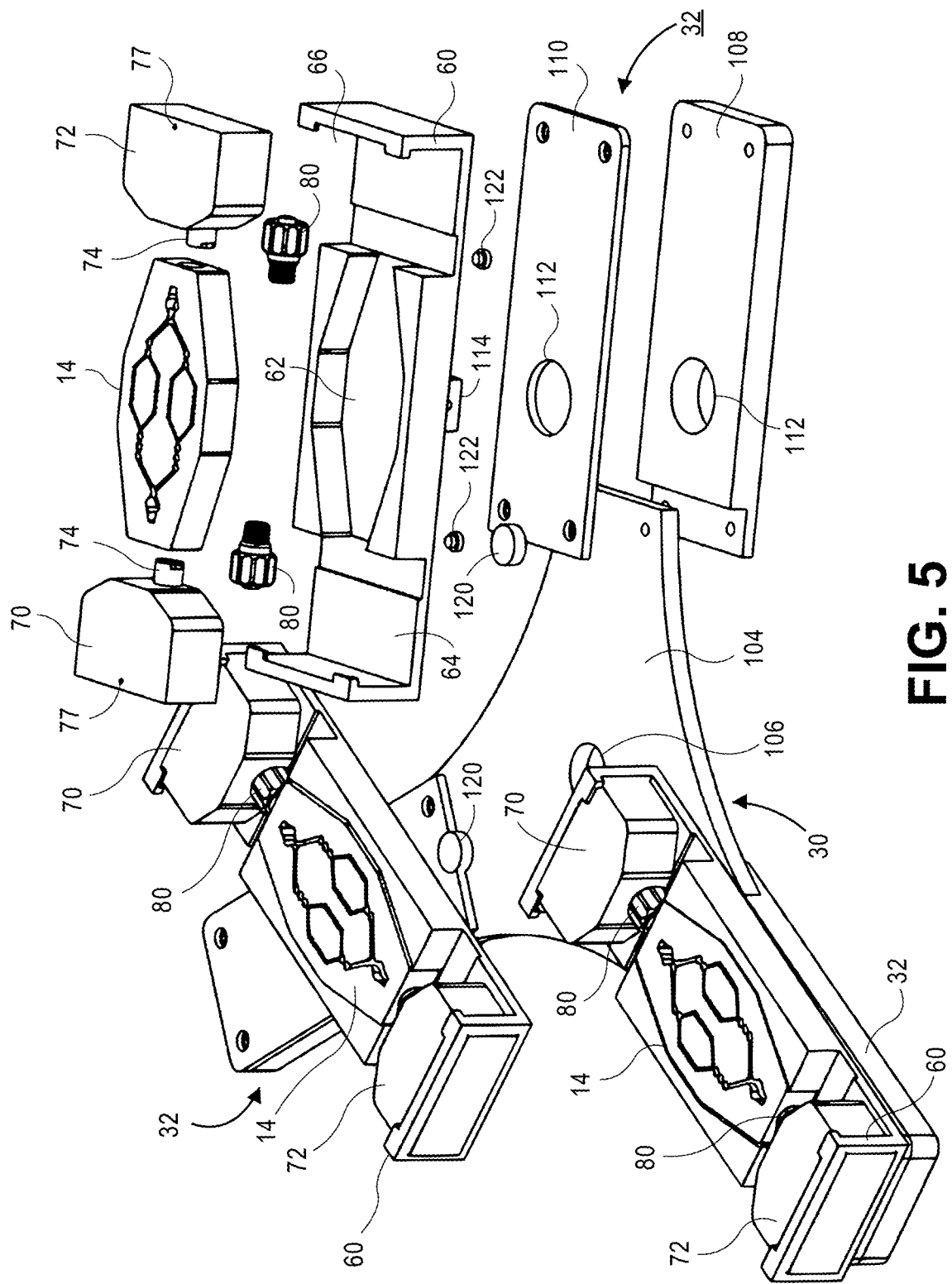
FIG. 5 illustrates a partially exploded view of one embodiment of a support plate having three arms that hold rotatable carriages and microfluidic chips therein.
Figure 6:
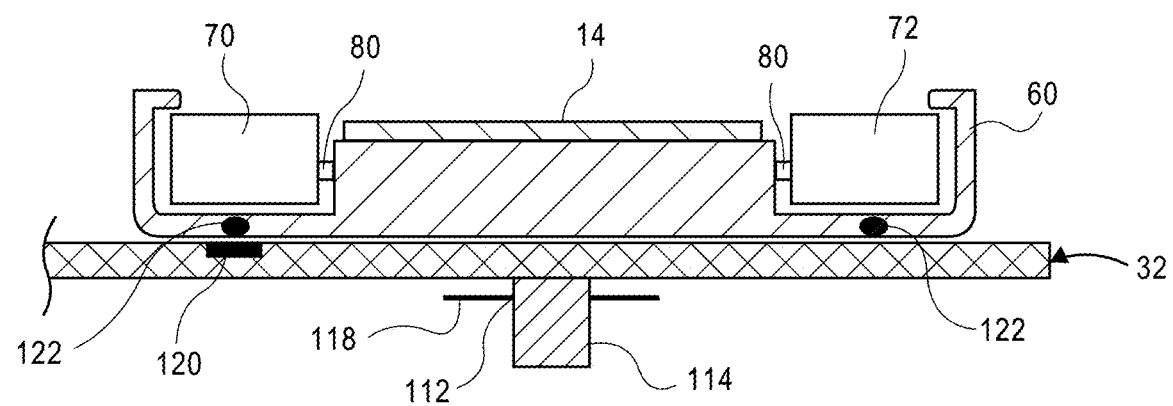
FIG. 6 is a side view of a single arm of the support plate of FIG. 5.

Referring back to FIG. 1 and FIG. 5, each microfluidic chip 14 is held or otherwise secured in a rotatable carriage 60. Each rotatable carriage 60 is rotatably mounted on an arm 32 of the support plate 30. The rotatable carriage 60 includes a recess 62 (seen in FIG. 5) that is dimensioned to accommodate the microfluidic chip 14 therein. The microfluidic chip 14 may be held therein by a friction fit, tabs, clips, detents, or the like. The rotatable carriage 60, in one embodiment, further includes a first end 64 and a second end 66 that are used to hold respective sample chambers 70, 72. Sample chamber 70 is located in the first end 64 while sample chamber 72 is located in the second end 66 of the carriage 60. Each sample chamber 70, 72 is fluidically coupled to the microfluidic chip 14 via the ports 20, 22 as seen, for example, in FIG. 2. Sample chamber 70 is fluidically coupled to the microfluidic chip 14 via the first port 20. Sample chamber 72 is fluidically coupled to the microfluidic chip 14 via the second port 22. Note that, optionally, the one or both of the sample chambers 70, 72 may be coupled to the microfluidic chip 14 using an adapter 80. The adapter 80 is illustrated in FIGS. 2, 5, and 6, and may include any number of designs and configurations. These include, by way of illustration and not limitation, Luer slip (e.g., slip tip connectors), Luer lock (e.g., rotating collar), etc. The adapter 80 may be formed using any number of materials including metals (e.g., aluminum, steel, stainless steel or the like) or polymer materials (e.g., plastic, polycarbonate, acrylates, resin materials, or the like).

Figure 7A:
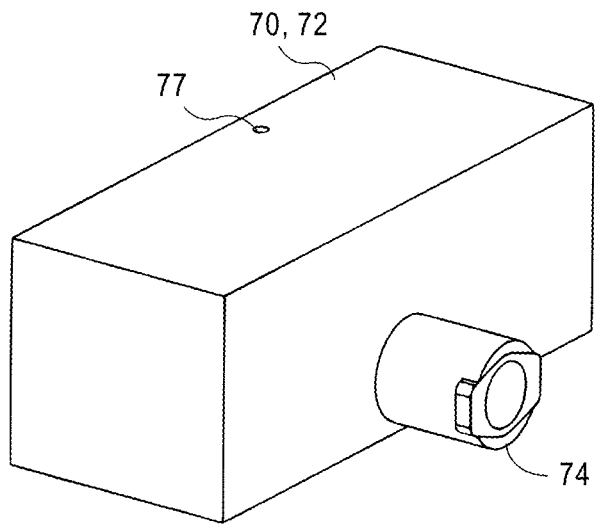
FIG. 7A illustrates a perspective view of a sample chamber according to one embodiment.
Figure 7B:
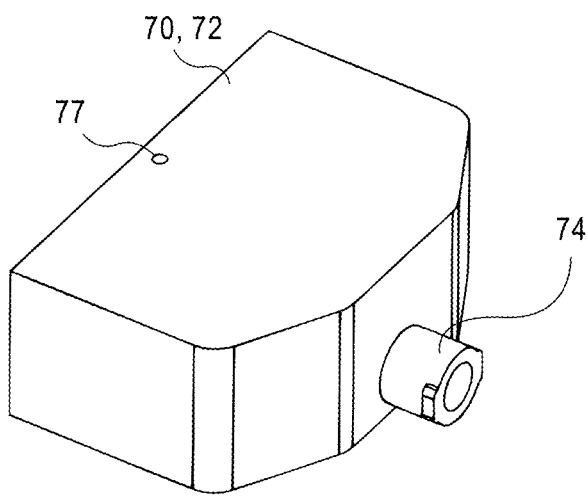
FIG. 7B illustrates a perspective view of a sample chamber according to one embodiment.
Figure 7C:
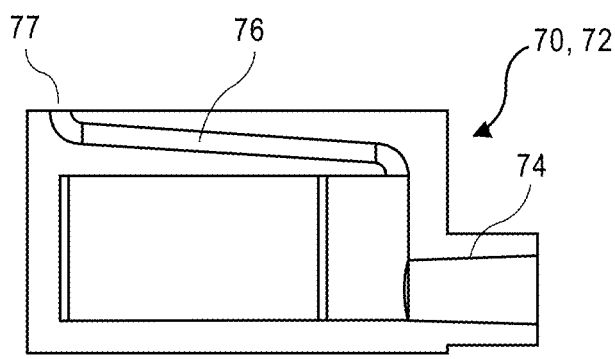
FIG. 7C illustrates a cross-sectional view of a sample chamber according to one embodiment.

One of the sample chambers 70, 72 is loaded with the sample 12 that is to be run through the microfluidic chip 14. The sample chambers 70, 72 are designed to hold a volume of sample 12 or other material that is to be processed through the microfluidic chip(s) 14. The holding volume for the sample chambers 70, 72 may range from >0 ml to ~100 ml and can be altered by changing the size of the chamber dimensions. For example, in several embodiments, the sample chamber volume can range from about 1 ml to about 3 ml, about 3 ml to about 5 ml, about 5 ml to about 10 ml, about 10 ml to about 25 ml, about 25 ml to about 50 ml, about 50 ml to about 75 ml, about 75 ml to about 100 ml, or any volumes therebetween, including endpoints. In one embodiment of the invention, the sample chambers 70, 72 are loaded with the sample 12 or other material that is run through the microfluidic chip 14. With reference to FIGS. 7A-7C, the sample chamber 70, 72 is designed with an adapter head 74 that be any type of syringe adapter head such as Luer slip (e.g., slip tip connectors), Luer lock (e.g., rotating collar), or the like. The sample chamber 70, 72 is also designed with a vent channel 76 as seen in FIG. 7C that can range from 0 mm to about 10 mm (e.g., about 1 mm to about 2 mm, about 2 mm to about 4 mm, about 4 mm to about 6 mm, about 6 mm to about 8 mm, or about 8 mm to about 10 mm) in diameter to allow laminar flow through the microfluidic chip 14 and not turbulent flow. Multiple vents can be used, depending on the embodiment. The vent channel 76 vents to the atmosphere and; in one embodiment, exits near an end of the sample chamber 70, 72 via vent hole 77 (FIGS. 7A-7C) and connects to the interior of the sample chamber 70, 72 near the adapter head 74 as seen in FIG. 7C. Optionally, a small filter can be placed in the vent hole 77 or otherwise communicate with vent hole 77 to prevent contamination or leaks. The sample chambers 70, 74 can be made from one or more of multiple materials such as resin material, plastic, or metal. These can be manufactured by any number of common manufacturing methods such as injection molding, resin printing (e.g., 3D printing), blow molding, machining, etc. In one embodiment, to fill the sample chamber 70, 72, the end or tip of a syringe (without needle) is inserted into the adapter head 74 located on the sample chamber 70, 72 and the syringe plunger is depressed to fill the chamber volume with sample 12 or material contained in the barrel of the syringe. The sample chambers 70, 72 are preferably modular components that can be inserted and/or removed from the ends 64, 66 of the carriage 60 as seen in FIG. 5. For example, the chamber 70 may be loaded outside of the device or system 10 and then inserted into the end 64 of the carriage 60.

In another embodiment as illustrated in FIGS. 8A-8D, a syringe chamber 86 is used as the sample chambers 70, 72 and can be placed in one or both ends 64, 66 of the carriage 60. The ends 64, 66 are designed to accommodate the length of the syringe chamber 86. This embodiment is particularly advantageous as it permits the physician to use the syringe chamber 86 directly after processing. For example, if adipose or fat tissue is processed using the system 10 described herein, the resulting processed tissue is loaded into the syringe chamber 86 which can easily be removed from the system 10 and used to directly inject the processed fat into the site of application on the subject. In this regard, the system 10 uses one or more onboard syringe chambers 86 instead of sample chambers 70, 72. Once processing is complete, the syringe chamber 86 is removed, a needle is added to the end and the now processed sample is optionally injected into a subject.

Figure 8A:
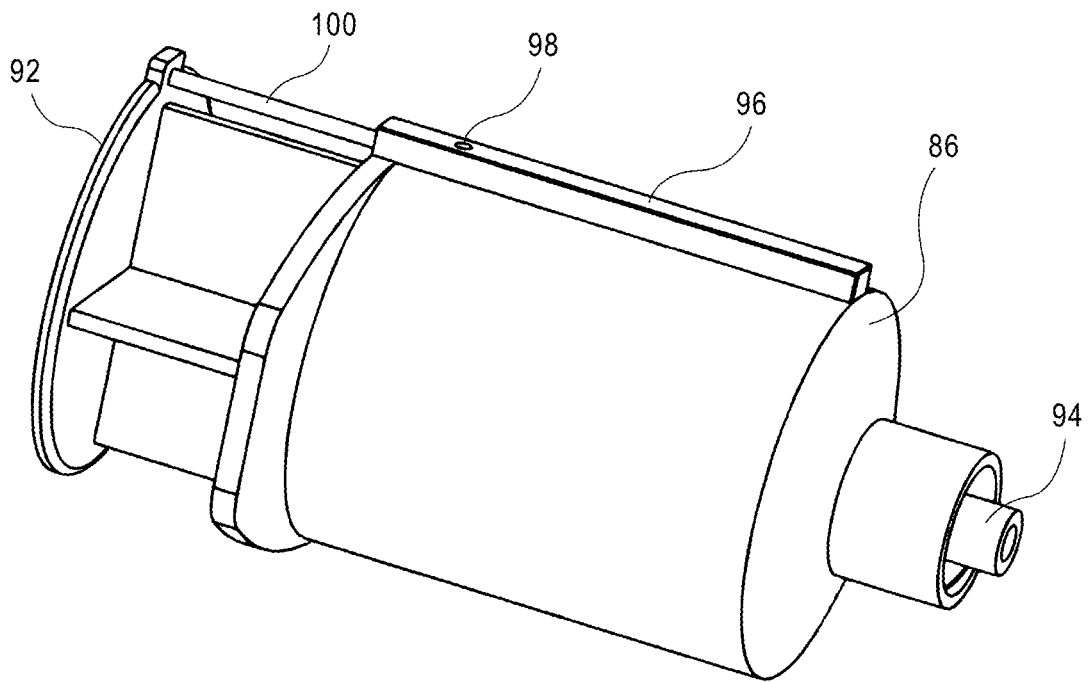
FIG. 8A illustrates a perspective view of a sample holder in the form a syringe that can be loaded into the carriage.
Figure 8B:
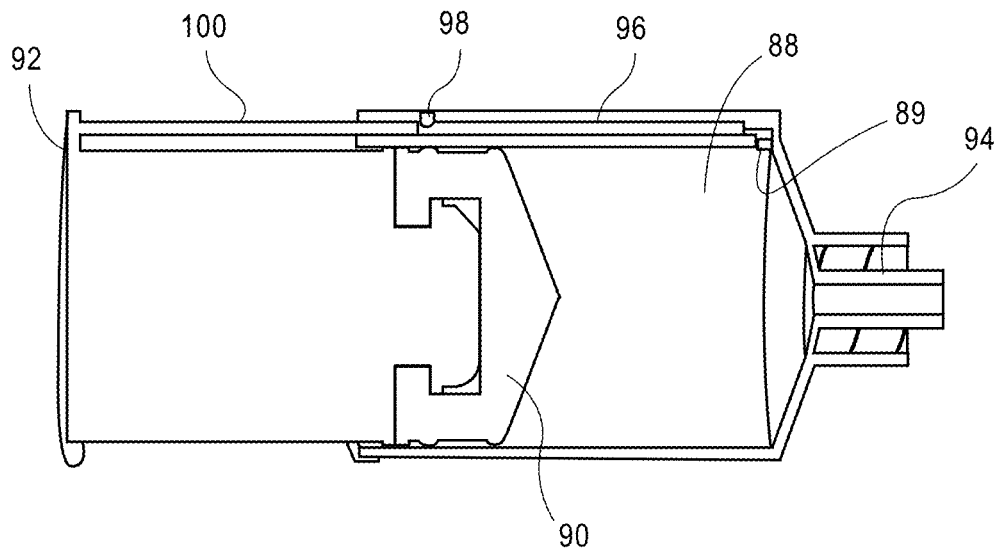
FIG. 8B illustrates a cross-sectional view of the syringe of FIG. 8A.

The syringe chamber 86 includes a syringe barrel 88 that defines the three-dimensional volume that holds the sample. A standard plunger 90 that includes a rubber or polymer seal is disposed in the barrel 88 and includes a proximal depressor 92 that is used to advance the plunger 90. An end of the syringe barrel 88 includes an adaptor end 94 that may include Luer slip (e.g., slip tip connectors), Luer lock (e.g., rotating collar), etc. that interfaces with the microfluidic chip 14. In one embodiment, the syringe chamber 86 is coupled to a vent channel 96 that extends along a length of the barrel 88 and communicates with the interior of the barrel 88 via hole 89 and terminates in a vent hole 98 (best seen in FIG. 8B) that is open to the atmosphere. The vent channel 96 permits venting and allows steady laminar flow through the syringe barrel 88 and the microfluidic chip 14. In one embodiment, a smaller, secondary syringe plunger 100 that includes a rubber or polymer seal is disposed in the vent channel 96 and is moveable therein to selectively open/close the vent channel 96. Specifically, when the seal of the secondary syringe plunger 100 is located proximal with respect to the vent hole 98, as seen in FIG. 8B, the vent channel 96 is open and the interior of the syringe barrel 88 can vent to atmosphere. However, when the seal of the secondary syringe plunger 100 is located distal with respect to the vent hole 98, the vent channel 96 is closed and the interior of the syringe barrel 88 is not vented; with the syringe chamber 86 acting as a standard syringe. The secondary syringe plunger 100 may be coupled to the same proximal depressor 92 so that movement of the depressor 92 will cause movement of both the plungers 90, 100. The syringe chamber 86 and other components such as the depressor 92 may be made from any number of materials including polymer materials such as resin, plastics or the like. Conventional manufacturing techniques such as injection molding, resin printing, or the like may be used. The syringe chamber 86 may also be formed from metals or a metallic material.

With reference now to FIGS. 5 and 6 one particular embodiment of a support plate 30 is disclosed. In this embodiment, the support plate 30 is formed using a center plate 104 that has a plurality of arms 32 that are secured to the center plate 104. The center plate 104 includes a hole or aperture 106 that is dimensioned to accommodate the chuck 34 (see FIG. 1). Each arm 32 in this embodiment is formed with a lower plate 108 and an upper plate 110. The lower plate 108 and the upper plate 110 may be secured to one another using any number of fasteners such as screws, bolts, or the like. The plates 108, 110 include a hole or aperture 112 formed therein that is aligned and dimensioned to accommodate a post 114 that extends from the carriage 60. The post 114, as best seen in FIG. 6, extends through the hole 112 in the lower plate 108 and the upper plate 110 and projects some distance below the arm 32. The post 114 includes a hole 116 that passes through the post 114 and receives a pin or clip 118 that is used to secure the carriage 60 to the arm 32 (yet still allow for rotation or spinning).

In this embodiment, a magnet or magnetic element 120 is disposed in the support plate 30 which may include the center plate 104 as illustrated in FIG. 5. As seen in FIGS. 5 and 6, two smaller magnets or magnetic elements 122 are disposed on a lower surface of the carriage 60 (or incorporated into the carriage 60 structure) and are used to temporarily hold the carriage 60 in one of two 180° configurations in which the longitudinal axis of the carriage 60 is aligned along the radial length of the arm 32. For example, the magnetic elements 122 located in the carriage 60 may include an actual magnet (e.g., rare earth magnet or other type) or it may include a magnetically susceptible screw, bolt, or piece of metal. The carriage 60, as explained herein, is able to switch back-and-forth between two 180° orientations so that the sample 12 can flow through the microfluidic chip 14 in forward or reverse directions. As explained herein, a number of different modalities may be used to switch the carriage 60 between these two orientations. This includes using a decelerating or accelerating force to switch the orientation of the carriages 60. Alternatively, an electromagnet that is disposed in the arm 32 may be used to toggle the carriage 60 (and microfluidic chip 14) between these two orientations. In yet another alternative embodiment, a gear assembly may be used in connection with a radial set of gear teeth that is able to turn the carriages 60 between the 180° orientations. Still another alternative embodiment uses a centripetal ratchet to mechanically rotate the carriage 60 into the different orientations based on a reduction of RPMs of the support plate 30. A still another alternative embodiment may replace the ratchet with a piston or shock-absorber like device.

Figure 9:
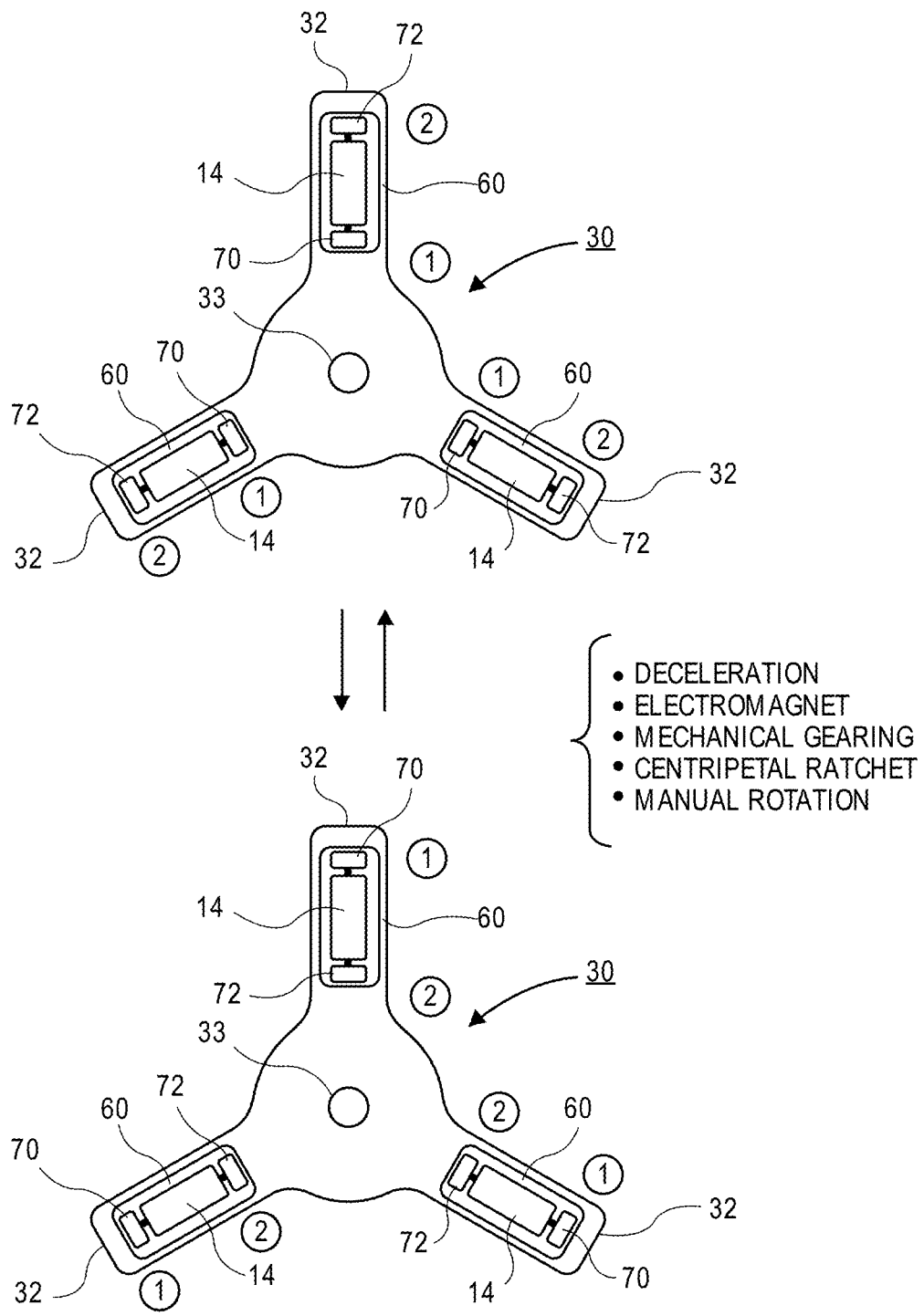
FIG. 9 illustrates a top down plan view of an embodiment of a support plate having three arms with rotatable carriages mounted thereon; each containing respective microfluidic chips. The carriages and microfluidic chips are illustrated rotating or spinning through 180°.

FIG. 9 schematically illustrates a support plate 30 having three different arms 32 each containing a rotatable carriage 60 that contains a microfluidic chip 14 therein. In the top or upper view, the rotatable carriages 60 are each oriented to have a first end (①) located radially inward on the arm 32 and with a second end (②) located radially outward on the arm 32. In this configuration, in response to rotation of the support plate 30, sample 12 or other material is run through the microfluidic chips 14 in a radially outward direction. That is to say, for a sample 12 starting in sample chamber 70, the sample 12 moves from the sample chamber 70 and into the microfluidic chip 14 and advances into sample chamber 72. Next, the carriages 60 with their respective microfluidic chips 14 are rotated through 180° to reverse the orientation of the carriages 60 and their microfluidic chips 14 as seen in the lower portion of FIG. 9. In this configuration, the first end (①) is located radially outward on the arm 32 with a second end (②) located radially inward on the arm 32. The sample 12 that was in sample chamber 72 is now located radially inward and rotation of the support plate 30 now causes the sample 12 to move from the sample chamber 72 and into the microfluidic chip 14 and advances further into sample chamber 70. This process may be repeated for any number of cycles.

In the embodiment of FIGS. 5 and 6, deceleration of the support plate 30 applies a force on the carriage 60 which breaks the force between the magnets 120, 122 causing the carriage 60 to rotate about the post 114 and reorient the carriage 60 180° whereby the opposing magnet 122 then is attracted to the other magnet 120 and fixes the carriage 60 in the new orientation. The support plate 30 is then accelerated again to move the sample 12 through the microfluidic chip 14 in the reverse flow direction; whereby the process of spinning the carriages 60 and their respective microfluidic chips 14 can be performed again.

Figure 10A:
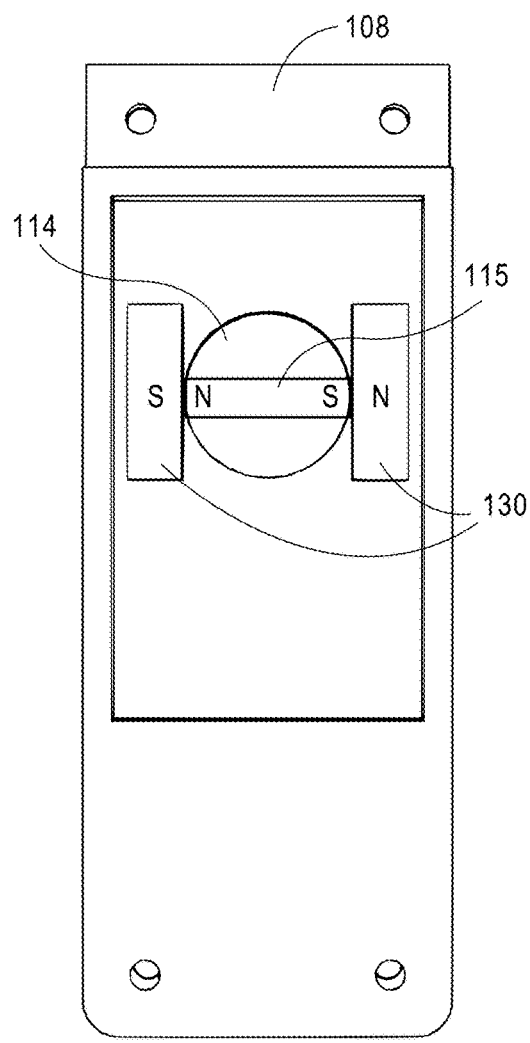
FIG. 10A illustrates one embodiment of a lower plate or housing that incorporates an electromagnet for turning the carriage and microfluidic chip.

With reference to FIG. 10A, in one alternative embodiment, an electromagnet 130 that is mounted on the lower plate 108 is used to spin or rotate the carriages 60 through 180°. The electromagnetic 130 may be powered using on-board batteries or wires delivered through the shaft 40. In this embodiment, the post 114 contains a magnet 115 that creates opposing magnetic poles on opposing sides of the post 114. The electromagnet 130 also includes two magnetic poles as illustrated and, when actuated, forces the post 114 to rotate such that the North pole of the electromagnet 130 is adjacent to the South pole of magnet 115. Conversely, the South pole of the electromagnet 130 is adjacent to the North pole of the magnet 115. The carriage 60 is rotated by reversing the polarity of the electromagnet 130.

Figure 10B:
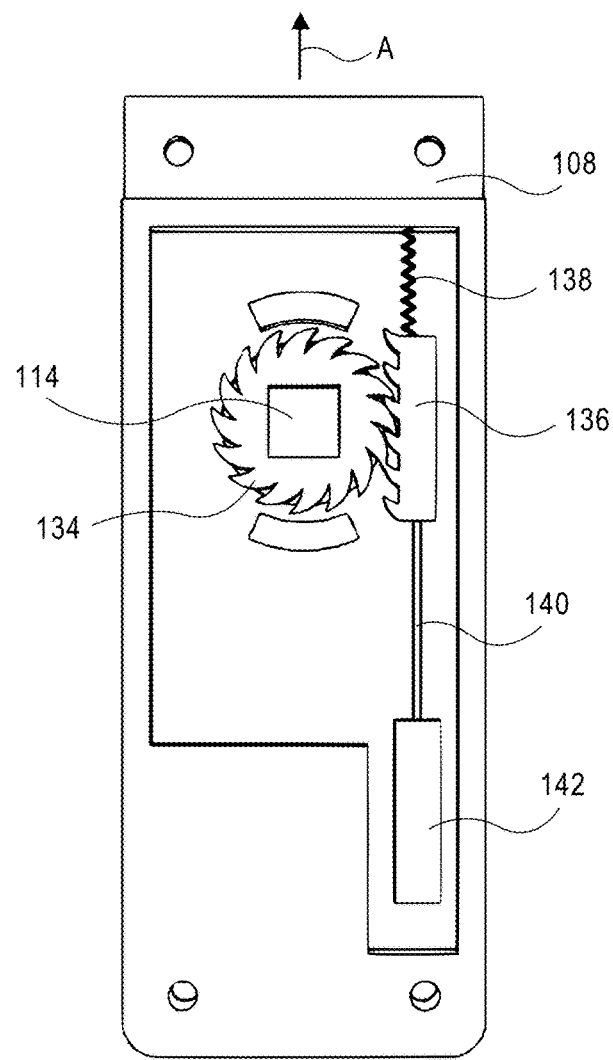
FIG. 10B illustrates one embodiment of a lower plate or housing that incorporates a centripetal ratchet for turning the carriage and microfluidic chip.

FIG. 10B illustrates yet another embodiment in which a centripetal ratchet is used to spin or rotate the carriage 60. In this embodiment, the lower plate 108 contains a ratcheting gear or wheel 134 that is secured to the post 114. The ratcheting gear 134 interfaces with a set of ratcheting teeth 136 that is connected at one end to a spring 138. The spring 138 is fixedly secured at the opposing end to the lower plate 108. The opposing end of the ratcheting teeth 136 is connected to a filament, line, cable, or string 140 that is coupled to a weight 142. During operation of the system 10, as the support plate 30 rotates, centripetal force causes the weight 142 to move radially outward on the lower plate 108 whereby the spring 138 extends to accommodate this force. Notably, the ratcheting teeth 136 do not move the ratcheting gear 134 during this operation because of the orientation of the teeth. When the support plate 30 decelerates or stops, the tensioning force of the spring 138 pulls the ratcheting teeth 136 (and weight 142) radially inward (in direction of arrow A) whereby the ratcheting teeth 136 now engage with the ratcheting gear 134 and cause rotation of the post 114. The rotation of the post 114 causes the carriage 60 to rotate through 180°.

Figure 11:
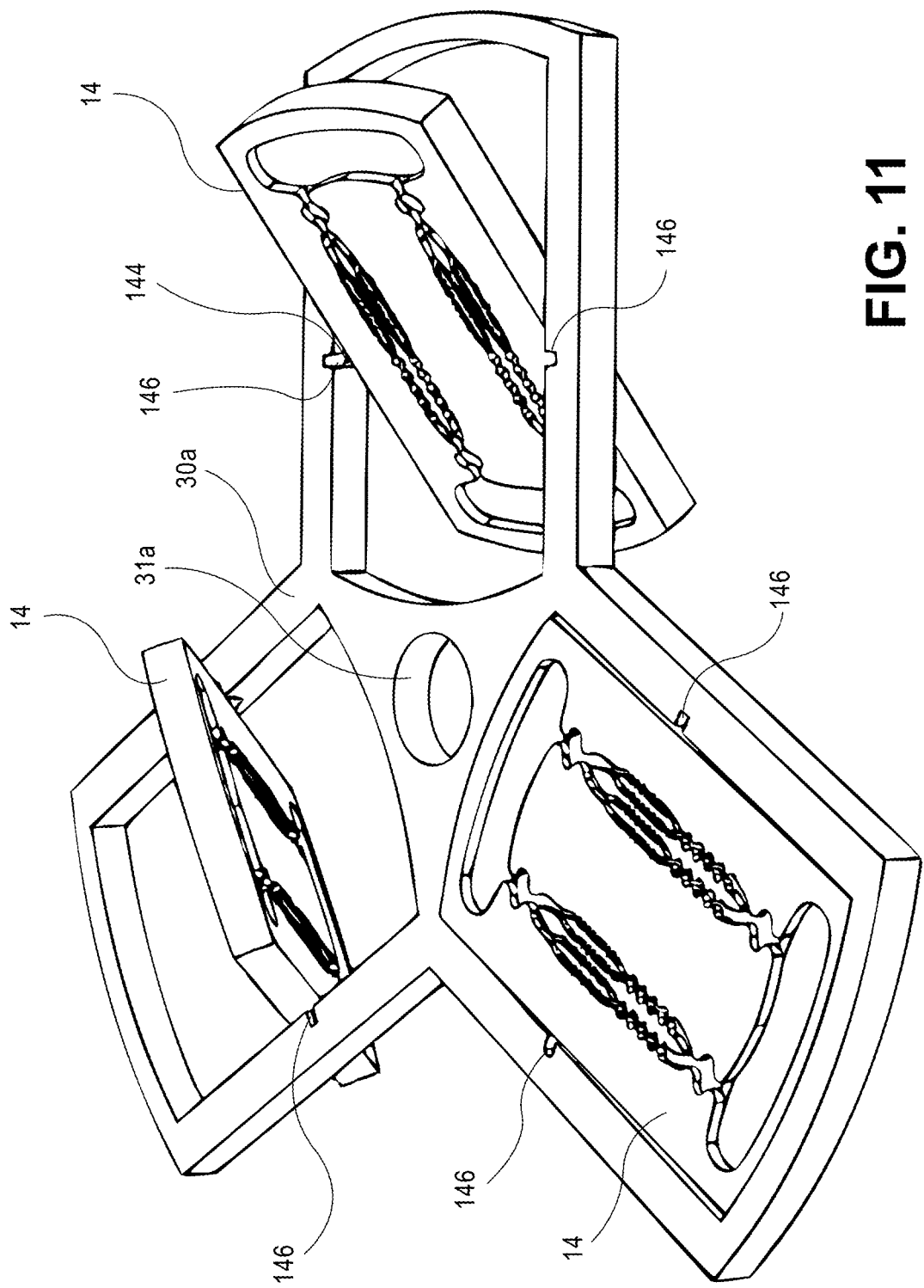
FIG. 11 illustrates another embodiment of a support plate that utilizes out-of-plane flipping of the carriages and/or microfluidic chips.

FIG. 11 illustrates another embodiment of a support plate 30a that includes a central hole or aperture 31a. In this embodiment, rather than have the microfluidic chips 14 rotate in a horizontal plane that is generally parallel to the plane of the support plate 30, the microfluidic chips 14 flip out-of-plane (e.g., perpendicular to the radial plane in which the arms lie) with respect to the rotational plane of the support plate 30. In this embodiment, the microfluidic chips 14 may include pins 144 that engage with slots 146 located on the support plate 30 that enable out-of-plane rotation. Note that in this embodiment; carriages 60 may be provided that hold the microfluidic chips 14 that can be rotated in a similar manner to the microfluidic chips 14 illustrated in FIGS. 5 and 6.

Figure 12A:
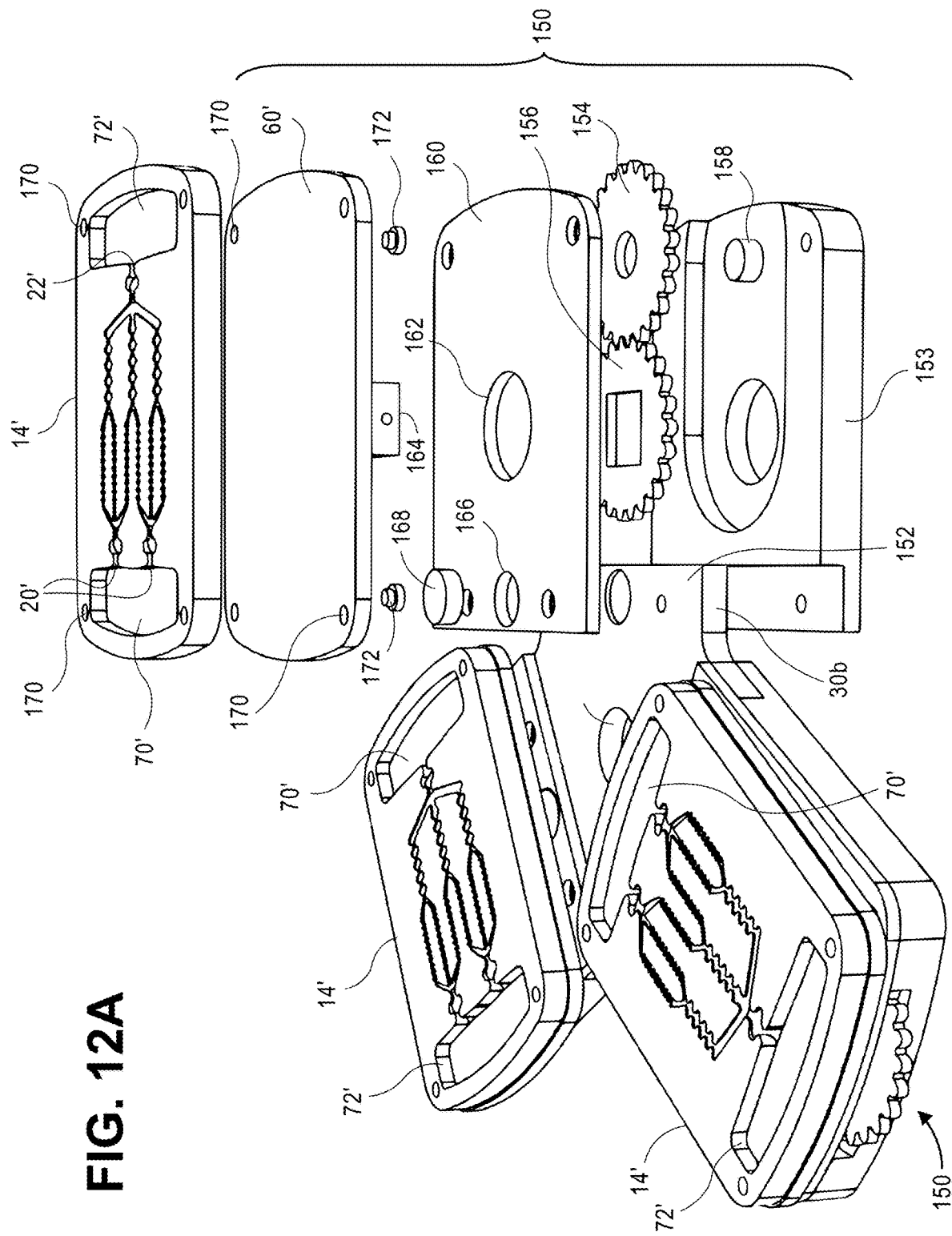
FIG. 12A illustrates a partially exploded view of another embodiment of a support plate having three arms that hold rotatable carriages and microfluidic chips therein. This embodiment incorporates gear assembles along with an exposed gear that engages with a geared or toothed surface to cause rotation of the carriages and microfluidic chips.

FIG. 12A illustrates another embodiment of a support plate 30b. In this embodiment, the support plate 30b has a central aperture or hole 33 that is used to support the support plate 30 the chuck 34 as described herein. The support plate 30b supports several gear boxes or gear assemblies 150 as seen in FIG. 12A that effectively function as the arms 32 of the support plate. In this embodiment, there are three such gear assemblies 150 with each gear assembly 150 being secured to a central hub 152 of the support plate 30b as seen in FIG. 12A using aluminum screws or the like (not shown). The gear assembly 150 includes a bottom housing 153 that holds two gears 154, 156. The outer gear 154 rotates about a post 158 located in the bottom housing 153 and is position such that a portion of the teeth of the gear 154 are exposed beyond the radial edge of the gear assembly 150. In this regard, the teeth of the gear 154 can be engaged with another gear or geared surface (seen in FIG. 12B) to cause this outer gear 154 to rotate. A second inner gear 156 is mechanically engaged to the outer gear 154. This inner gear 156, as explained herein, is used to rotate the carriage 60' containing the microfluidic chip 14'.

Figure 12B:
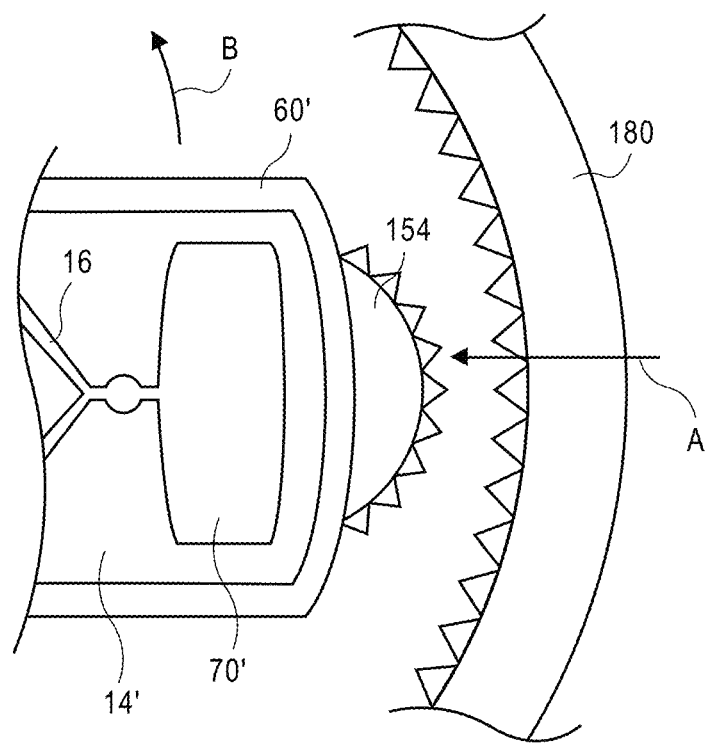
FIG. 12B illustrates a top down plan view of a geared or toothed surface interfacing with an exposed gear extending from a gear assembly on one of the arms of the support plate.

As seen in FIG. 12A, there is a top cover 160 to the gear assembly 150. The top cover 160 includes an aperture 162 therein where a shaft or post 164 connected to the carriage 60' passes through and mechanically connects to inner gear 156. Another aperture 166 is formed in the top cover 160 that is dimensioned to receive magnet 168 (e.g., rare earth magnet or other type). The magnet 168 is fixedly secured in this aperture 166 and the partial recess formed in the support plate 30. The magnet 168 is used to hold the orientation of the microfluidic chip 14' in one of two orientations during rotation of the carriage 60' (until the microfluidic chip 14' is rotated 180°). The carriage 60' is dimensioned to hold the microfluidic chip 14' thereon. The microfluidic chip 14' and carriage 60' have holes 170 in the corners such that the microfluidic chip 14' can be secured to the carriage 60' using removable fasteners (e.g., screws or the like); although the microfluidic chips 14' may be secured using any other type of fastener. In addition, on the underside of the carriage 60' there are two locations that receive magnetic screws 172 (e.g., steel screws). These screws 172 are used to hold the carriage 60' (and microfluidic chip 14') in one of two orientations during rotation of the support plate 30b. To rotate the carriages 60' of the embodiment, as seen in FIG. 12B, a surface having gear teeth 180 is brought (as seen by arrow A) into contact with the outer gear 154 while the support plate 30' is rotated (the support plate 30' may be rotated at a reduced speed for this operation). Rotation of the support plate 30' moves the gear 154 across the stationary surface (e.g., in the direction of arrow B) with gear teeth 180 causing the gear 154 to rotate and effectuate rotation of the carriage 60'. In the embodiment of FIG. 12A and 12B, the microfluidic chip 14' includes sample chambers 70', 72' that are formed directly inside the microfluidic chip 14'. In this embodiment, the ports 20, 22' at the end of the one or more microfluidic channels 16' lead to respective on-chip sample chambers 70', 72'.

Figure 13:
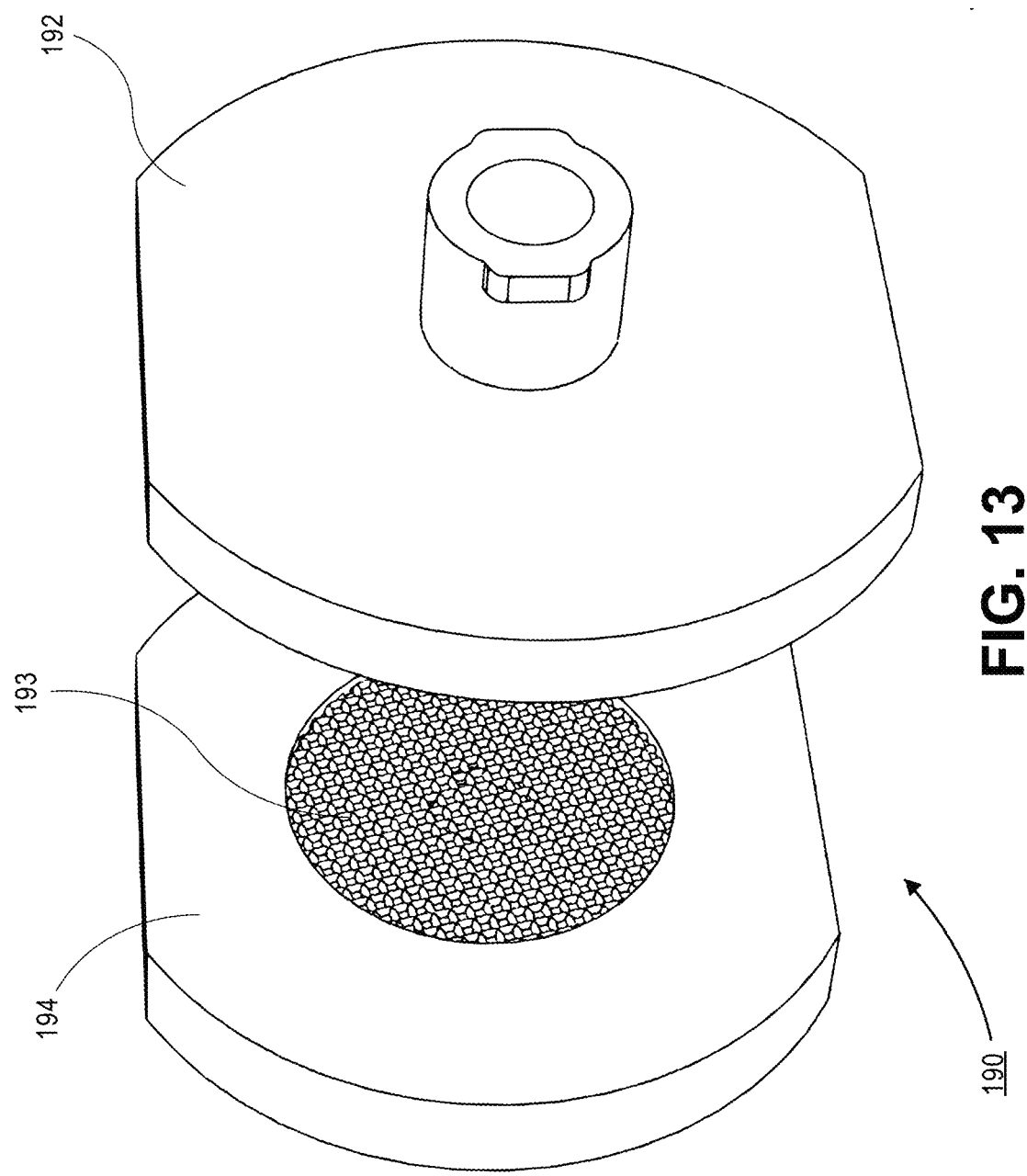
FIG. 13 illustrates a perspective view of one embodiment of an optional filter element.

FIG. 13 illustrates an optional filter element 190 that may be incorporated into the systems 10 described herein. The filter element 190 is used to keep larger sized sample components from passing into the microfluidic channels 16 and clogging them. The filter element 190 uses a grid-like filter pattern or mesh 193. In one embodiment, the filter is made up an end piece 192 (or top) that can have any kind of syringe attachments such as Luer slip (e.g., slip tip connectors), Luer lock (e.g., rotating collar), etc. Another end piece 194 that incorporates a mesh 193 therein is sealed against the opposing end piece 192 for form the complete filter element 190. The end piece 194 may also have any kind of syringe attachments such as Luer slip (e.g., slip tip connectors), Luer lock (e.g., rotating collar), etc. In some embodiments, the filter element 190 is located upstream of or before the microfluidic chip 14. 14' and is configured to filter the sample to prevent clogging of the microfluidic chip 14, 14'. In some examples, the upstream filter element 190 can include a mesh that is configured to cut or micronize tissue or tissue fragments to allow the sample to pass through the microfluidic chip 14, 14' without clogging. The cutting or micronization of the sample is configured to produce macroscopic aggregates for the purpose of microfluidic shearing in the microfluidic chips 14, 14'. In some embodiments, the filter element 190 is located downstream or after the microfluidic chip 14, 14' to only allow a certain sized sample to pass out of the device for collection.

Figure 14A:
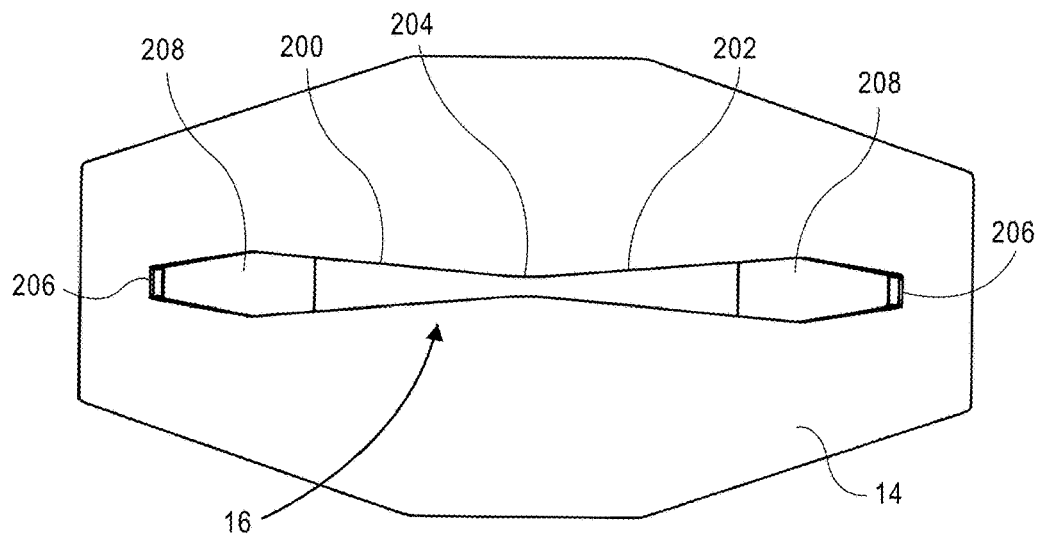
FIGS. 14A-14J illustrate different non-limiting embodiments of the microfluidic channel(s) contained in the microfluidic chips disclosed herein.
Figure 14B:
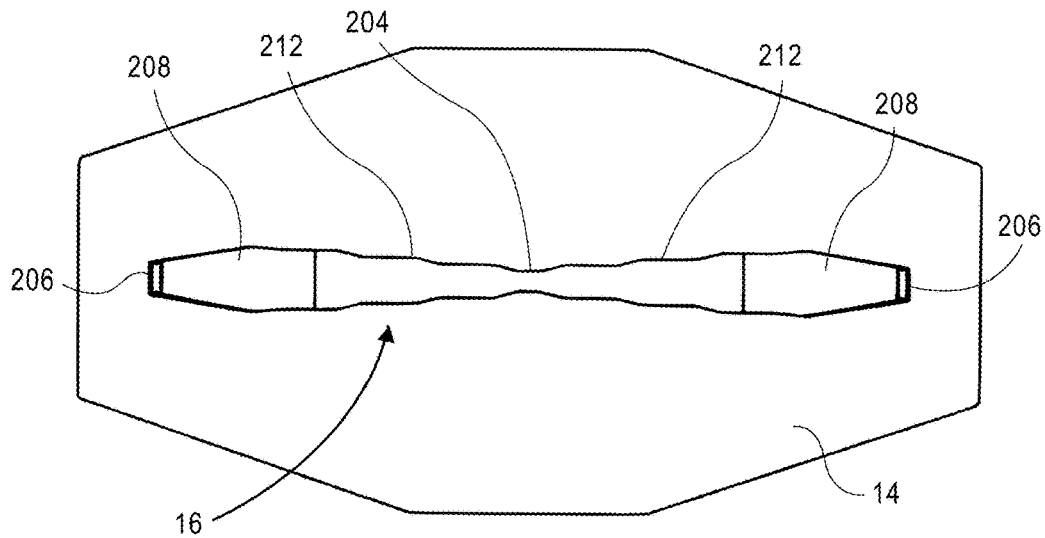

FIGS. 14A-14J illustrate several different embodiments of microfluidic chips 14 with different configurations for the microfluidic channel 16. FIG. 14A illustrates a microfluidic chip 14 having a microfluidic channel 16 with an hour glass design. In this embodiment, the microfluidic channel 16 has a gradual tapering side profile 200, 202 that reaches a small constriction region 204 that is roughly midway along the length of the microfluidic chip 14. As seen in FIG. 14A, the first stage of the microfluidic chip 14 (from left to right) has an inlet 206 defined by a cross sectional area (x) that tapers 208 outwardly to a cross sectional area greater that is greater than x. Then the microfluidic channel 16 gradually tapers 200, 202 down to the constriction region 204 with a cross sectional area that is less than x. The design is meant to gradually increase the velocity of the sample 12 as it passes through the smaller cross sectional area of the constriction region 204. In an alternative embodiment, rather than have a gradual taper 200, 202 to the constriction region 204, the microfluidic channel 16 may have a stepwise taper 212 as seen in FIG. 14B. Note that the initial expansions 208 on either side of the microfluidic chip 14 may be omitted as well, in which case the microfluidic channel 16 gradually decreases in cross sectional area until the constriction region 204. In one particular embodiment, the constriction region 204 may have a width of around 1.5 mm and a depth of around 1.5 mm. In several embodiments, the length, or width, can range from about 0.1 mm to about 0.3 mm, about 0.3 mm to about 0.6 mm, about 0.6 mm to about 0.9 mm, about 0.9 mm to about 1.2 mm, about 1.2 mm to about 1.5 mm, about 1.5 to about 1.7 mm, or about 1.7 mm to about 2.0 mm, or any value between those listed, including endpoints. Larger dimensions could also be used, depending on the embodiment. The inlet 206 (or outlet) may have a larger dimension such as, for example a depth of around 6 mm and a width of around 5 mm. Likewise, the length (or width) of the inlet can vary, depending on the embodiment, for example ranging from about 2 mm to about 3 mm, about 3 mm to about 4 mm, about 4 mm to about 5 mm, about 5 mm to about 6 mm, about 6 mm to about 7 mm, about 7 mm to about 8 mm or any value between those listed, including endpoints. The length of the constriction region 204 of the microfluidic channel is defined by y and may be on the order of about 1.5 mm. Other dimensions may be used, for example those ranging between about 0.5 and 0.7 mm, about 0.7 to about 1.0 mm, about 1.0 to about 1.2 mm, about 1.2 mm to about 1.5 mm, about 1.5 mm to about 1.7 mm, about 1.7 to about 2.0 mm or any value between those listed, including endpoints.

Figure 14C:
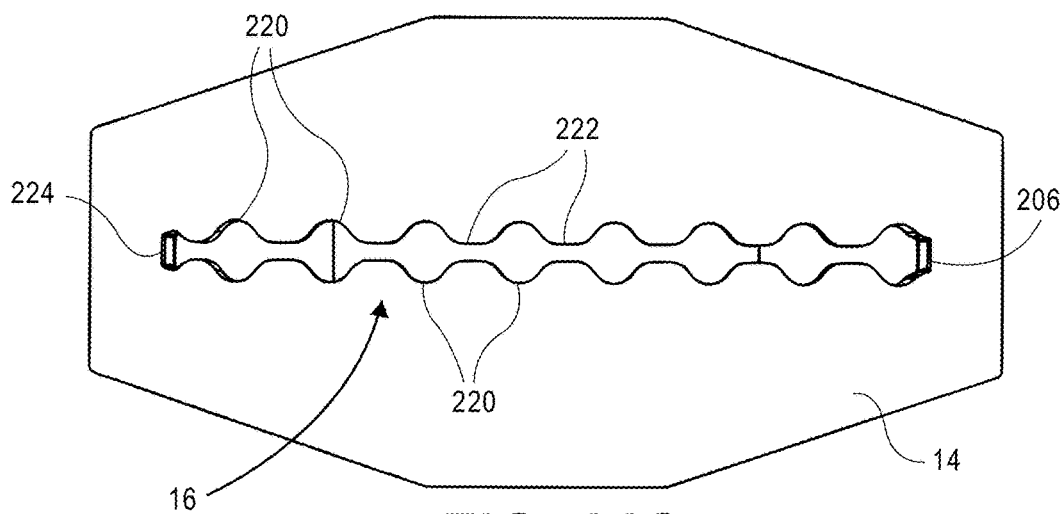

FIG. 14C illustrates a microfluidic chip 14 having a single microfluidic channel 16 with a series of expansion regions 220 and constriction regions 222. In this design, the microfluidic channel 16 may have an initial cross sectional area of x at the inlet 224. Then the channel can expand outwardly to a cross sectional area greater than x at the expansion region 220. The expansion region 220 may have a width (measured at the maximum width) within the range of about 1 mm to about 5 mm. For example, one illustrative width for the expansion region 220 is 1.3 mm. Other embodiments can employ other widths, such as about 1 mm to about 1.2 mm, about 1.2 mm to about 1.4 mm, about 1.4 mm to about 1.7 mm, about 1.7 mm to about 2.0 mm, about 2.0 mm to about 2.5 mm, about 2.5 mm to about 3.0 mm, about 3.0 mm to about 4.0 mm, 4.0 mm to about 5.0 mm, or any value between those listed, including endpoints. After the expansion the microfluidic channel 16, the microfluidic channel 16 then gets smaller at the constriction region 222 to a cross sectional area less than or equal to x. The constriction region 220 may have a width within the range of about 100 μm to about 3 mm. A particular illustrative width for the constriction region 220 is 400 μm. Other embodiments employ widths of, for example, about 100 μm to about 150 μm, about 150 μm to about 200 μm, about 200 μm to about 250 μm, about 250 μm to about 500 μm, about 500 μm to about 750 μm, about 750 μm to about 1000 μm, about 1000 μm to about 1.5 mm, about 1.5 mm to about 2 mm, about 2 mm to about 2.5 mm, about 2.5 mm to about 3.0 mm, and any value therebetween, including endpoints.

Figure 14D:
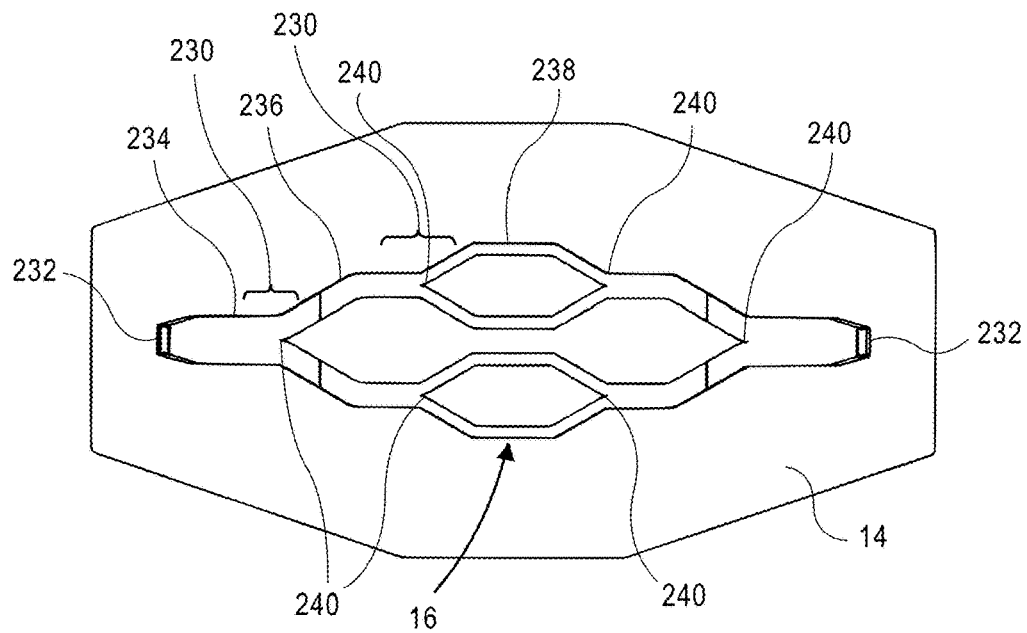

FIG. 14D illustrates a microfluidic chip 14 having a microfluidic channel 16 that includes a series of bifurcations 230 whereby a microfluidic channel 16 branches into two smaller microfluidic channels. There may be multiple stages of bifurcations as seen in FIG. 14D. The smaller microfluidic channels 16 than recombine with two microfluidic channels combining to one. This process completes when the microfluidic channels 16 combine into a single channel on the opposing side of the microfluidic chip 14. In this embodiment, the microfluidic chip 14 can be designed to have an initial cross sectional area of x at the inlet 232 (or outlet). Then the microfluidic channel 16 can expand, constrict or stay equal to the inlet cross sectional area of x at the first region 234. The single microfluidic channel 16 then bifurcates to two microfluidic channels 236. These bifurcated microfluidic channels 236 are now less than the initial cross sectional area x of the first region 234. Then the bifurcated microfluidic channels 236 then bifurcate again to create four microfluidic channels 238. The cross sectional area of these microfluidic channels 238 are even smaller than the initial cross sectional area x. Generally, the cross section area of bifurcating channels can be determined by x/y or less where x is the initial cross sectional area and y is the amount of parallel channels in that section. Each subsequent stage of microfluidic channels (236, 238) is smaller than the upstream microfluidic channels. In this embodiment, at each point of bifurcation, edges 240 are formed that are sharp tip or point that is formed at the apex of the gradually tapered walls of the microfluidic channels that converge. This creates a knife edge that cuts fat or other tissue as it passes by.

Figure 14E:
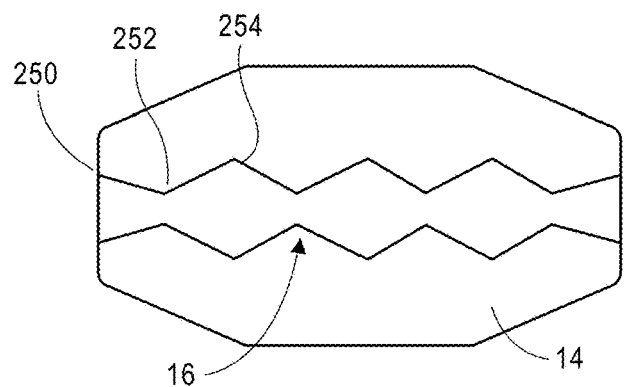

FIG. 14E illustrates another embodiment of a microfluidic chip 14 where the microfluidic channel 16 has a diamond pattern where the inlet 250 has a cross sectional area of x. The channel has sections that sharply narrow to a constriction region 252 such that the cross sectional area is less than or equal to the initial cross sectional area x. Following the constriction region 252, the microfluidic channel expands sharply outward to reach an expansion region 254 that has a cross sectional area greater than or equal to x. This embodiment can have a plurality of the constriction regions 252 and expansion regions 254. The expansion region 254 may have a width (measured at the maximum width) within the range of about 1 mm to about 3 mm, for example about 1 mm to about 1.25 mm, about 1.25 mm to about 1.5 mm, about 1.5 mm to about 1.75 mm, about 1.75 mm to about 2.0 mm, about 2.0 mm to about 2.2.5 mm, about 2.25 mm to about 2.5 mm, about 2.5 mm to about 2.75 mm, about 2.75 mm to about 3.0 mm, and any value therebetween, including endpoints. The constriction region 252 may have a width within the range of about 100 μm to about 1 mm, including, for example a width of about 100 μm to about 200 μm, about 200 μm to about 300 μm, about 300 μm to about 400 μm, about 400 μm to about 500 μm, about 500 μm to about 600 μm, about 600 μm to about 700 μm, about 700 μm to about 800 μm, about 800 μm to about 900 μm, about 900 μm to about 1000 μm, an any value therebetween, including endpoints.

Figure 14F:
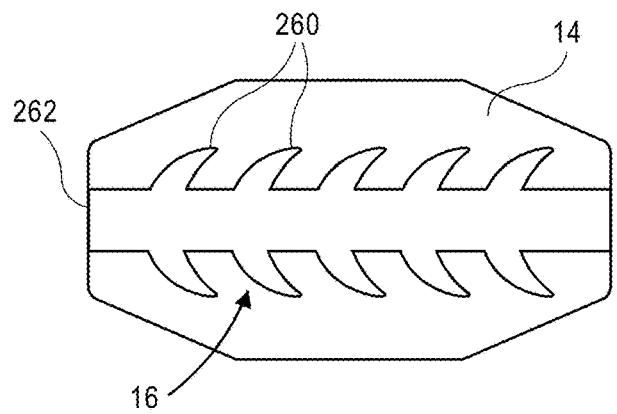

FIG. 14F illustrates another embodiment of a microfluidic chip 14 that uses a single microfluidic channel 16 having a plurality of fin shaped pockets 260 disposed along the length of the microfluidic channel 16. The fin shaped pockets 260 cause turbulence in the flow of fluid through the microfluidic chip 14 which imparts high shear stresses on the sample 12. For example, a sample 12 that contains cells or tissue can be passed through the microfluidic channel 16 with the fin shaped pockets 260 and the cells can be analyzed in response to the high shear stress environment. The fin shaped pockets 260 can have a maximum cross sectional area at their opening that is equal to or less than the cross sectional area of the inlet 262. The fin shaped pockets 260 taper down to a point.

Figure 14G:
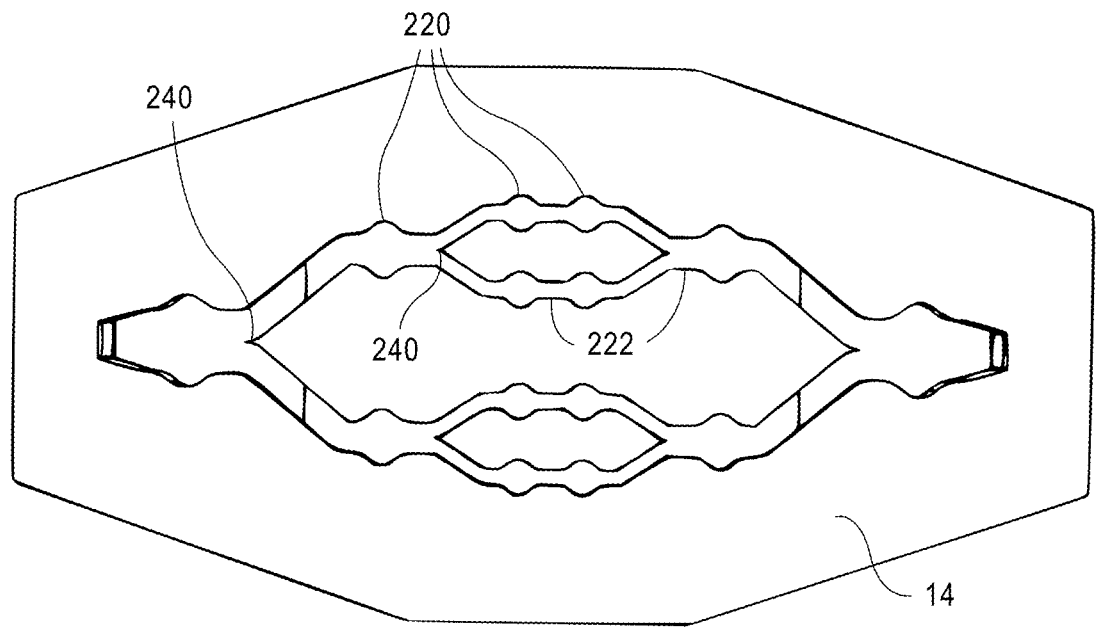
Figure 14H:
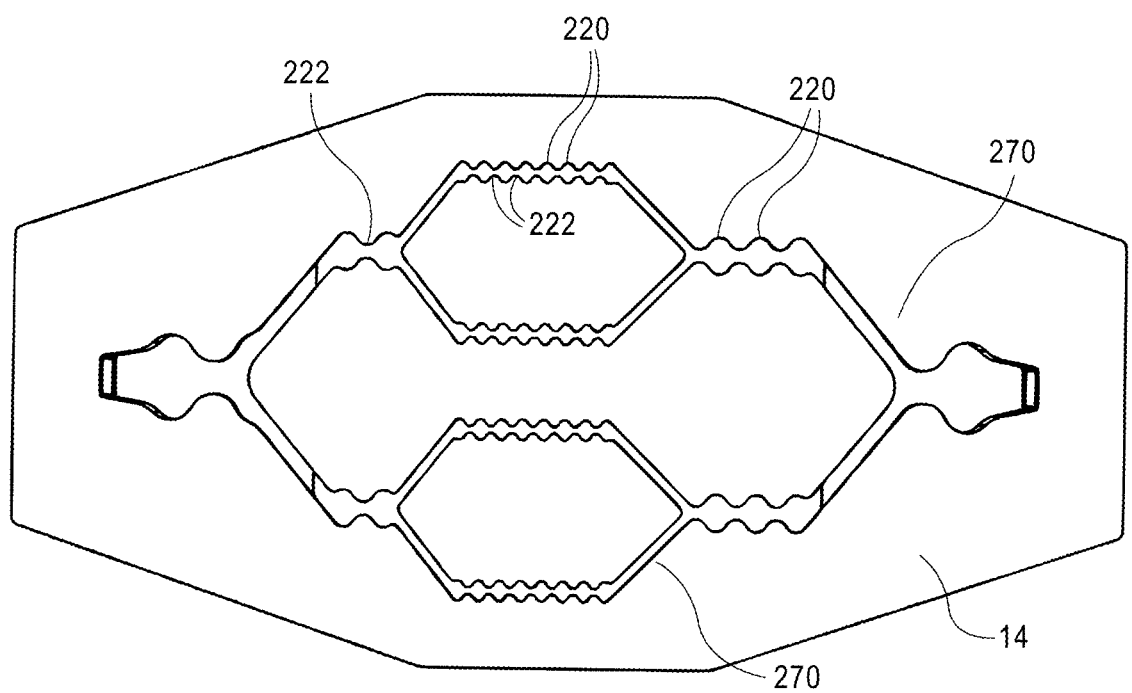

FIG. 14G illustrates another embodiment of a microfluidic chip 14. In this embodiment, the microfluidic chip 14 incorporates both knife edge bifurcations 240 as well as a plurality of expansion regions 220 and constriction regions 222. FIG. 14H illustrates another embodiment of a microfluidic chip 14 that includes bifurcations 270 without any knife edges along with a plurality of expansion regions 220 and constriction regions 222. As seen in FIG. 14H, a rounded or non-sharp corner is formed at each of the bifurcations 270. As one particular example, the constriction regions 222 may have a width of about 400 µm and a depth of about 300 µm. In several embodiments, the constriction regions range in width from about 200 µm to about 500 µm, including about 200 µm to about 250 µm, about 250 µm to about 300 µm, about 300 µm to about 350 µm , about 350 µm to about 400 µm, about 400 µm to about 450 µm, about 450 µm to about 500 µm, and any width therebetween, including endpoints. Likewise, constriction regions may have a depth ranging from about 200 µm to about 500 µm, including about 200 µm to about 250 µm, about 250 µm to about 300 µm, about 300 µm to about 350 µm, about 350 µm to about 400 µm, about 400 µm to about 450 µm, about 450 µm to about 500 µm, and any width therebetween, including endpoints. The expansion regions 220 may have a depth of about 300 µm and a width of about 1.3 mm, in several embodiments. In still additional embodiments, the depth the expansion regions may range from about 200 µm to about 500, including about 200 µm to about 250 µm, about 250 µm to about 300 µm , about 300 µm to about 350 µm, about 350 µm to about 400 µm, about 400 µm to about 450 µm, about 450 µm to about 500 µm, and any depth therebetween, including endpoints. The width, depending on the embodiment can range from about 0.5 mm to about 3 mm, including about 0.5 mm to about 0.75 mm, about 0.75 mm to about 1.0 mm, about 1.0 mm to about 1.1 mm, about 1.1 to about 1.2 mm, about 1.2 mm to about 1.3 mm, about 1.3 mm to about 1.4 mm, about 1.4 mm to about 1.5 mm, about 1.5 mm to about 2.0 mm, about 2.0 mm to about 2.5 mm, about 2.5 mm to about 3.0 mm, and any width therebetween, including endpoints. In one embodiment, the maximum depth of the microfluidic channel 16 at the inlet or outlet is about 6 mm. Other embodiments employ depths ranging from about 3 to about 7 mm, including about 3 mm to about 4 mm, about 4 mm to about 5 mm, about 5 mm to about 6 mm, about 6 mm to about 7 mm, and any depth therebetween, including endpoints.

Figure 14I:
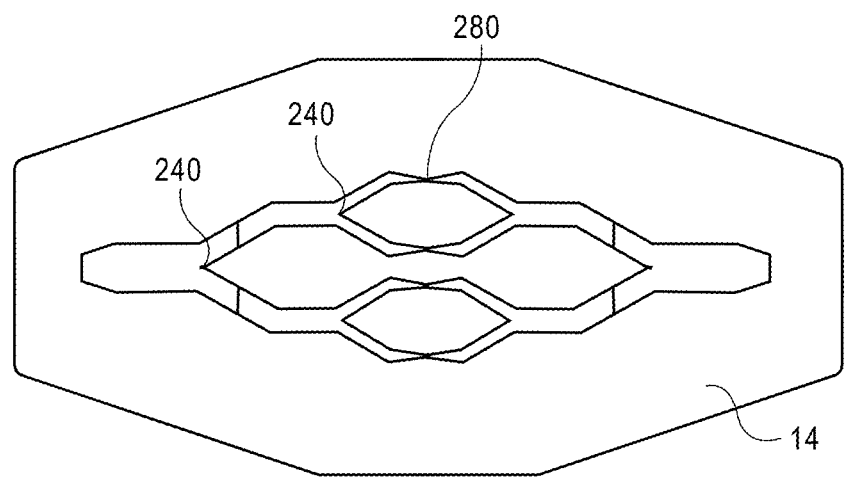
Figure 14J:
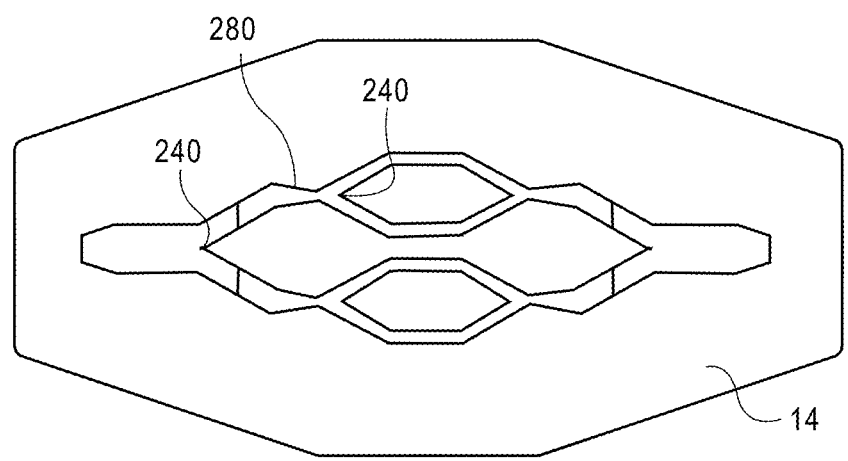

FIG. 14I illustrates another embodiment of a microfluidic chip 14 that includes knife edge bifurcations 240 and hour glass sections 280 similar to those of FIGS. 14A and 14B in the smallest bifurcation channels. FIG. 14J illustrates still another embodiment of a microfluidic chip 14 that includes knife edge bifurcations 240 and hour glass sections 280 located just upstream or prior to the knife edge bifurcations 240.

In one particular embodiment, fat tissue is processed using the systems described herein. First a physician or other health care professional would take a liposuction sample 12 from a patient ranging anywhere from 2 ccs to 100 ccs, depending on the application, such as about 2 to about 10 cc, about 10 cc to about 25 cc, about 25 cc to about 50 cc, about 50 cc to about 75 cc, about 75 cc to about 100 cc, or any volume therebetween, including endpoints. The fat is then initially processed by washing the blood out with phosphate-buffered saline (PBS) buffer solution (or other acceptable buffer) multiple times. Once this process is finished the fat sample 12 is loaded into the sample chamber 70, 72 using a syringe or the like and the sample chamber is loaded into the carriage 60, 60' along with the microfluidic chip 14, 14'. Alternatively, instead of loading the fat sample 12 into a separate sample chamber 70, 72, the contents of the syringe (e.g., syringe chamber 86 of FIGS. 8A and 8B) may be directly loaded into the carriage 60, 60' along with the microfluidic chip 14, 14'. This process may be used for a single microfluidic chip 14, 14' or for multiple microfluidic chips 14, 14' (e.g., for large sample processing or samples from different subjects).

With the sample chambers 70, 72 (or syringe chamber 86) and microfluidic chips 14, 14' loaded into their respective carriages 60, 60', the run begins using the controller 50 to operate the motor 40. The rotational speed is initially ramped up to a desired RPM rate, one non-limiting embodiment of which is illustrated in FIG. 4. This causes the fat sample 12 to move from the sample chamber 70 (assuming this is the most radially inward sample chamber) into the microfluidic chip 14 where the sample undergoes shear forces in the one or more microfluidic channels 16. The sample continues into the other sample chamber 72 whereupon the carriage 60, 60' and microfluidic chip 14, 14' are rotated through 180° using any one of the modalities described herein (e.g., deceleration, electromagnetic, mechanical gearing, centripetal ratchet, manual rotation, etc.). After rotating, spinning, or flipping the microfluidic chip 14, 14' the support plate 30 is rotated to drive the sample from the sample chamber 72 into the microfluidic chip 14, 14' where the sample is exposed to additional shear forces in the one or more microfluidic channels 16. The sample continues to move radially outward and into the sample chamber 70. The carriages 60. 60' and the microfluidic chips 14, 14' are rotated again through 180° and the process repeats for the desired number of cycles.

After the fat sample 12 has been run through the microfluidic chip 14, 14' the desired number of cycles or times, the now processed fat sample 12 is removed from the sample chamber 70, 72 (or syringe chamber 86). In one embodiment, the processed fat sample 12 is then transferred from the sample chamber 70, 72 to a separate syringe that attaches at head 74 whereby the processed sample 21 can be withdrawn. With the processed sample 12 now in the syringe, it is then optionally injected into the subject. Alternatively, if the syringe chamber 86 was used as the sample chamber, then the syringe chamber 86 is used to directly inject the subject with the fat sample 12 that is contained therein.

Figure 15:
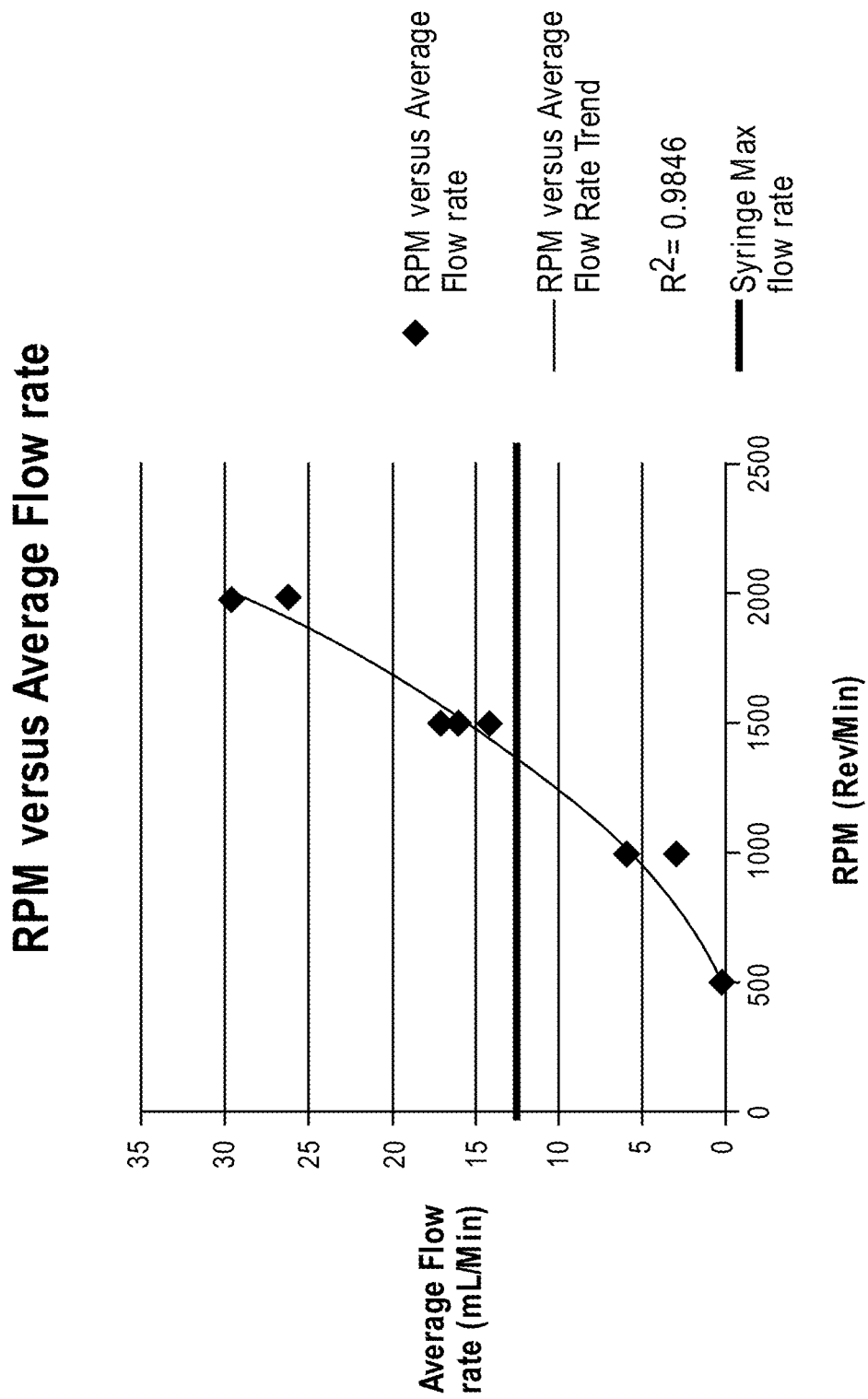
FIG. 15 illustrates a graph illustrating the average flow rate (mL/min) obtained using a microfluidic chip with systems disclosed herein (e.g., FIG. 11) at various RPMs. Also illustrated for comparison purposes is the maximum flow rate achieved using a standard syringe pump to pass fluid back-and-forth through a fat processing chip.
Figure 16:
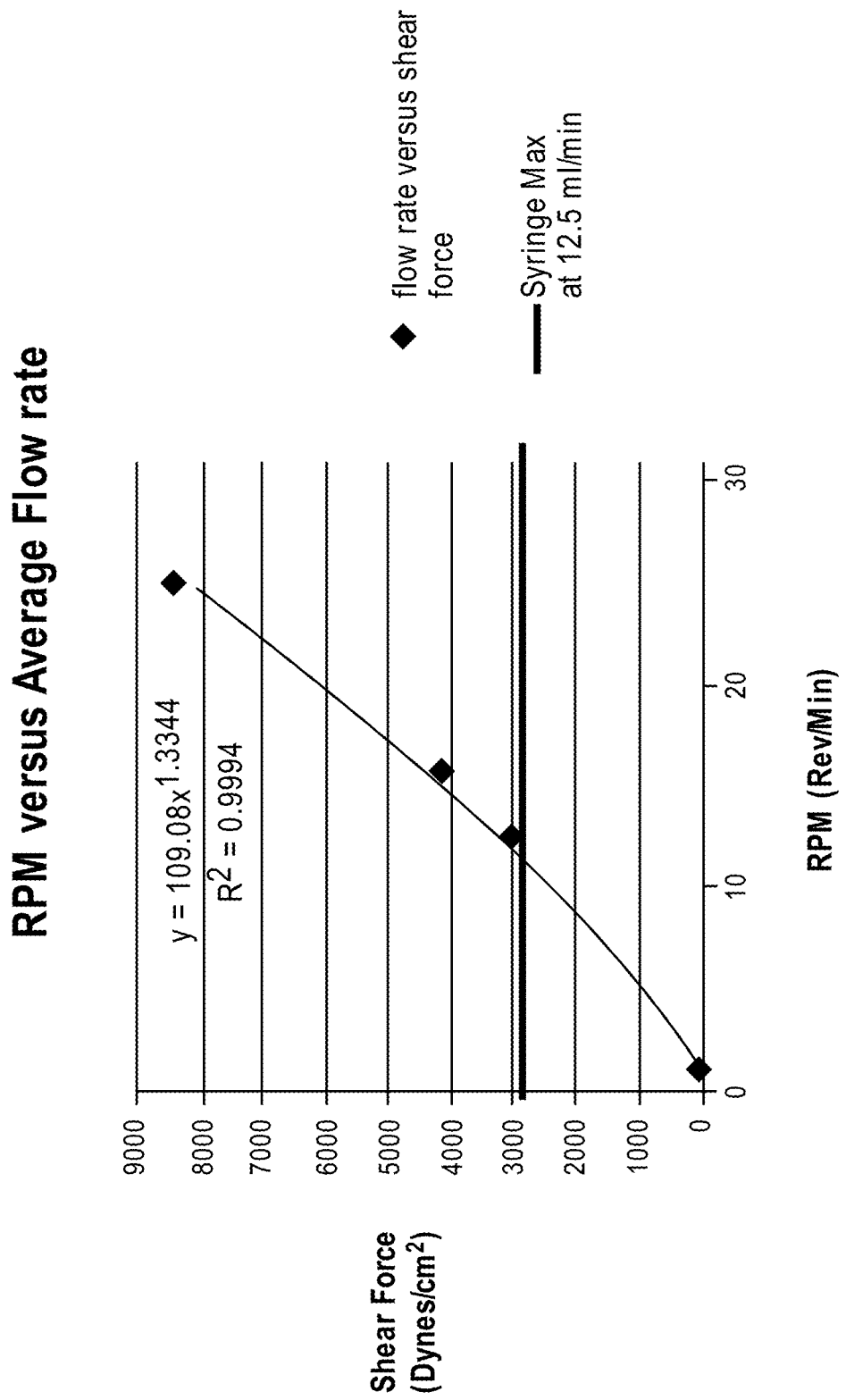
FIG. 16 illustrates a graph illustrating the average shear force (Dynes/cm$^2$) obtained using a microfluidic chip with systems disclosed herein (e.g., FIG. 11) at various RPMs. Also illustrated for comparison is the maximum shear force achieved using a standard syringe pump to pass fluid back-and-forth through a fat processing chip.

The design also allows for quick and multiple iterations to be done in relatively short time periods, for example less than ten minutes according to some embodiments. For example, in several embodiments, 20 iterations can be done in 4 minutes, while 100 iterations can be done 20 minutes. In this platform, any flow rate between 0 mL/min to 700 mL/min (or higher) can be achieved, for example, 0 mL/min to about 10 mL/min, about 10 mL/min to about 25 mL/min, about 25 mL/min to about 50 mL/min, about 50 mL/min to about 75 mL/min, about 75 mL/min to about 100 mL/min, about 100 mL/min to about 200 mL/min, about 200 mL/min to about 300 mL/min, from about 300 mL/min to about 400 mL/min, about 400 mL/min to about 500 mL/min, about 500 mL/min to about 600 mL/min, about 600 mL/min to about 700 mL/min, and any rate therebetween, including endpoints. In prior syringe pump based processes, the maximum flow rate a fluid pump could manage was around 12.5 mL/min. FIG. 15, for example, illustrates a graph of average flow rate through the microfluidic chip 14 as a function of RPM using a system 10 of the type illustrated in FIG. 11. In addition, the system 10 described herein is able to generate high shear forces; much higher than shear forces generated using syringe pump based processes as seen in FIG. 16. This design also has the advantage of performing processing of a single iteration in about 10 seconds which is much faster than other pump-based processes.

Figure 17:
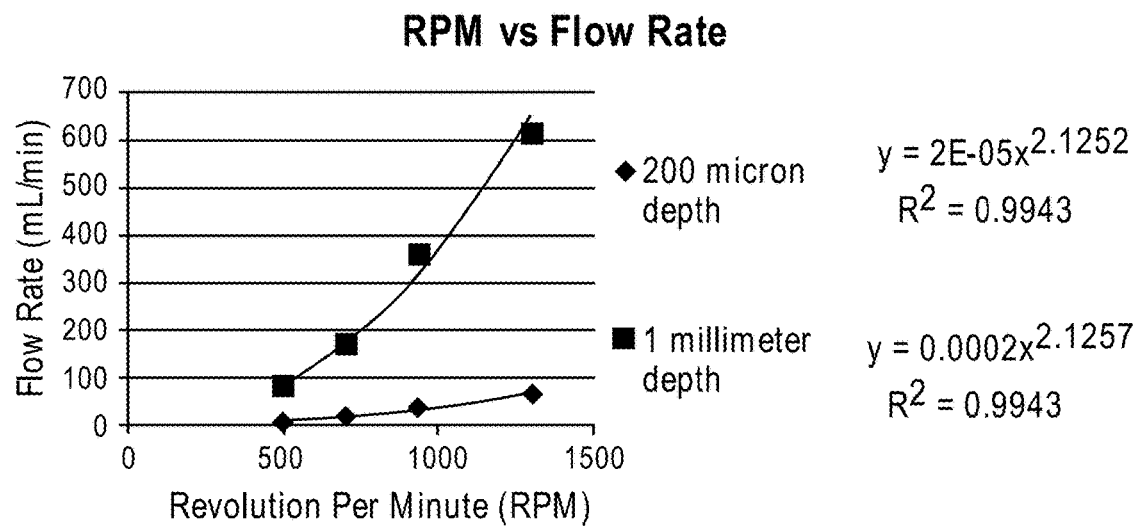
FIG. 17 illustrates a graph illustrating flow rate as a function of RPM for two different microfluidic chips using the systems disclosed herein, such as that depicted in FIG. 5.
Figure 18:
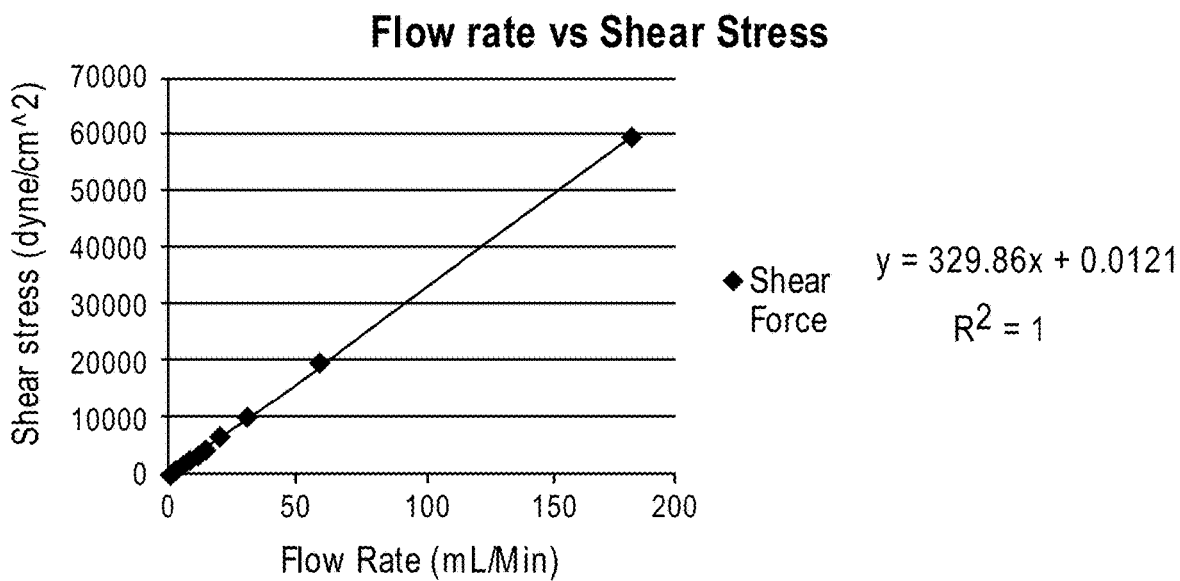
FIG. 18 illustrates a graph illustrating flow rate as a function of shear rate for one of the microfluidic chips of FIG. 17.

FIG. 17 illustrates a graph of experimentally obtained data showing flow rate (mL/min) through two different microfluidic chips 14 as a function of RPM that were processed using the system 10 illustrated in FIG. 5. The first microfluidic chip 14 was of the type illustrated in FIG. 14G (e.g., bifurcating microfluidic channels with expansion and constriction region) and included a depth of 200 μm and width of 300 μm. The second microfluidic chip 14 was of the type illustrated in FIG. 14G (e.g., bifurcating microfluidic channels with expansion and constriction region) and included a depth of 1 mm and width of 300 μm. As seen in FIG. 17, high flow rates are achievable even at RPMs below 1,500. FIG. 18 illustrates a graph showing the calculated shear stress as a function of RPM for the microfluidic chip 14 with the smaller dimensions (e.g., depth of 200 μm and width of 300 μm). The shear stress was calculated using the following equation:

$$\tau = \frac{6\mu Q}{wh^2} \quad (1)$$

where τ is the shear stress, "6" is a constant, μ is fluid viscosity, Q is flow rate, w is width of the channel, and h is depth of the channel. As seen in FIG. 18, shear forces up to 60,000 dynes/cm$^2$ (per pass through the microfluidic chip 14) were achieved using the microfluidic chip 14. Of course, shear forces above 60,000 dynes/cm$^2$ may be achieved with a higher RPM motor 42. In several embodiments, shear forces ranging from about 10,000 dynes/cm$^2$ to about 100,000 dynes/cm$^2$ can be achieved, including forces from about 10,000 dynes/cm$^2$ to about 20,000 dynes/cm$^2$, 20,000 dynes/cm$^2$ to about 30,000 dynes/cm$^2$, about 30,000 dynes/cm$^2$ to about 40,000 dynes/cm$^2$, about 40,000 dynes/cm$^2$ to about 50,000 dynes/cm$^2$, about 50,000 dynes/cm$^2$ to about 60,000 dynes/cm$^2$, about 60,000 dynes/cm$^2$ to about 70,000 dynes/cm$^2$, about 70,000 dynes/cm$^2$ to about 80,000 dynes/cm$^2$, about 80,000 dynes/cm$^2$ to about 90,000 dynes/cm$^2$, about 90,000 dynes/cm$^2$ to about 100,000 dynes/cm$^2$, or any force therebetween, including endpoints.

One primary application of the system 10 is to dissociate, enrich, and activate the stem cells found in fat tissue. As explained herein, the shear forces generated within the microfluidic channel(s) 16 of the microfluidic chip 14, 14' are used to break down fat tissue, mesenchymal stem cells and other cells found within the fat tissue. The various microfluidic chip 14 designs illustrated herein (e.g., FIGS. 14A-14J) apply increased shear stresses to the sample. For example, constrictions, tapers, and shaped surfaces of the microfluidic channel 16 breaks down the fat tissue and activate cells found within.

Figure 19:
FIG. 19 is a microscope image (4×) obtained of tumor tissue (MCF7) processed at 300 RPM with three passes using one non-limiting embodiment of the systems described herein.
Figure 20:
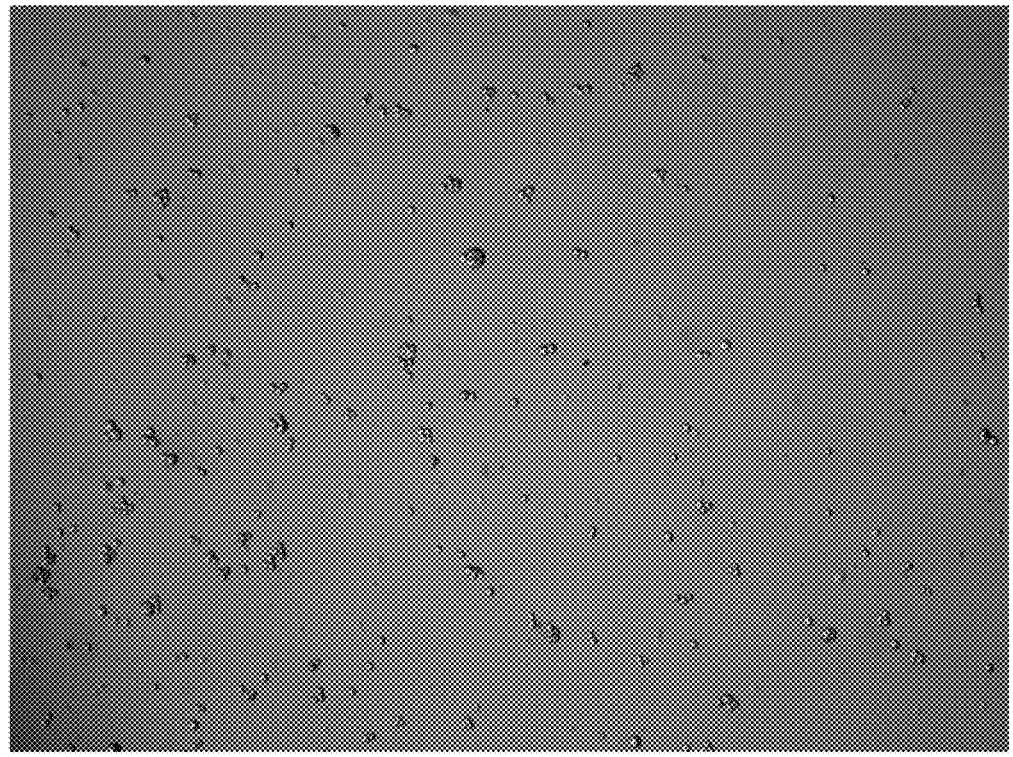
FIG. 20 is a microscope image (4×) obtained of non-processed, harvested tumor cells (MCF7) used as a control.

The system 10 may be used in other applications. For example, the system can be used for tumor cell isolation. In this sense it can also be used a general cell dissociator or cell separator in which samples are broken down into single cells or aggregates of a few cells. FIG. 19 illustrates a microscopic image taken of tumor cells that have been run through a microfluidic chip 14 using the system 10 described herein. As seen in FIG. 19, there are large numbers of single cells in the field of view. This is in contrast with the control of unprocessed tumor tissue which can be seen in FIG. 20 which has far fewer single cells. Additional tissue types that can be used with the system 10 include, for example, brain tissue and bone marrow. Cells can also be run through the microfluidic chip 14, 14' to impart shear stress on the cells so that they can undergo phenotype or other changes (e.g., mesenchymal stem cells). Separately, the microfluidic chips 14, 14' break down aggregates of cells by applying shear stress to the aggregates to shear off single cells for isolation. These single cells can then be classified (e.g., tumor type) or analyzed for cellular signals or secretions.

Figure 21:
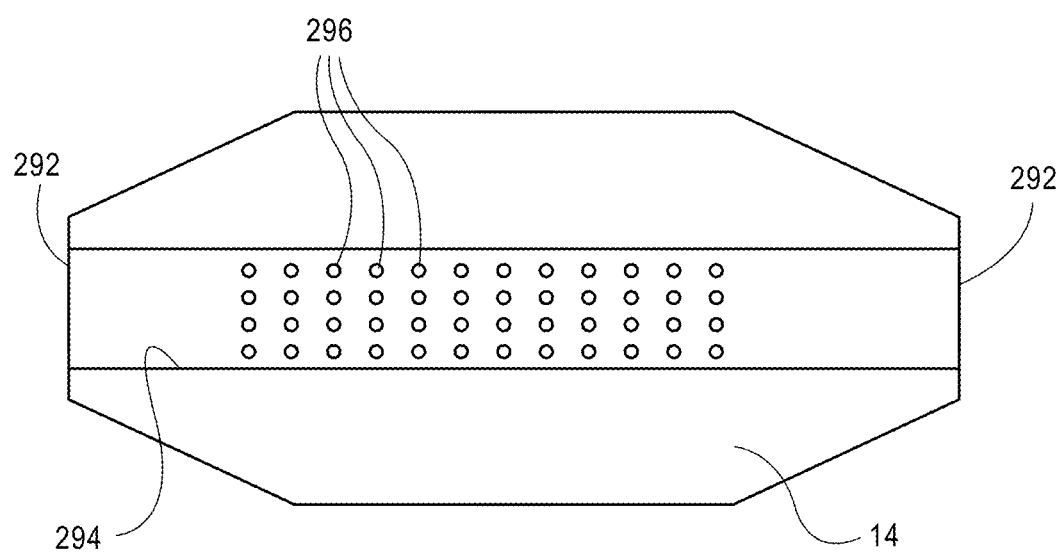
FIG. 21 illustrates a microfluidic chip having a plurality of reservoirs located in a surface thereof that are used to trap cells or cell aggregates therein.

FIG. 21 illustrates one embodiment of a microfluidic chip 14 that can be used to sort out single cells or sort cells by size for use in the lab or diagnosis. For example after breaking down tumor cells or islet cells, the microfluidic chip 14 can be used to sort out and trap single tumor cells for studying. The microfluidic chip 14 is designed to sort single cells or any aggregates of specific size. The microfluidic chip 14 has two inlets or outlets 292 where the sample enters/exits that has a cross sectional area (x). The sample then flows through the main channel 294 that has a cross sectional area greater than, less than or equal to the inlet/outlet cross section area (x). As the sample flows through the main channel 294 it passes over small reservoirs 296 formed in the bottom and/or the sides of the microfluidic chips 14. The reservoirs 296 may include wells that have sizes that are less than, for example, about 100 microns in diameter. These reservoirs 296 are less than or equal to the cross sectional area of the main channel 294. The small reservoirs 296 can be made to the specific size of single cells or aggregates depending on the application. The reservoirs can also be angled 0 to 90° from perpendicular (e.g., 0° to 10°, 10° to 30°, 30° to 45°, 45° to 60°, 60° to 90°, etc.) to the main channel 294 to add effect and better trapping of cells. In one embodiment, the trapped cells can be flushed out of the microfluidic chip 14 for downstream analysis. In an alternative embodiment, the cells may remain in the reservoirs 296 and imaged or otherwise analyzed directly on-chip.

In addition, this system 10 can mount any kind of microfluidic chip 14, 14', thus allowing it to be universal to almost any microfluidic device. Since this platform can integrate any chip for processing, the future applications can involve: stem cell therapeutics, Alzheimer's treatment, arthritis treatment, wound care treatment, cosmetics, spinal cord injury, broken bone injury, brain injury, ulcer treatment, organ treatment, blood therapy, reconstruction therapy, immune therapy, nutritional applications, hair growth therapy, vision treatment, neurological therapy, muscle therapy, and cartilage replacement.

Figure 22:
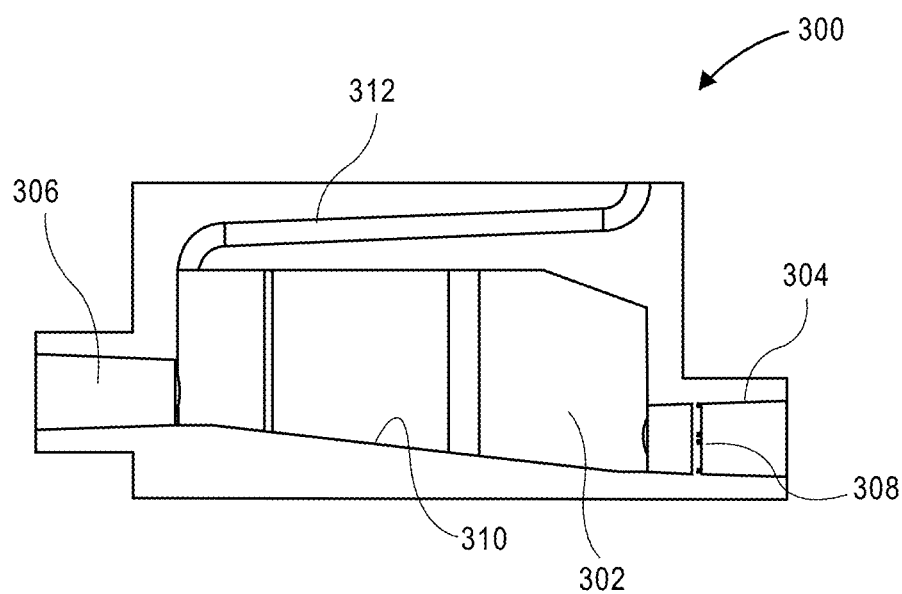
FIG. 22 illustrates a cross-sectional view of a sample holding chamber according to another embodiment that incorporates a one-way valve.
Figure 23:
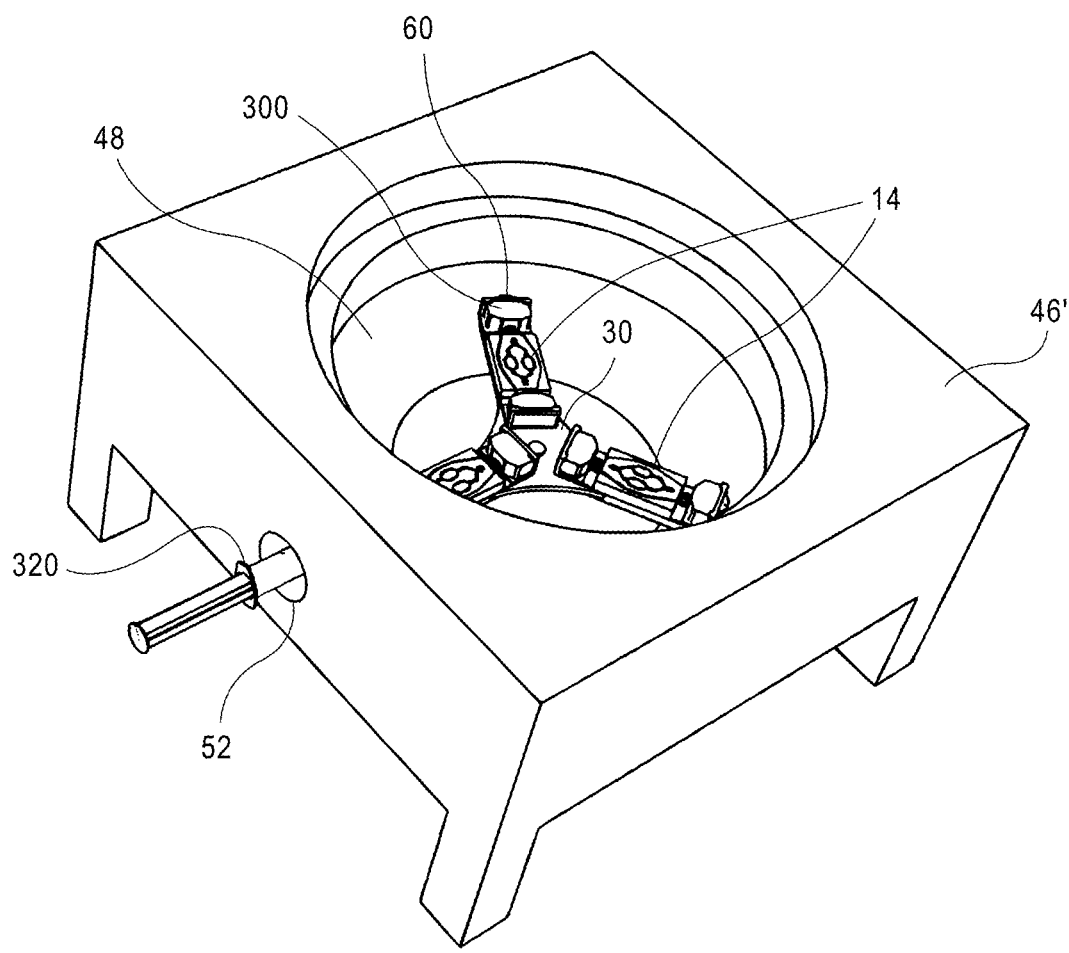
FIG. 23 illustrates a system for processing a sample according to another embodiment that uses access ports for loading/retrieving a sample from sample chambers mounted on a rotating support plate or disk.

FIG. 22 illustrates another embodiment of a sample chamber 300 that can be used with the encasement 46' embodiment illustrated in FIG. 23. In this embodiment, the sample chamber 300 includes an interior chamber 302 that is in fluidic communication with an inlet 304 and an outlet 306. The inlet 304 is used to fill the interior chamber 302 with sample and includes a one-way valve 308 disposed therein. The one-way valve 308 may include any sort of mechanical valve and may also include a releasable septum. As explained below, the inlet 304 and one-way valve 308 is dimensioned such that a syringe 320 (FIG. 23) that contains the sample can be inserted into the inlet 304 and open the one-way valve 308 so that the contents of the syringe 320 can be loaded into the interior chamber 302 or removed from the interior chamber 302.

The outlet 306 of the chamber 300 is in fluidic communication with the microfluidic chip 14, for example, using ports 20, 22. The interior chamber 302 includes a sloped lower surface 310. The sloped lower surface 310 is sloped to force the contents of the chamber 300 toward the inlet 304 so that when the processed sample is extracted, the entire sample is retrieved. The sample chamber 300 includes a vent channel 312 that communicates between the interior chamber 302 and the exterior of the sample chamber 300 (i.e., vents to atmosphere). As seen in FIG. 22, the vent channel 312 goes from the inside of the front of the chamber 300 (the side that connects to the microfluidic chip 14), to the atmosphere at the back of the chamber 300 (the back is where the syringe is attached to fill the interior chamber 302). This allows airflow during processing so the fluid moves evenly through.

FIG. 23 illustrates an embodiment of an encasement 46' that is used with the chambers 300 illustrated in FIG. 22. As seen in FIG. 23, microfluidic chips 14 are mounted on the carriages 60 along with the chambers 300. The encasement 46'in this embodiment includes a bowl 48 that can be used to catch any sample that inadvertently spills or is released during the process. The encasement 46' further includes an access port 52 located on the side of the encasement 46' that is dimensioned to accommodate the syringe 320 so that sample can be loaded into the chambers 300 or removed from the chambers 300 after processing. FIG. 23 illustrates syringe 320 extending through the access port 52 and inserted into the inlet 304 of a chamber 300 whereby unprocessed sample can be loaded into the interior chamber 302 or removed therefrom after processing has completed.

For loading or unloading of the chambers 300, the microfluidic chip 14 is aligned with the access port 52 and the syringe 320 is then inserted into the access port 52 and into the inlet 304 to open the one-way valve 308. Once complete, the syringe 320 is removed which then closes the one-way valve 308 and prevents any sample from leaking. The microfluidic chips 14 are then processed as described herein with multiple cycles of spinning or rotating of the carriages 60 and their microfluidic chips 14 so the sample passes back and forth through the microfluidic chips 14. After processing, support plate 30 can be rotated to align the microfluidic chip 14 with the access port 52. The user will attach the syringe 320 to the inlet 304 of the chamber 300, opening the one-way valve 308. The processed sample can then be extracted into the syringe 320. The sloped lower surface 310 aids in evacuating the entire contents of the chamber 300. This unloading process may be done for each microfluidic chip 14.

Figure 24:
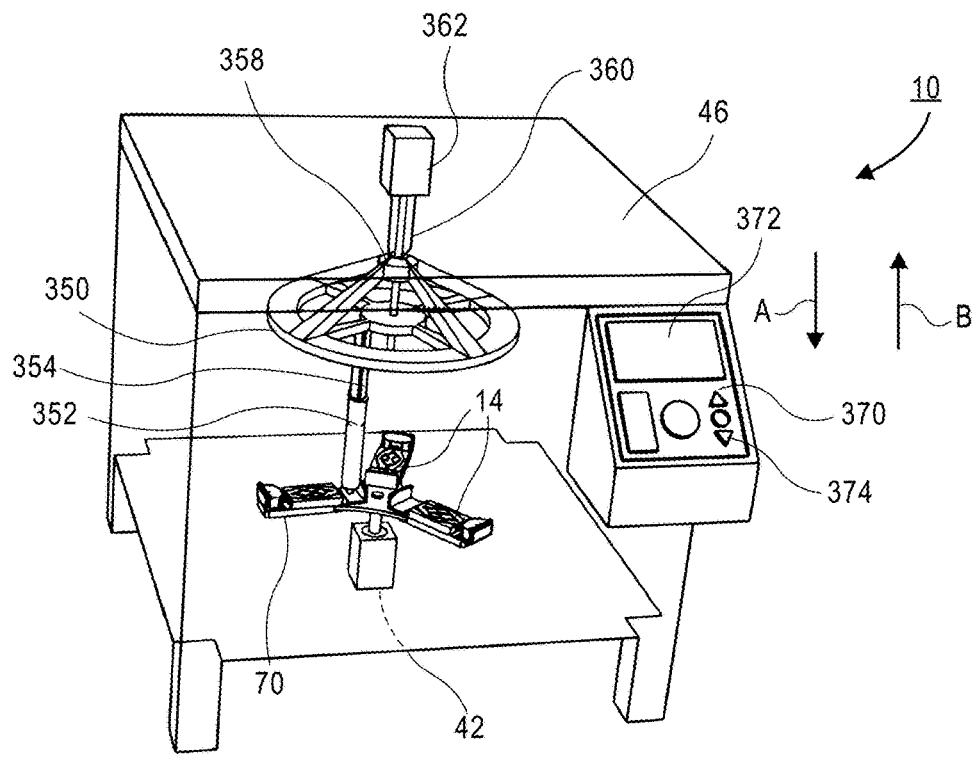
FIG. 24 illustrates another embodiment of system for processing a sample according to another embodiment. In this embodiment, one or more syringes (or other sample vessels of variable volume) are spun or rotated along with the microfluidic chip(s) and rotate or spin 180° to process the sample back and forth through the microfluidic chip(s). A moveable top plate or ring is secured to the plunger of the syringe and is used to eject or retrieve the sample depending on the direction of movement of the plate.
Figure 25:
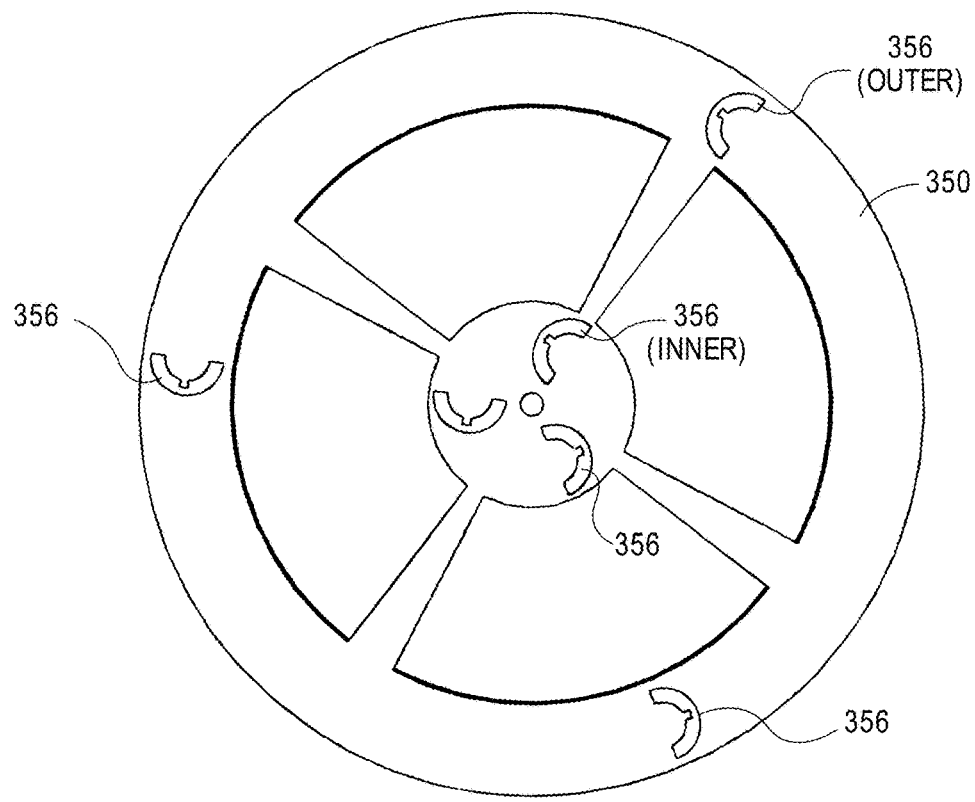
FIG. 25 illustrates a bottom, plan view of the moveable top plate or ring of the embodiment of FIG. 24.
Figure 26:
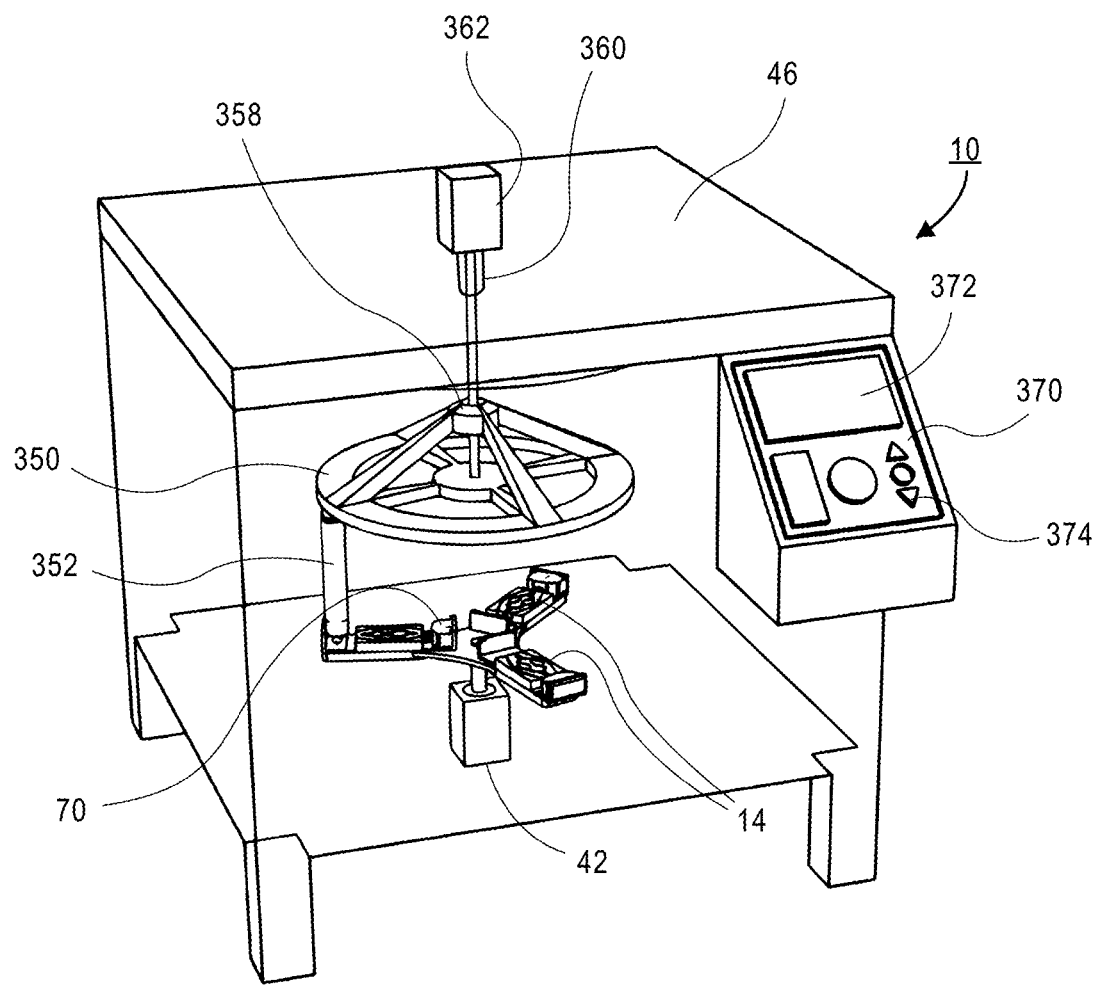
FIG. 26 illustrates a perspective view of the embodiment of FIG. 24 wherein the microfluidic chips and syringes have rotated through 180° and the moveable top plate or ring has been partially lowered to depress the syringe plunger.

FIGS. 24-26 illustrate another embodiment of the system 10. In this embodiment, the system 10 includes a top plate or ring 350 that interfaces with one or more syringes 352 that are mounted vertically with respect to the microfluidic chips 14. The outlet of the syringes 352 are coupled to the port 20 of the microfluidic chip 14 using an adapter 80 or the like (e.g. FIG. 2) that fluidically couples the end of the syringe 352 with the microfluidic chip 14. The opposing end of the microfluidic chip 14 may be coupled to a sample chamber 70, 72 as disclosed herein. The syringe plunger 354 of the syringe 352 is held via the top plate or ring 350 using hooks or clips 356 that are dimensioned to hold the syringe plunger 354 as seen in FIG. 25. In a preferred embodiment, there is a first set of hooks or clips 356 that are radially inward (e.g., inner) and a second set of hooks or clips 356 that are located radially outward (e.g., outer) as seen in FIG. 25. In some examples, the first set of hooks or clips 356 and the second set of hooks or clips 356 are configured to allow the distal end of the syringe plunger 354 to be easily secured into and removed from each of the hooks or clips 356. These different hooks or slips 356 engage with the syringe plunger 354 depending on the "spin" state of the microfluidic chip 14 and the attached syringe 352. As will be discussed in more detail below, as the carriage 60 is rotated, the syringe 352 attached to the microfluidic chip 14 can be rotated from a radially inward position to a radially outward position. As the carriage 60 is rotated, the distal end of the syringe 352 can be disengaged from the first set of hooks or clips 356 that are radially inward and subsequently engaged/secured to the second set of hooks or clips 356 that are located radially outward.

Thus, in this embodiment, the one or more syringes 352 are held generally perpendicular to the rotational plane of the microfluidic chips 14. The top plate or ring 350 is rotationally mounted on a bearing 358 that is internally threaded and engages with a threaded rod 360 that is coupled to a rotary motor 362. The bearing 358 enables the top plate or ring 350 to rotate along with the microfluidic chips 14 and attached syringe(s) 352. Activation of the rotary motor 362 causes rotation of the threaded rod 360 and vertical movement of the top plate or ring 350. Rotation in one direction causes the top plate or ring 350 to move downward in the direction of arrow A, thereby pushing the syringe plunger 354 down in the barrel of the syringe 352. Movement of the motor 362 in this direction is used to evacuate the contents of the syringe 352 into the microfluidic chip 14. Conversely, movement of the rotary motor 362 in the opposing direction causes the threaded rod 360 to rotate in the opposite direction and effectuates movement of the top plate or ring 350 in the upward direction (seen by arrow B), thereby pulling the syringe plunger 354 out of the barrel of the syringe 352. Movement of the motor 362 in this direction is used to pull or evacuate sample from the microfluidic chip 14 into the syringe 352. The rotary motor 362 may be secured to the top of the encasement 46 as illustrated in FIG. 24.

In this embodiment, with the microfluidic chips 14 mounted in the carriages 60 on the support plate 30, the syringes 352 are attached at one end (radially inward location as seen in FIG. 24) to the microfluidic chips 14 via an adapter 80 or the like and at the other end via the hooks or clips 356. The system 10 includes a control panel 370 that may be mounted on the encasement 46 and can be used to program the run parameters (e.g., RPM rates, run times, deceleration rates, cycle number, cycle time, etc.). The control panel 370 may also be used to monitor the state of the particular run using a display 372 or the like. Buttons 374 are provided so that the user may interface with the control panel 370. The system 10 begins with the rotation of the support plate 30 as previously explained herein using motor 42. During the spinning process, the syringes 352 rotate along with the microfluidic chips 14. The rotary motor 362 is activated to advance the top plate or ring 350 downward to move sample from the syringe 352 and into the microfluidic device 14. The spinning will stop for both the main motor 42 driving the support plate 30 and the rotary motor 362 and the syringe 352 with the microfluidic chip 14 will be spun 180° (e.g., deceleration causes the spinning although any other spinning modality may also be used). FIG. 26 illustrates the microfluidic chip 14 and the syringe 352 spun 180° to the radially outward location. As discussed above, the rotation of the carriage 60 and the attached microfluidic chip 14 and the syringe 352 can be done in a variety of ways. Rotation of the syringe 352 causes the plunger 354 to disengage with the hooks or clips 356 that the distal end of the plunger 354 is attached to. The syringe 352 can then engage with a different set of hooks or clips 356 (i.e., radially outward hooks or clips 356). The main motor 42 driving the support plate 30 and the rotary motor 362 is then activated (in the reverse direction) whereby the top plate or ring 350 moves away from the microfluidic chip 14 and is used to pull sample through the microfluidic chip 14 in the reverse direction. This process may repeat any number of times or cycles. After processing, the syringe 352 which contains the now processed sample may be removed from the system 10 and used directly to inject the patient or subject with the processed sample (e.g., fat tissue).

As explained herein, one primary use of the system 10 is the processing of adipose tissue for the generation of therapeutic and/or cosmetic applications. One advantageous aspect is that the processing takes place without the need for added enzymes or other digestion agents (e.g., collagenase). For example, the non-chemical treatment of processed tissue for wound healing applications is needed whereby the native extracellular matrix components are retained. Of course, in other embodiments, for example in those settings where the sample is evaluated in a laboratory setting, optional digesting agents such as collagenase or other chemicals or chemical agents may be added. These added agents may be used to increase the efficiency of cellular and subcellular component harvesting.

While adipose (or other) tissue is described as being processed using the microfluidic chip 14, it should be understood that tissue processing may be accompanied by various additional processing operations such as wash steps or filtration steps. These additional processing steps may be incorporated on-chip (e.g., on the microfluidic chip 14) or they be performed off-chip (i.e., after processing the sample on the microfluidic chip 14). For example, wash solutions may be loaded into chambers 70, 72 or other separate wash chambers (not shown) that can be used to wash the sample in the microfluidic chip 14. Likewise, a filter element 190 like that disclosed in FIG. 13 may be used to filter the sample upon exiting the microfluidic chip. Multiple filters may be used to perform sequential filtration.

In yet another embodiment, the sample 12 that is run through the system 10 includes cells. The system 12 may be used for the destruction (i.e., lysis) of cells by passing cells through the microfluidic chip 14 and exposing the same to high shear forces. Cell lysis will release the contents of the cells which may contain one or more subcellular organelles, cellular components, membrane bound organelles, extracellular vesicles, proteins, nucleic acids, paracrine factors and the like. In several embodiments, these components may be released intracellularly and may have therapeutic and/or cosmetic efficacy. These released intracellular components may have therapeutic or cosmetic efficacy. For examples, a patient's own cells may be run through the system 10 and subject to destruction or lysis to release the intracellular contents. The intracellular contents may then be retrieved and used in the patient. These could be used immediately after processing in some embodiments or they could be collected and stored for future use. In some embodiments, the extracted intracellular components may be used in the same patient (i.e., autologous) or a different patient (i.e., allogeneic). In additional embodiments, the processed cells are optionally cultured, e.g., in an in vitro culture media with appropriate nutrients etc. to promote cell growth. In several embodiments, conditions are selected in order to enhance secretome production by the cells. This may include, certain growth factors, media concentrations/pH, or in some embodiments hypoxic culture conditions (e.g., about 0.1%, about 0.5%, about 1% $O_2$) to optimize secretome production. In several embodiments, the cultured cells (post-processing) secrete one or more components that can be isolated from the culture media. In several embodiments, the cultured cells (post-processing) produce one or more factors that are integral membrane or membrane tethered that can also be isolated by lysing or otherwise treating the cells. In several embodiments, these isolated factors can be stored and used as an off the shelf therapeutic, for either allogeneic or autologous treatments. Non-limiting examples of components that may be isolated from the cultured (post-processing) cells include various proteins, cytokines, exosomes and the like, as described above. In several embodiments, these factors include, but are not limited to, VEGF, HGF, IGF-1, SDF-1, PDGF-BB, NGF-β, SCF, bFGF, TNF-α, HGFA, MFG-E8 and combinations thereof. In several embodiments, exosomes comprising miRNA are isolated, including those, for example that comprise miR-223, miR-146b, miR-126 and miR-199a, alone, in combination with one another or with other microRNA.

Figure 27A:
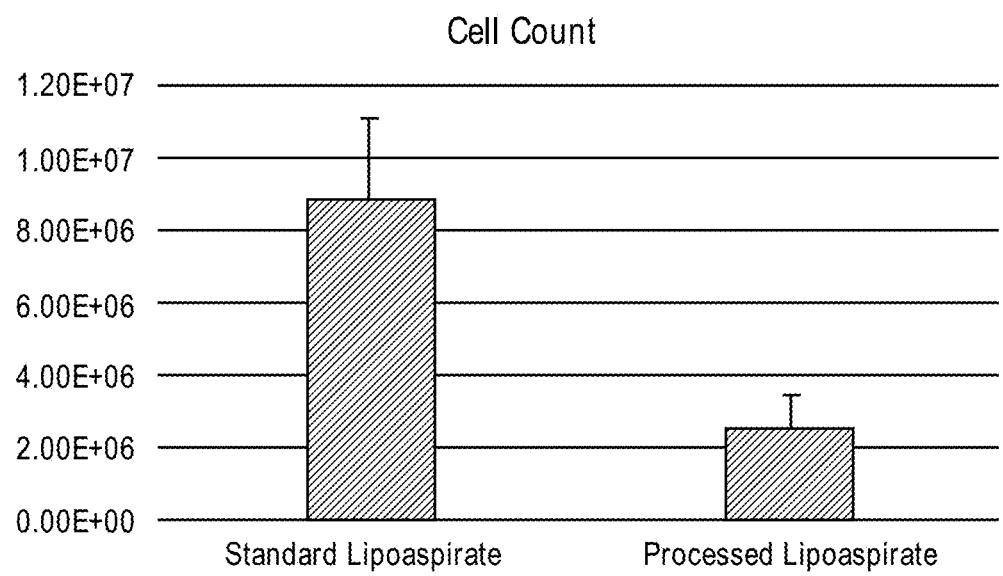
FIG. 27A illustrates a graph of cell count results for adipose tissue that was run through a tissue processing system disclosed herein (e.g., such as that illustrated in FIG. 5) using a microfluidic chip of the type illustrated in FIG. 14B ("processed lipoaspirate). Also illustrated in FIG. 27A are cell count results for standard lipoaspirate (i.e., not processed).
Figure 27B:
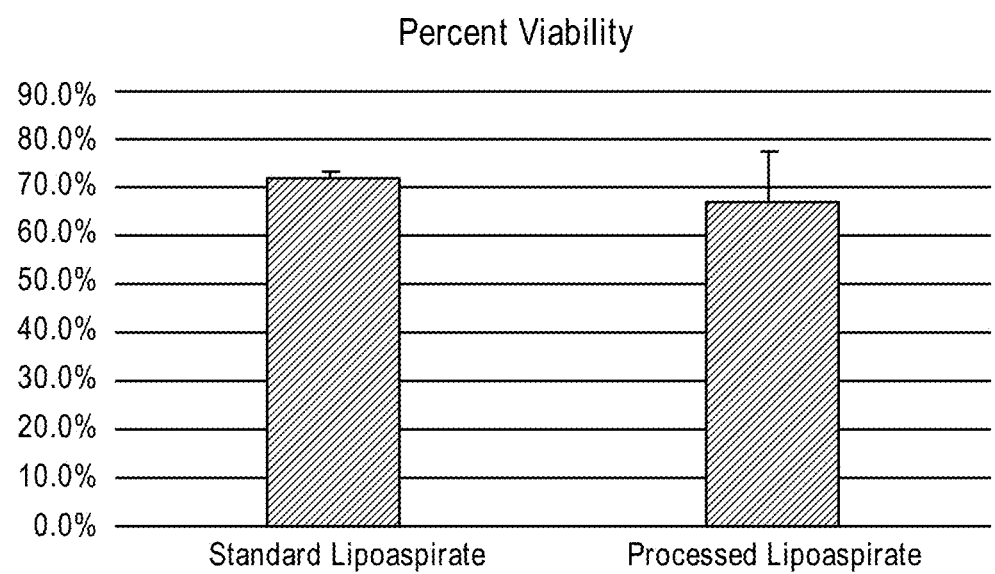
FIG. 27B illustrates a graph of cell viability results for adipose tissue that was run through the tissue processing system illustrated in FIG. 5 using a microfluidic chip of the type illustrated in FIG. 14B ("processed lipoaspirate"). Also illustrated in FIG. 27A are viability results for standard lipoaspirate (i.e., not processed).

FIGS. 27A and 27B illustrate, respectively, a graph of cell count and cell viability results for adipose tissue that was run through the tissue processing system illustrated in FIG. 5 using a microfluidic chip 14 of the type illustrated in FIG. 14B along with fresh, unprocessed adipose tissue (standard lipoaspirate). Fresh adipose tissue was either left unprocessed (standard lipoaspirate) or processed using the tissue processing system (processed lipoaspirate) at 1600 RPM for twenty (20) cycles (each cycle include a 360° rotation of the microfluidic chip 14). Subsequently, each processed sample was combined with 0.1% collagenase to harvest the stromal vascular fraction.

Briefly, a 0.1% enzymatic digestion solution was prepared by combining type I collagenase (Sigma-Aldrich Co., St. Louis, Mo.) with phosphate-buffered saline, which was then sterilized using a 0.22-µm vacuum filter (Millipore Corp., Billerica, Mass.). A 1:1 volume of collagenase solution to lipoaspirate was incubated in a water bath at 37° C. for 30 minutes, swirling intermittently. An equal volume of control medium (Dulbecco's Modified Eagle Medium, 10% fetal bovine serum, 500 IU penicillin, and 500 µg streptomycin) was then added to neutralize enzymatic activity, and the mixture was allowed to separate for at least 10 minutes. The liquid infranatant layer containing the stromal vascular fraction was isolated, filtered through a 100-µm cell strainer (Corning, Inc., Durham, N.C.), and centrifuged at 1800 rpm for 8 minutes. Each pellet was then resuspended in red blood cell lysis buffer (15.5 mM ammonium chloride, 1 mM potassium bicarbonate, and 0.01 mM ethylenediaminetetraacetic acid) for 5 minutes to minimize erythrocyte contamination. After the addition of 5 ml of control medium, the suspensions were centrifuged one final time. The aqueous portions were removed by aspiration after each centrifugation step. The resulting pellets were then resuspended in control media and subjected to staining and analysis.

A portion of the freshly isolated stromal vascular fraction (SVF) obtained from each sample was subjected to acridine orange/propidium iodide staining (Logos Biosystems, Inc., Annandale, Va.) and quantified using a dual fluorescence automated cell counter (Logos Biosystems) that delineates live versus dead and nucleated versus non-nucleated cells. Finally, the single cell suspensions were then aliquoted in polystyrene tubes and stained with propidium iodide. Each tube was subjected to the absolute cell count function of the flow cytometer (Miltenyi Biotec, Inc., Bergisch Gladbach, Germany) to assess viability. FIG. 27A illustrates a graph of cell count for the standard lipoaspirate as well as the processed lipoaspirate (using the device of FIG. 5). Processing of the sample using the device at 1600 RPM results in a ~4-fold decrease in the number of SVF cells recovered. Processing using the device at 1600 RPM does not result in any discernable difference in the viability of the cells recovered as seen by FIG. 27B. Generally, it was found that at different applied shear rates, as the cumulative shear force increased upon the cells this results in increased destruction of the cells.

Stem cell subtypes and stem cell markers were analyzed in both the standard lipoaspirate and the processed lipoaspirate using a flow cytometry. First, the mesenchymal stem cell (MSC) population was identified by gating viable cells (those to the right of the 200 hashmark on the X-axis of the forward-scatter versus side-scatter window). Next, the viable cell population that was CD45 negative was exclusively gated exclusively. Finally, cells that were CD31 negative and CD45 positive were identified. It was found that processed lipoaspirate contains a greater proportion of MSCs (CD45−/CD31−/CD34+) than does the standard lipoaspirate counterpart.

Figure 28:
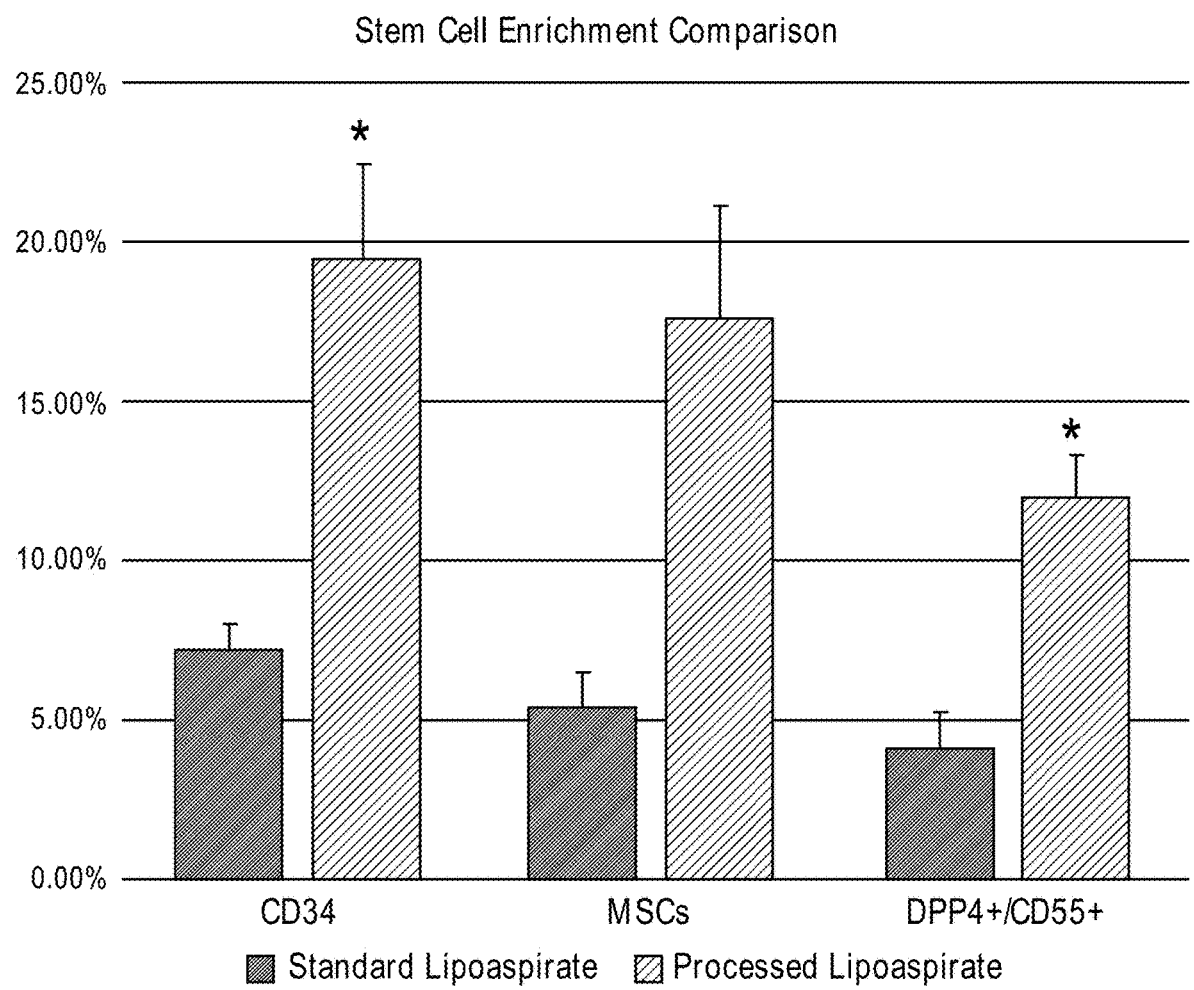
FIG. 28 is a graph illustrating the improved enrichment of stem cells in processed lipoaspirate as compared to standard lipoaspirate. An "*" indicates statistical significant at $p<0.05$.

FIG. 28 illustrates a graphical representation of the stem cell markers and subtypes identified from the SVF of cells obtained from standard lipoaspirate versus processed lipoaspirate (with the device of FIG. 5). CD34 is a universal stem cell marker that is upregulated nearly 3-fold after device processing. Similarly, both the MSC subpopulation (CD45−/CD31−/CD34+) and a MSC subpopulation critical to the healing of diabetic wounds (CD45−/CD31−/CD34+/DPP4+/CD55+) are found to be enriched after processing. Graph bars represented with a represent $p<0.05$.

Figure 29:
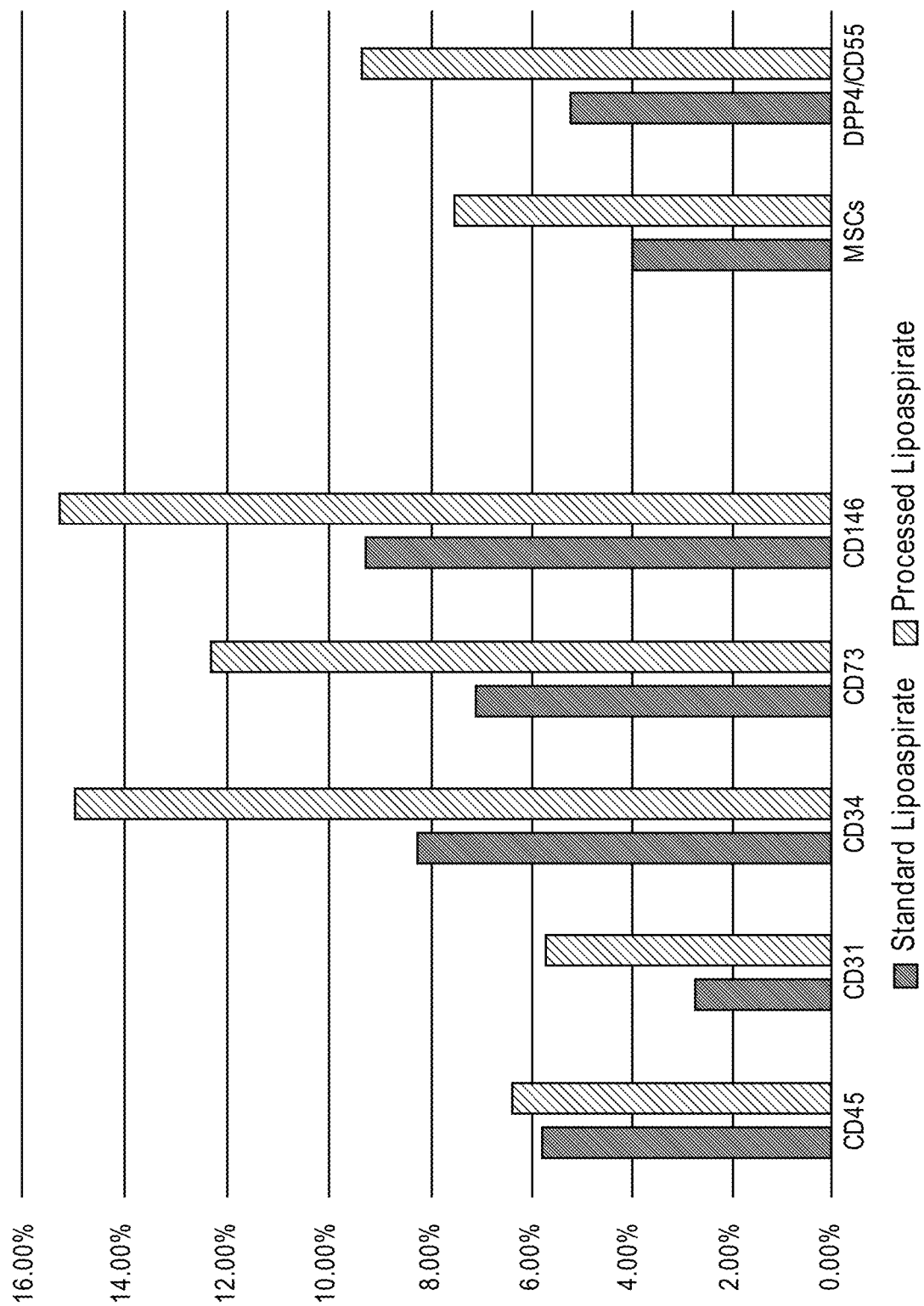
FIG. 29 illustrates a graph of stem cell markers (CD45, CD31, CD34, CD73, CD146, MSCs, DPP4/CD55) for both the processed lipoaspirate and the standard lipoaspirate.

Diabetic lipoaspirate that was processed using the device of FIG. 5 and standard diabetic lipoaspirate (not processed) was analyzed for stem cell markers and subtypes. FIG. 29 illustrates a graph of stem cell markers (CD45, CD31, CD34, CD73, CD146, MSCs, DPP4/CD55) for both the processed lipoaspirate and the standard lipoaspirate. CD34 is a universal stem cell marker. In this particular tested patient, CD34 is upregulated nearly 2-fold after device processing. Similarly, other MSC markers (CD73, CD146) as well as endothelial marker (CD31) are upregulated after device processing. Finally, both the MSC subpopulation (CD45−/CD31−/CD34+) and a MSC subpopulation critical to the healing of diabetic wounds (CD45−/CD31−/CD34+/DPP4+/CD55+) are found to be enriched after processing of diabetic tissue.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "administering a population of expanded NK cells" include "instructing the administration of a population of expanded NK cells." In addition, where features or aspects of the disclosure are described in terms of Markush groups, those skilled in the art will recognize that the disclosure is also thereby described in terms of any individual member or subgroup of members of the Markush group.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 10 nanometers" includes "10 nanometers."

While embodiments of the present invention have been shown and described, various modifications may be made without departing from the scope of the present invention. The invention, therefore, should not be limited, except to the following claims, and their equivalents.

What is claimed is:

1. A system for processing biological samples comprising:
a support plate comprising:
a central portion comprising a receiving element,
wherein the receiving element is configured to reversibly interact with a drive shaft of a motor, the motor configured to apply centrifugal movement to the support plate,
wherein the central portion lies in a plane perpendicular to an axis of rotation of the drive shaft of the motor;
a lateral portion comprising a plurality of interacting regions, each configured to reversibly interact with one of a plurality of carriages,
wherein the lateral portion extends radially from the central portion and at least partially lies within a plane parallel to the plane of the central portion,
a plurality of carriages, wherein each of the plurality of carriages is configured to be operatively coupled to the lateral portion of the support plate,
each of the plurality of carriages comprising:
a first end and a second end and a base portion extending between the first and second ends,
a receiving region configured to reversibly interact with a microfluidic chip that is fluidically coupled to at least one sample chamber configured to receive a sample for processing, wherein the sample chamber is configured to be removable from the microfluidic chip, and wherein the sample for processing is configured to flow bidirectionally between the microfluidic chip and the at least one sample chamber;
a post extending orthogonally from the base portion and configured to interact with one of the plurality of interacting regions of the lateral portion;
wherein a primary axis of rotation is substantially parallel to the axis of rotation of the drive shaft of the motor,
wherein each of the plurality of carriages is positioned about one of a plurality of secondary axes, wherein during operation each of the plurality of secondary axes is substantially parallel to the primary axis, and
wherein each of the plurality of carriages is at least intermittently rotatable about one of the plurality of axes through an arc of about 180 degrees.

2. The system of claim 1, further comprising a plurality of microfluidic chips, each microfluidic chip comprising:
a central body portion positioned between a first end and a second end, each of the first and second end configured to fluidically interact with the sample chamber, at least one microfluidic channel extending between the first and second ends, the at least one channel comprising varied dimensions and configured to allow passage of a sample from the first end to the second end, wherein each of the plurality of microfluidic chips are dimensioned to fit within a corresponding receiving region on a corresponding carriage.

3. The system of claim 2, wherein each microfluidic chip is reversibly fluidically coupled to a corresponding sample chamber on each of the first and second ends,
wherein each sample chamber comprises a vent and a vent channel that is fluidly connected to the interior of the sample chamber,
wherein each sample chamber is reversibly fluidically coupled to the microfluidic chip via an adapter,
wherein each carriage comprises a capture element on the first and second ends, the capture elements configured to communicate with a release element on the lateral portion of the support plate, wherein the communication between the capture elements and release element allows the intermittent rotation of each of the plurality of carriages.

4. The system of claim 3, wherein the capture elements comprise magnets of a first polarity and the release element comprises a magnet of an opposite polarity.

5. The system of claim 1, wherein the lateral portion of the support plate comprises a plurality of arms, with each arm comprising a corresponding interacting region, wherein the arms and the central portion are a unitary structure.

6. The system of claim 1, wherein the lateral portion comprises at least three arms, each of the three arms comprising an interacting region configured to interact with one of at least three carriages comprising a first and second end, each of the carriages configured to reversibly interact with one of at least three microfluidic chips, each chip comprising a first end, a second end, and a body therebetween, each end of the microfluidic chip being fluidically coupled to a sample chamber, and the body of the chip comprising a plurality of microfluidic pathways extending between the first and second ends, and wherein the carriages are configured to intermittently rotate between a first position where the first end is positioned at a first location at a first distance from the receiving element of the central portion and a second position wherein the first end is positioned at second location at a second distance from the receiving element of the central portion, wherein the first distance is greater than the second distance.

7. A system for processing samples comprising:
a support plate including a plurality of arms, wherein each of the plurality of arms extends radially from the support plate;
a motor, coupled to the support plate and configured to rotate the support plate; and
a plurality of carriages,
wherein each of the plurality of carriages is arranged on one of the plurality of arms on the support plate, wherein a primary axis of rotation extends perpendicularly from the arm that the carriage is arranged on,
wherein each of the plurality of carriages is positioned about one of a plurality of secondary axes, wherein each of the plurality of carriages is substantially parallel to the primary axis of rotation,
wherein each of the plurality of carriages is configured to receive: (i) a microfluidic chip, (ii) a first sample chamber, and (iii) a second sample chamber for receiving a sample for processing, the first sample chamber includes an opening that is fluidly connected to a first inlet on a first end of the microfluidic chip and is configured to be removable from the first inlet of the microfluidic chip, and the second sample chamber includes an opening that is fluidly connected to a second inlet on a second end of the microfluidic chip and is configured to be removable from the second inlet of the microfluidic chip, and
wherein the respective fluidic connections between the microfluidic chip and the first and second sample chambers allow for bidirectional flow of the sample through the microfluidic chip, and
wherein each of the plurality of carriages is rotatable about one of the plurality of axes.

8. The system for processing samples of claim 7, wherein each of the plurality of carriages is configured to rotate 180 degrees about one of the plurality of axes.

9. The system for processing samples of claim 7, wherein each of the plurality of carriages is configured to receive a first sample chamber and a second sample chamber, wherein the first sample chamber is positioned on a first end of the microfluidic chip, and wherein the second sample chamber is positioned on a second end of the microfluidic chip.

10. The system for processing samples of claim 7, wherein the at least one sample chamber includes a vent and a vent channel that is fluidly connected to the interior of the sample chamber, wherein the vent is configured to provide laminar flow through the sample chamber.

11. The system for processing samples of claim 7, wherein each of the plurality of carriages is retained in an opening of each of the plurality of arms, wherein each of the plurality of carriages extends through the opening of each of the plurality of arms.

12. The system for processing samples of claim 11, wherein each of the plurality of carriages is retained along a plane of each of the plurality of arms.

13. A system for processing samples comprising:
a support plate including a plurality of arms, wherein each of the plurality of arms extends radially from the support plate;
a plurality of carriages,
wherein each of the plurality of carriages is arranged on one of the plurality of arms on the support plate, wherein a primary axis of rotation extends perpendicularly from the arm that the carriage is arranged on,
wherein each of the plurality of carriages is positioned about one of a plurality of secondary axes, wherein each of the plurality of carriages is substantially parallel to the primary axis of rotation,
wherein each of the plurality of carriages is configured to reversibly receive a microfluidic chip and at least one sample chamber for receiving a sample for processing, wherein the at least one sample chamber includes an opening that is fluidly connected to the microfluidic chip and the at least one sample chamber is external to the microfluidic chip, thereby allowing bidirectional flow between the microfluidic chip and the at least one sample chamber, and
wherein each of the plurality of carriages is rotatable about one of the plurality of axes.

14. The system for processing samples of claim 13, wherein each of the plurality of arms further comprises:
a first engagement structure,
a second engagement structure located a distance from the first engagement structure, and
wherein the first engagement structure and the second engagement structure are each configured to engage with one of a first structure located on a first end of the carriage and a second structure located on a second end of the carriage, and wherein the first and second engagement structures are configured to release and engage the first structure and the second structure interchangeably such that the carriage is configured to move between a plurality of orientations about one of the plurality of axes.

15. The system for processing samples of claim 14, wherein an acceleration or deceleration force is configured to move the carriage between the plurality of orientations.

16. The system for processing samples of claim 14, wherein the carriage comprises a gear assembly, the gear assembly is configured to move the carriage between the plurality of orientations.

17. The system for processing samples of claim 14, wherein the carriage comprises a centripetal ratchet, the centripetal ratchet configured to move the carriage between the plurality of orientations.

18. The system for processing samples of claim 14, comprising a first sample chamber and a second sample chamber, the first sample chamber including an opening that is fluidly connected to a first inlet of the microfluidic chip and is configured to be removable from the first inlet of the microfluidic chip, and the second sample chamber including an opening that is fluidly connected to a second inlet of the microfluidic chip and is configured to be removable from the second inlet of the microfluidic chip.

* * * * *